(12) United States Patent
Takeda et al.

(10) Patent No.: US 9,200,171 B2
(45) Date of Patent: Dec. 1, 2015

(54) AZO COMPOUND AND INK CONTAINING THE COMPOUND

(71) Applicant: MITSUBISHI CHEMICAL CORPORATION, Chiyoda-ku (JP)

(72) Inventors: Utako Takeda, Kanagawa (JP); Shoko Ichinosawa, Kanagawa (JP); Yuki Tanaka, Kanagawa (JP); Hiroyuki Aikyo, Kanagawa (JP); Mio Ishida, Kanagawa (JP)

(73) Assignee: MITSUBISHI CHEMICAL CORPORATION, Chiyoda-ku (JP)

( * ) Notice: Subject to any disclaimer, the term of this patent is extended or adjusted under 35 U.S.C. 154(b) by 78 days.

(21) Appl. No.: 14/084,972

(22) Filed: Nov. 20, 2013

(65) Prior Publication Data

US 2014/0078577 A1  Mar. 20, 2014

Related U.S. Application Data

(63) Continuation of application No. PCT/JP2012/062702, filed on May 17, 2012.

(30) Foreign Application Priority Data

May 20, 2011 (JP) .................................. 2011-113759
Oct. 3, 2011 (JP) .................................. 2011-219414
Jan. 13, 2012 (JP) .................................. 2012-005119
Apr. 5, 2012 (JP) .................................. 2012-086605

(51) Int. Cl.

| C09D 11/037 | (2014.01) |
|---|---|
| C09D 11/50 | (2014.01) |
| C09B 29/039 | (2006.01) |
| C09B 29/042 | (2006.01) |
| C09B 31/043 | (2006.01) |
| C09B 31/147 | (2006.01) |
| G02B 26/00 | (2006.01) |
| G02F 1/167 | (2006.01) |
| B41J 3/407 | (2006.01) |
| C07D 231/46 | (2006.01) |
| C07D 333/38 | (2006.01) |
| C07D 409/04 | (2006.01) |
| C07D 417/14 | (2006.01) |
| C07D 277/32 | (2006.01) |
| C07D 277/50 | (2006.01) |
| C09B 29/01 | (2006.01) |
| C09B 29/40 | (2006.01) |
| C09B 29/36 | (2006.01) |
| C09B 23/10 | (2006.01) |
| C09B 29/036 | (2006.01) |
| C09B 29/033 | (2006.01) |

(Continued)

(52) U.S. Cl.
CPC ............... *C09D 11/50* (2013.01); *B41J 3/4076* (2013.01); *C07D 231/46* (2013.01); *C07D 277/32* (2013.01); *C07D 277/50* (2013.01); *C07D 333/38* (2013.01); *C07D 409/04* (2013.01); *C07D 417/14* (2013.01); *C09B 1/16* (2013.01); *C09B 1/201* (2013.01); *C09B 1/285* (2013.01); *C09B 1/42* (2013.01); *C09B 1/50* (2013.01); *C09B 1/515* (2013.01); *C09B 1/585* (2013.01); *C09B 23/105* (2013.01); *C09B 29/0003* (2013.01); *C09B 29/0037* (2013.01); *C09B 29/0059* (2013.01); *C09B 29/0081* (2013.01); *C09B 29/0085* (2013.01); *C09B 29/0088* (2013.01); *C09B 29/081* (2013.01); *C09B 29/366* (2013.01); *C09B 29/3613* (2013.01); *C09B 29/3647* (2013.01); *C09B 31/043* (2013.01); *C09B 31/147* (2013.01); *C09B 35/34* (2013.01); *C09B 43/006* (2013.01); *G02B 26/005* (2013.01); *G02F 1/167* (2013.01); *C09D 11/037* (2013.01)

(58) Field of Classification Search
CPC .. C09D 11/037; C09D 11/50; C09B 29/0003; C09B 29/0037; C09B 29/0059; C09B 29/0081; C09B 29/0085; C09B 29/0088; C09B 29/081; C09B 29/3613; C09B 29/3647; C09B 29/366; C09B 31/043; C09B 31/147; G02B 26/005; G02F 1/167; B41J 3/4076
USPC ........... 106/31.5, 31.44, 31.45; 534/795, 761; 359/290, 296
See application file for complete search history.

(56) References Cited

U.S. PATENT DOCUMENTS

| 4,621,136 A | 11/1986 | Imahori et al. |
|---|---|---|
| 4,764,178 A | 8/1988 | Gregory et al. |

(Continued)

FOREIGN PATENT DOCUMENTS

| JP | 57-109860 | 7/1982 |
|---|---|---|
| JP | 57-111356 | 7/1982 |

(Continued)

OTHER PUBLICATIONS

Abstract of JP 03/256793, Nov. 1991.*

(Continued)

*Primary Examiner* — Helene Klemanski
(74) *Attorney, Agent, or Firm* — Oblon, McClelland, Maier & Neustadt, L.L.P.

(57) ABSTRACT

An object of the present invention is to provide an ink containing an azo compound which is excellent in solubility in a solvent and has a high extinction coefficient. The present invention relates to an ink comprising a solvent having a relative permittivity of 3 or less, as measured at a frequency of 1 kHz and at 22° C. and having a solubility in water of 20 mg/L or less at 25° C. and a specific azo compound.

16 Claims, No Drawings

(51) Int. Cl.

| | |
|---|---|
| *C09B 29/08* | (2006.01) |
| *C09B 29/50* | (2006.01) |
| *C09B 35/34* | (2006.01) |
| *C09B 43/00* | (2006.01) |
| *C09B 1/16* | (2006.01) |
| *C09B 1/20* | (2006.01) |
| *C09B 1/28* | (2006.01) |
| *C09B 1/42* | (2006.01) |
| *C09B 1/50* | (2006.01) |
| *C09B 1/515* | (2006.01) |
| *C09B 1/58* | (2006.01) |

(56) References Cited

U.S. PATENT DOCUMENTS

| | | | | |
|---|---|---|---|---|
| 5,296,448 | A | | 3/1994 | Bradbury et al. |
| 5,510,314 | A | | 4/1996 | Evans et al. |
| 5,683,956 | A | | 11/1997 | Bowman et al. |
| 5,782,934 | A | | 7/1998 | Hall et al. |
| 7,800,816 | B2 | * | 9/2010 | Hayes et al. .................. 359/320 |
| 2010/0292450 | A1 | | 11/2010 | Shiga et al. |
| 2013/0188238 | A1 | * | 7/2013 | Shiga et al. .................. 106/31.5 |

FOREIGN PATENT DOCUMENTS

| | | |
|---|---|---|
| JP | 57-125262 | 8/1982 |
| JP | 57-125263 | 8/1982 |
| JP | 60-239291 | 11/1985 |
| JP | 61-41596 | 2/1986 |
| JP | 62-55194 | 3/1987 |
| JP | 3-256793 | 11/1991 |
| JP | 5-112080 | 5/1993 |
| JP | 8-267939 | 10/1996 |
| JP | 9-109561 | 4/1997 |
| JP | 9-109566 | 4/1997 |
| JP | 9-503592 A | 4/1997 |
| JP | 9-176532 | 7/1997 |
| JP | 9-508939 | 9/1997 |
| JP | 10-119441 | 5/1998 |
| JP | 2000-313174 | 11/2000 |
| JP | 2007-99823 | 4/2007 |
| JP | 2007-515509 | 6/2007 |
| JP | 2007-531917 | 11/2007 |
| JP | 2009-138189 | 6/2009 |
| WO | WO 2005/054375 A1 | 6/2005 |
| WO | WO 2005/098524 A1 | 10/2005 |
| WO | WO 2008/142086 A1 | 11/2008 |
| WO | WO 2009/063880 A1 * | 5/2009 |
| WO | WO 2010/031860 A2 | 3/2010 |
| WO | WO 2012/033177 A1 * | 3/2012 |

OTHER PUBLICATIONS

International Search Report issued Jul. 17, 2012 in Application No. PCT/JP2012/062702 (With English Translation).

Robert A. Hayes, et al. "Video-speed electronic paper based on electrowetting", Nature, vol. 425, Sep. 25, 2003, pp. 383-385.

Combined Chinese Office Action and Search Report issued Sep. 2, 2014 in Patent Application No. 201280024560.X (with English language translation and English translation of categories of cited documents).

Office Action issued Apr. 13, 2015 in Chinese Patent Application No. 201280024560.X (with English language translation).

* cited by examiner

AZO COMPOUND AND INK CONTAINING THE COMPOUND

TECHNICAL FIELD

The present invention relates to an azo compound and an ink containing the compound. More particularly, the invention relates to an azo compound having a specific chemical structure and an ink which contains the compound and is useful as a display material or for an optical shutter.

BACKGROUND ART

An electrowetting display is an image display system which includes a substrate and, disposed thereon, a plurality of pixels filled with two phases of an aqueous medium and an oil-based coloring ink, and in which the affinity of the aqueous medium/substrate interface is controlled for each pixel by means of a voltage application on-off operation to spread/gather the oil-based coloring ink on the substrate and thereby an image is displayed (Non-Patent Document 1). The colorants for use in electrowetting displays are required to have high solubility in low-polarity solvents and the other properties (Patent Document 1 and Patent Document 2).

Patent Documents 3 to 6 show polyester fiber dye colorants each using a disazo compound excellent in fastness. Moreover, Patent Document 7 shows a cyan colorant for use in thermal-transfer sheets, which easily at least sublimes or thermally diffuses and an ink composition using the colorant, and mentions media for ink preparation.

PRIOR ART LITERATURE

Patent Documents

Patent Document 1: JP-T-2007-531917 (The term "JP-T" as used herein means a published Japanese translation of a PCT patent application.)
Patent Document 2: International Publication WO2010/031860
Patent Document 3: JP-A-57-109860
Patent Document 4: JP-A-57-111356
Patent Document 5: JP-A-57-125262
Patent Document 6: JP-A-57-125263
Patent Document 7: JP-A-3-256793

Non-Patent Document

Non-Patent Document 1: "Nature", (Great Britain), 2003, Vol. 425, pp. 383-385

SUMMARY OF THE INVENTION

Problems that the Invention is to Solve

However, the above Patent Document 2 does not specifically shows a colorant having a high solubility in low-polar solvents and a high extinction coefficient.

Moreover, there are descriptions on dye colorants in the above Patent Documents 3 to 6 and there is a description of a colorant and media for ink adjustment in the above Patent Document 7. However, these documents neither describe nor suggest solubility of the colorants in solvents, particularly solubility in low-polar solvents.

An object of the invention is to provide an ink containing a compound, which is excellent in solubility in low-polarity solvents and has a high extinction coefficient, and an ink containing the compound.

Means for Solving the Problems

The present inventors diligently made investigations in order to overcome the problems described above. As a result, they have found that an azo compound having a certain chemical structure is excellent in solubility in solvents and further has a high molar extinction coefficient. The invention has been accomplished on the basis of these findings.

Namely, essential points of the invention are described in the following (1) to (15).

(1) An ink comprising: a solvent having a relative permittivity of 3 or less, as measured at a frequency of 1 kHz and at 22° C., and having a solubility in water of 20 mg/L or less at 25° C.; and an azo compound, the azo compound being represented by the following general formula (I):

[Chem 1]

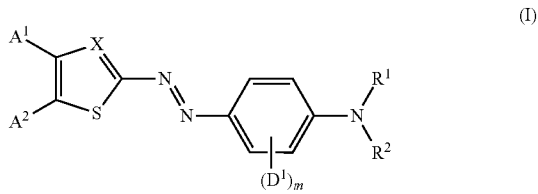

wherein $R^1$, $R^2$, $D^1$, $A^1$, and $A^2$ each independently represent an arbitrary substituent, m represents an integer of 1 to 4, and when m is 2 or larger, two or more $D^1$ groups present in one molecule may be the same or different, and X represents a nitrogen atom or an optionally substituted methine group.

(2) The ink according to the item (1) above, wherein the solvent contains at least one selected from the group consisting of hydrocarbon solvents, silicone oils, and fluorocarbon solvents.

(3) The ink according to the item (1) or (2) above, wherein the product of a molar extinction coefficient ε (L·mol$^{-1}$·cm$^{-1}$) at the absorption-maximum wavelength of an n-decane solution of the azo compound and a saturated concentration C (mol·L$^{-1}$) of the azo compound in n-decane at 5° C., εC, is 1,000 cm$^{-1}$ or larger.

(4) The ink according to any one of the items (1) to (3) above, which further comprises at least one selected from the group consisting of heterocyclic compounds, cyanovinyl compounds, and anthraquinone compounds.

(5) The ink according to the item (4) above, wherein the heterocyclic compound is at least one selected from the group consisting of the following general formulae (III) to (V):

[Chem 2]

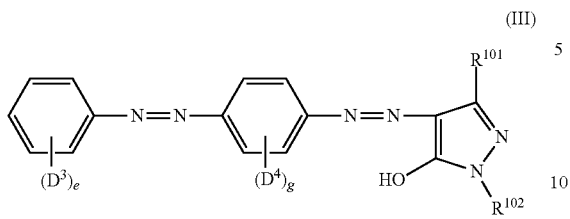

(III)

wherein $R^{101}$, $R^{102}$, $D^3$, and $D^4$ each independently represent an arbitrary substituent, e represents an integer of 1 to 5, and when e is 2 or larger, two or more $D^3$ groups present in one molecule may be the same or different, and g represents an integer of 1 to 4, and when g is 2 or larger, two or more $D^4$ groups present in one molecule may be the same or different;

[Chem 3]

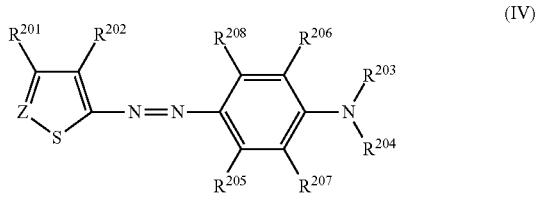

(IV)

wherein $R^{201}$, $R^{202}$, $R^{203}$, $R^{204}$, $R^{205}$, $R^{206}$, $R^{207}$, and $R^{208}$ each independently represent an arbitrary substituent and Z represents a nitrogen atom or an optionally substituted methine group;

[Chem 4]

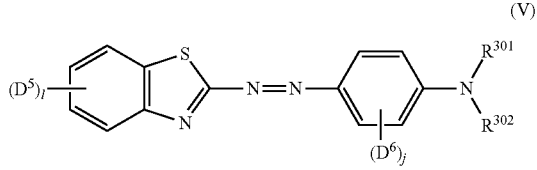

(V)

wherein $R^{301}$, $R^{302}$, $D^5$, and $D^6$ each independently represent an arbitrary substituent, l represents an integer of 1 to 4, and when l is 2 or larger, two or more $D^5$ groups present in one molecule may be the same or different, and j represents an integer of 1 to 4, and when j is 2 or larger, two or more $D^6$ groups present in one molecule may be the same or different.

(6) The ink according to the item (4) or (5) above, wherein the cyanovinyl compound is represented by the following general formula (VI):

[Chem 5]

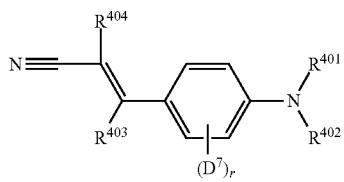

(VI)

wherein $R^{401}$, $R^{402}$, $R^{403}$, $R^{404}$, and $D^7$ each independently represent an arbitrary substituent and r represents an integer of 1 to 4, and when r is 2 or larger, two or more $D^7$ groups present in one molecule may be the same or different.

(7) The ink according to any one of the items (4) to (6) above, wherein the anthraquinone compound is represented by the following general formula (VII):

[Chem 6]

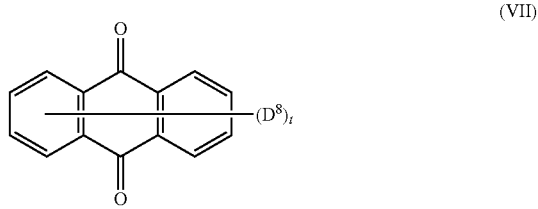

(VII)

wherein $D^8$ represents an arbitrary substituent and t represents an integer of 1 to 8, and when t is 2 or larger, two or more $D^8$ groups present in one molecule may be the same or different.

(8) The ink according to any one of the items (1) to (7) above, which is for use in a display or optical shutter.

(9) A display comprising a display part containing the ink according to any one of the items (1) to (7) above, wherein an image is displayed by controlling voltage application to the display part.

(10) The display according to the item (9) above, wherein the display part further contains electrophoretic particles or an aqueous medium.

(11) The display according to the item (9) or (10) above, wherein an image is displayed by changing a colored state by means of voltage application.

(12) The display according to any one of the items (9) to (11) above, wherein an image is displayed by an electrowetting system or an electrophoretic system.

(13) An electronic paper which comprises the display according to any one of the items (9) to (12) above.

(14) An azo compound represented by the following general formula (VIII):

[Chem 7]

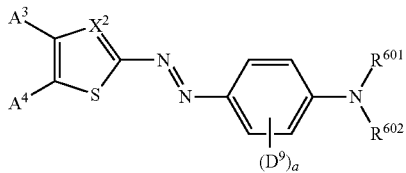

(VIII)

wherein $R^{601}$ and $R^{602}$ each independently represent an optionally substituted branched alkyl group having 7 to 20 carbon atoms, $D^9$ represents a hydrogen atom, a halogen atom, an optionally substituted alkyl group having 1 to 20 carbon atoms, an optionally substituted alkoxy group having 1 to 20 carbon atoms, an —NHCOR$^{603}$ group, or an —NHSO$_2$R$^{608}$ group, $R^{603}$ and $R^{608}$ each independently represent an optionally substituted alkyl group having 1 to 20 carbon atoms, an optionally substituted aryl group having 6 to 20 carbon atoms, or an optionally substituted heteroaryl group having 2 to 20 carbon atoms, a represents an integer of 1 to 4, and when a is 2 or larger, two or more $D^9$ groups present in one molecule may be the same or different, $A^3$ represents a halogen atom, a cyano group, an optionally substituted alkyl group having 1 to 20 carbon atoms, an optionally substituted aryl group having 6 to 20 carbon atoms, an optionally substituted heteroaryl group having 2 to 20 carbon atoms, an optionally substituted alkoxy group having 1 to 20 carbon atoms, or a —COOR$^{604}$ group, $R^{604}$ represents an optionally substituted alkyl group having 1 to 20 carbon atoms, an optionally substituted aryl group having 6 to 20 carbon atoms, or an optionally substituted heteroaryl group having 2 to 20 carbon atoms, $A^4$ represents a halogen atom, an optionally substituted alkyl group having 1 to 20 carbon atoms, an optionally substituted alkenyl group having 2 to 20 carbon atoms, an optionally substituted alkylcarbonyl group having 2 to 20 carbon atoms, an optionally substituted alkoxycarbonyl group having 2 to 20 carbon atoms, a formyl group, an R$^{605}$OOC(NC)C=CH— group, or an NC(NC)C=CH— group, $R^{605}$ represents an optionally substituted alkyl group having 1 to 20 carbon atoms, an optionally substituted aryl group having 6 to 20 carbon atoms, or an optionally substituted heteroaryl group having 2 to 20 carbon atoms, $X^2$ represents a nitrogen atom, or a methine group which may have a halogen atom, a cyano group, or a —COOR$^{607}$ group as a substituent, and $R^{607}$ represents an optionally substituted alkyl group having 1 to 20 carbon atoms, an optionally substituted aryl group having 6 to 20 carbon atoms, or an optionally substituted heteroaryl group having 2 to 20 carbon atoms.

(15) An azo compound represented by the following general formula (IX):

[Chem 8]

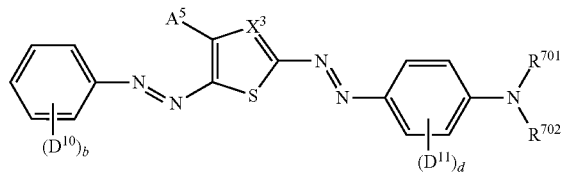

(IX)

wherein $R^{701}$ and $R^{702}$ each independently represent an optionally substituted branched alkyl group having 5 to 20 carbon atoms, $D^{11}$ represents a hydrogen atom, a halogen atom, an optionally substituted alkyl group having 1 to 20 carbon atoms, an optionally substituted alkoxy group having 1 to 20 carbon atoms, an —NHCOR$^{703}$ group, or an —NHSO$_2$R$^{708}$ group, $R^{703}$ and $R^{708}$ each independently represent an optionally substituted alkyl group having 1 to 20 carbon atoms, an optionally substituted aryl group having 6 to 20 carbon atoms, or an optionally substituted heteroaryl group having 2 to 20 carbon atoms, d represents an integer of 1 to 4, and when d is 2 or larger, two or more $D^{11}$ groups present in one molecule may be the same or different, $A^5$ represents a hydrogen atom, a halogen atom, a cyano group, an optionally substituted alkyl group having 1 to 20 carbon atoms, an optionally substituted aryl group having 6 to 20 carbon atoms, an optionally substituted heteroaryl group having 2 to 20 carbon atoms, an optionally substituted alkoxy group having 1 to 20 carbon atoms, or a —COOR$^{704}$ group, $R^{704}$ represents an optionally substituted alkyl group having 1 to 20 carbon atoms, an optionally substituted aryl group having 6 to 20 carbon atoms, or an optionally substituted heteroaryl group having 2 to 20 carbon atoms, $D^{10}$ represents a hydrogen atom, a halogen atom, a cyano group, an optionally substituted alkyl group having 1 to 20 carbon atoms, an optionally substituted alkoxy group having 1 to 20 carbon atoms, a —COOR$^{706}$ group, a —COR$^{709}$ group, or an —OCOR$^{710}$ group, b represents an integer of 1 to 5, and when b is 2 or larger, two or more $D^{10}$ groups present in one molecule may be the same or different, $R^{706}$, $R^{709}$, and $R^{710}$ each independently represent an optionally substituted alkyl group having 1 to 20 carbon atoms, an optionally substituted aryl group having 6 to 20 carbon atoms, or an optionally substituted heteroaryl group having 2 to 20 carbon atoms, $X^3$ represents a nitrogen atom, or a methine group which may have a halogen atom, a cyano group, or a —COOR$^{707}$ group as a substituent, and $R^{707}$ represents an optionally substituted alkyl group having 1 to 20 carbon atoms, an optionally substituted aryl group having 6 to 20 carbon atoms, or an optionally substituted heteroaryl group having 2 to 20 carbon atoms.

Advantage of the Invention

The azo compound according to the invention has a high solubility in oil-soluble solvents and can hence be used widely as inks. Furthermore, since an ink containing the azo compound according to the invention has a high solubility in low-polarity solvents and also a high molar extinction coefficient, the ink is useful as an ink for use in displays and optical shutters.

Furthermore, as the displays, the ink is especially useful in a display which has a display part containing an ink and in which an image is displayed by controlling voltage application to the display part, a display in which an image is displayed by changing a colored state by means of voltage application, and a display in which an image is displayed using electrophoretic particles or an aqueous medium in the display part.

The electrophoretic particles herein are charged particles and may have color and contain plural kinds of electrophoretic particles at the display part. Also, the aqueous medium is a fluid that may have color and may have plural kinds of aqueous media at the display part.

Moreover, the azo compound and ink of the invention are particularly useful as an ink for use in a display of an electrowetting system or a display of an electrophoretic system.

Furthermore, the ink of the invention can provide satisfactory inks of colors such as black excellent in hue by using the azo compound of the invention in combination with the other compound(s) and is also useful as a member which functions as an optical shutter.

The ink according to the invention can be used in any devices so long as they are display devices each having a display but is particularly useful for use in electronic papers.

MODES FOR CARRYING OUT THE INVENTION

Representative embodiments for carrying out the invention are explained below in detail. However, the invention can be carried out with various modifications unless the modifications exceed the gist of the invention, and should not be construed as being limited to the following embodiments.

Herein, "% by weight" and "% by mass" have the same meaning.

The ink according to the invention is an ink which includes a solvent having a relative permittivity, as measured at 22° C. at a frequency of 1 kHz, of 3 or less and having a solubility in water of 20 mg/L or less at 25° C. and an azo compound, and is characterized in that the azo compound is represented by the following general formula (I):

[Chem 9]

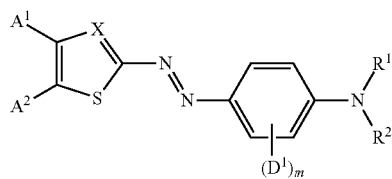

(I)

wherein $R^1$, $R^2$, $D^1$, $A^1$, and $A^2$ each independently represent an arbitrary substituent, m represents an integer of 1 to 4, and when m is 2 or larger, two or more $D^1$ groups present in one molecule may be the same or different, and X represents a nitrogen atom or an optionally substituted methine group.

(Solvent)

In the display or optical shutter of the invention, a low-polarity solvent is used as the solvent of the ink. The ink of the invention can be used, for example, in a display device that has layers such as an aqueous layer and an oily layer and that is based on a phenomenon in which a layer breaks up or a layer moves aside. For clear displaying, it is necessary that the ink-containing layer should stably break up or move aside without mingling with the aqueous layer and it is required that the solvent should have low compatibility with water and have low polarity, etc. According to the invention, since the ink contains a specific solvent and an azo compound, the oily layer can stably break up or move aside.

Meanwhile, in display devices utilizing electrophoresis, in which charged particles (electrophoretic particles) move in a solvent by the action of an electric field, there are cases where a high permittivity of the solution is an obstacle to the operation of the display device. Use of the specific solvent and azo compound according to the invention makes it possible to color a solution without hindering the movement of the particles.

The solvent to be used in the invention has a relative permittivity of 3 or less at 22° C., as measured at a frequency of 1 kHz. The relative permittivity thereof is preferably 2.5 or less, more preferably 2.2 or less. There is no particular lower limit on the relative permittivity thereof. It is, however, preferable that the relative permittivity is generally 1.5 or higher, preferably 1.8 or higher.

A method for measuring the relative permittivity of a solvent will be shown in the Examples. Moreover, in the case where a plurality of solvents are mixed and used as a solvent for the ink, the relative permittivity refers to relative permittivity of the mixed solvent.

When a layer in which the ink is contained has a relative permittivity falling within an appropriate range, there are cases where the display device can be operated without trouble. For example, in the case where the other layer, which contains no ink, is a liquid having electrical conductivity, polarity, or the like, such as water or a salt solution, when the relative permittivity of the solvent used in the ink-containing layer falls within an appropriate range, there are cases where the layers do not mingle with each other.

The solvent to be used in the invention has a solubility in water of 20 mg/L or less at 25° C. The solubility is preferably 10 mg/L or less, more preferably 5 mg/L or less. There is no lower limit and lower solubility is more preferable but the solubility is preferably 0.001 mg/L or more. A method for measuring the solubility of a solvent in water will be shown in Examples. Moreover, in the case where a plurality of solvents are mixed and used as a solvent for the ink, the solubility in water refers to solubility of the mixed solvent.

When the solubility in water is low, there are cases where the oil layer and the aqueous layer do not mingle with each other and the display device can be operated without trouble.

The boiling point of the solvent of the invention is not particularly limited. However, the boiling point thereof is preferably 120° C. or higher, more preferably 150° C. or higher, and particularly preferably 170° C. or lower. Moreover, it is preferably 300° C. or lower. When the solvent has a boiling point which is not too high, this solvent has neither too high a melting point nor too high a viscosity and there are cases where the display device can be operated without arousing a trouble therein. When the boiling point thereof is not too low, the solvent has reduced volatility and there are cases where stability and safety are obtained.

The viscosity of the solvent to be used in the invention is not particularly limited. However, the viscosity at a solvent temperature of 25° C. is preferably 0.1 mPa·s or more. Moreover, the viscosity is preferably 10,000 mPa·s or less, more preferably 1,000 mPa·s or less, especially preferably 100 mPa·s or less. There are cases where when the viscosity of the solvent is not too large, the compound and the like are easy to dissolve therein and the display device is satisfactorily operated.

The aforementioned solvents can be used alone or as a mixture thereof.

Specific examples thereof include hydrocarbon solvents, fluorocarbon solvents, and silicone oils.

The hydrocarbon solvents include linear or branched aliphatic hydrocarbons, alicyclic hydrocarbons, aromatic hydrocarbons, and petroleum naphtha.

Examples of the aliphatic hydrocarbon solvents and the alicyclic hydrocarbon solvents include aliphatic hydrocarbon solvents such as n-decane, isodecane, decalin, nonane, dodecane, isododecane, tetradecane, hexadecane, and isoalkanes, and commercial products thereof include Isopar E, Isopar G, Isopar H, Isopar L, Isopar M (registered trademark, manufactured by Exxon Mobil Corporation), IP Solvent (registered trademark, manufactured by Idemitsu Petrochemical Co., Ltd.), and Soltol (manufactured by Phillips Petroleum International Ltd.).

The aromatic hydrocarbon solvents include alkylnaphthalenes and tetraline.

The petroleum naphtha solvents include Shell S.B.R., Shellsol 70, Shellsol 71 (manufactured by Shell Sekiyu Kagaku K.K.), Pegasol (manufactured by Exxon Mobil Corporation), and Hisosol (manufactured by Nippon Oil Corporation).

The fluorocarbon solvents are hydrocarbons mainly substituted with fluorine. Examples thereof include perfluoroalkanes represented by $C_nF_{2n+2}$, such as $C_7F_{16}$ and $C_8F_{18}$, and commercial products thereof include Fluorinert PF5080 and Fluorinert PF5070 (manufactured by Sumitomo 3M Ltd.).

Fluorochemical inert liquids include Fluorinert FC Series (manufactured by Sumitomo 3M Ltd.), fluorocarbons include Krytox GPL Series (registered trademark, manufactured by DuPont Japan Ltd.), chlorofluorocarbons include HCFC-141b (manufactured by Daikin Industries, Ltd.), and iodinated fluorocarbons, such as $F(CF_2)_4CH_2CH_2I$ and $F(CF_2)_6I$, include I-1420 and I-1600 (manufactured by Daikin Fine Chemical Laboratory Co., Ltd.) and the like.

Examples of the silicone oils include low-viscosity synthetic dimethylpolysiloxane, and commercial products thereof include KF96L (manufactured by Shin-Etsu Silicone) and SH200 (manufactured by Dow Corning Toray Silicone Co., Ltd.).

Preferably, the solvent contains at least one selected from the group consisting of hydrocarbon solvents, fluorocarbon solvents, and silicone oils. The content of these solvents is generally 50% by mass or more, preferably 70% by mass or more, more preferably 90% by mass or more.

In the case where the solvent is used as a mixture, when the interaction between the solvents is small as in the invention, the relative permittivity of the mixed solvent can be approximated by multiplying relative permittivity of each solvent constituting the mixed solvent by each volume fraction and summing respective products. Moreover, when the interaction between the solvents is similarly small, solubility of the mixed solvent in water can be approximated by a value obtained by multiplying solubility of each solvent constituting the mixed solvent in water by each molar fraction and summing respective products.

The ink of the invention contains a specific solvent and an azo compound and is obtained by dissolving the azo compound and other compounds, additives, and the like to be used according to need, in the solvent.

In connection with the term "dissolving", the azo compound need not have been completely dissolved in the solvent so long as the azo compound passes through a filter of about 0.1 μm and the solution is in such a state that the extinction coefficient thereof can be measured, or the solution may be in such a state that fine particles of the compound are dispersed therein.

(Azo Compound)

The azo compound of the invention has a chemical structure represented by the aforementioned general formula (I).

Specific examples of $R^1$, $R^2$, $D^1$, $A^1$, $A^2$ $D^1$, m, and X to be used in the above general formula (I) will be described in the following.

$R^1$ and $R^2$ each independently represent an arbitrary substituent. The arbitrary substituent is not particularly limited but $R^1$ and $R^2$ each independently are preferably an optionally substituted alkyl group having 1 to 20 carbon atoms from the viewpoint of solubility in solvents.

The alkyl groups represented by $R^1$ and $R^2$ which may possess a substituent include linear alkyl groups such as methyl, ethyl, propyl, butyl, pentyl, hexyl, heptyl, octyl, nonyl, decyl, and dodecyl groups; branched alkyl groups such as isopropyl, isobutyl, sec-butyl, tert-butyl, isooctyl, and isononyl groups; cyclic alkyl groups such as cyclopropyl, cyclobutyl, cyclopentyl, cyclohexyl, cyclopropylmethyl, cyclohexylmethyl, and 4-butylmethylcyclohexyl groups; and the like.

The number of carbon atoms of $R^1$ and $R^2$ is preferably 2 or more, more preferably 5 or more, particularly preferably 7 or more. Moreover, the number of carbon atoms is preferably 16 or less, more preferably 12 or less. When the number of carbon atoms falls within an appropriate range, there are cases where the compound is excellent in solubility in solvents and can have a high gram extinction coefficient.

Furthermore, at least one of $R^1$ and $R^2$ is preferably a branched alkyl group and further, at least one thereof is preferably a branched alkyl group having 5 to 20 carbon atoms, still further preferably a branched alkyl group having 7 to 20 carbon atoms. Moreover, it is more preferable that $R^1$ and $R^2$ both are a branched alkyl group from the viewpoint of solubility.

The substituent which may be optionally possessed by the alkyl groups of $R^1$ and $R^2$ is not particularly limited. However, specific examples thereof are preferably low polar substituents from the standpoint of solubility in solvents and examples thereof include halogen atoms such as fluorine, chlorine, bromine, and iodine atoms; alkoxy groups having 1 to 20 carbon atoms, such as methoxy, ethoxy, propoxy, butoxy, isobutoxy, sec-butoxy, and tert-butoxy groups; alkoxycarbonyl groups having 2 to 20 carbon atoms, such as methoxycarbonyl, ethoxycarbonyl, and t-butoxycarbonyl groups; a cyano group; and the like.

$D^1$ represents an arbitrary substituent. The arbitrary substituent is not particularly limited as far as it is a known substituent to be used at a coupler part of an azo compound without particular limitation.

It is particularly preferable that $D^1$ is a hydrogen atom, a halogen atom, an optionally substituted alkyl group having 1 to 20 carbon atoms, an optionally substituted alkoxy group having 1 to 20 carbon atoms, an —$NHCOR^3$ group, or an —$NHSO_2R^8$ group, since the azo compound has excellent solubility in solvents and further has a high molar extinction coefficient.

Moreover, m represents an integer of 1 to 4, and when m is 2 or larger, two or more $D^1$ groups present in one molecule may be the same or different.

The alkyl group of $D^1$ which may possess a substituent has the same meaning as the alkyl group exemplified in $R^1$ of the above general formula (I) and the substituent which may be possessed also has the same meaning.

As the alkyl group of $D^1$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The alkoxy group of $D^1$ which may possess a substituent specifically includes linear alkoxy groups such as methoxy, ethoxy, propoxy, butoxy, pentyloxy, hexyloxy, heptyloxy, octyloxy, nonyloxy, decyloxy, phenoxy, naphthyloxy, dodecanoxy, methoxymethyl methoxyethyl, methoxybutyl, ethoxymethyl, ethoxyethyl, ethoxybutyl, allyloxy, 2,2,2-trifluoromethoxy, and trifluoroethoxy groups; branched alkoxy groups such as isopropoxy, isobutoxy, sec-butoxy, tert-butoxy, and isooctyloxy groups; alkoxy groups having a cyclic structure, such as cyclopropoxy, cyclopentyloxy, cyclohexyloxy, cyclopropylmethyloxy, phenoxy, 4-butylphenoxy, 4-butylcyclohexyloxy, 3-{2-(2-ethylhexyloxy)ethoxy}phenoxy, benzyloxy, and 1-naphthyloxy groups; and the like.

As the alkoxy group of $D^1$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

Moreover, the substituent which may be optionally possessed by the alkoxy group of $D^1$ is not particularly limited. However, specific examples thereof include halogen atoms, alkoxy groups having 1 to 20 carbon atoms, carbonyl groups having 1 to 20 carbon atoms, such as formyl, acetyl, benzoyl, carbazoyl, and phenylcarbonyl groups, and the like.

$R^3$ and $R^8$ each independently represent an optionally substituted alkyl group having 1 to 20 carbon atoms, an optionally substituted aryl group having 6 to 20 carbon atoms, or an optionally substituted heteroaryl group having 2 to 20 carbon atoms.

The alkyl group of each of $R^3$ and $R^8$ has the same meaning as the alkyl group exemplified in $R^1$ of the above general formula (I) and each substituent which may be possessed also has the same meaning. As the alkyl group of $R^3$ and $R^8$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The alkoxy group of each of $R^3$ and $R^8$ has the same meaning as the alkoxy group exemplified in $D^1$ of the above general formula (I) and each substituent which may be possessed also has the same meaning. As the alkoxy group of $R^3$ and $R^8$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The aryl group of each of $R^3$ and $R^8$ is a group obtained by removing one hydrogen atom from a monocycle or a condensed ring obtained by condensing 2 to 4 rings of the monocycles. Specific examples thereof include groups from a benzene ring, a naphthalene ring, an anthrathene ring, a phenanthrene ring, a perylene ring, a tetracene ring, a pyrene ring, a benzpyrene ring, a chrysene ring, a triphenylene ring, an acenaphthene ring, a fluoranthene ring, a fluorene ring, and the like.

The heteroaryl group of each of $R^3$ and $R^8$ is a group obtained by removing one hydrogen atom from a monocycle or a condensed ring obtained by condensing 2 to 4 rings of the monocycles. Specific examples thereof include groups from a furan ring, a benzofuran ring, a thiophene ring, a benzothiophene ring, a pyrrole ring, a pyrazole ring, an imidazole ring, an oxadiazole ring, an indole ring, a carbazole ring, a pyrroloimidazole ring, a pyrrolopyrazole ring, a pyrrolopyrrole ring, a thienopyrrole ring, a thienothiophene ring, a furopyrrole ring, a furofuran ring, a thienofuran ring, a benzoisooxazole ring, a benzoisothiazole ring, a benzoimidazole ring, a pyridine ring, a pyradine ring, a pyridazine ring, a pyrimidine ring, a triazine ring, a quinoline ring, an isoquinoline ring, a shinorine ring, a quinoxaline ring, a phenanthridine ring, a benzoimidazole ring, a pyrimidine ring, a quinazoline ring, a quinazolinone ring, an azulene ring, and the like.

The substituent which may be possessed by the aryl and heteroaryl groups of $R^3$ is not particularly limited. However, specific examples include halogen atoms, alkyl groups having 1 to 20 carbon atoms, alkoxy groups having 1 to 20 carbon atoms, alkoxycarbonyl groups having 1 to 20 carbon atoms, and the like.

$A^1$ represents an arbitrary substituent. The arbitrary substituent is not particularly limited but it is preferable that $A^1$ is a hydrogen atom, a halogen atom, a cyano group, an optionally substituted alkyl group having 1 to 20 carbon atoms, an optionally substituted aryl group having 6 to 20 carbon atoms, an optionally substituted heteroaryl group having 2 to 20 carbon atoms, an optionally substituted alkoxy group having 1 to 20 carbon atoms, or a —COOR$^4$ group, since the azo compound has excellent solubility in solvents and further has a high molar extinction coefficient.

The alkyl group of $A^1$ has the same meaning as the alkyl group exemplified in $R^1$ of the above general formula (I) and the substituent which may be possessed also has the same meaning. As the alkyl group of $A^1$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The alkoxy group of $A^1$ has the same meaning as the alkoxy group exemplified in $D^1$ of the above general formula (I) and the substituent which may be possessed also has the same meaning. As the alkoxy group of $A^1$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The aryl group of $A^1$ has the same meaning as the aryl group exemplified in $R^3$ of the above general formula (I) and the substituent which may be possessed also has the same meaning as the aryl group exemplified in $R^3$ of the above general formula (I). As the aryl group of $A^1$, for the reason of high solubility in solvents, an optionally substituted phenyl group or naphthyl group is preferable. As the substituent which may be possessed by the phenyl group or the naphthyl group, for the reason of high solubility in solvents, a halogen atom, an optionally substituted alkyl group having 1 to 10 carbon atoms, or an optionally substituted alkoxy group having 1 to 10 carbon atoms is preferable.

The heteroaryl group of $A^1$ has the same meaning as the heteroaryl group exemplified in $R^3$ of the above general formula (I) and the substituent which may be possessed also has the same meaning as the heteroaryl group exemplified in $R^3$ of the above general formula (I). As the heteroaryl group of $A^1$, for the reason of high solubility in solvents, an optionally substituted thienyl group is preferable. As the substituent which may be possessed by the thienyl group, for the reason of high solubility in solvents, a halogen atom, an alkyl group having 1 to 10 carbon atoms, or an alkoxy group having 1 to 10 carbon atoms is preferable.

$R^4$ represents an optionally substituted alkyl group having 1 to 20 carbon atoms, an optionally substituted aryl group having 6 to 20 carbon atoms, or an optionally substituted heteroaryl group having 2 to 20 carbon atoms.

The alkyl group of $R^4$ specifically has the same meaning as the alkyl group exemplified in $R^1$ of the above general formula (I) and the substituent which may be possessed also has the same meaning. As the alkyl group of $R^4$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The aryl group of $R^4$ specifically has the same meaning as the aryl group exemplified in $R^3$ of the above general formula (I) and the substituent which may be possessed also has the same meaning as the aryl group exemplified in $R^3$ of the above general formula (I). The heteroaryl group of $R^4$ specifically has the same meaning as the heteroaryl group exemplified in $R^3$ of the above general formula (I) and the substituent which may be possessed also has the same meaning as the heteroaryl group exemplified in $R^3$ of the above general formula (I).

$A^2$ represents an arbitrary substituent. The arbitrary substituent is not particularly limited but includes an optionally substituted alkyl group having 1 to 20 carbon atoms, a halogen atom, an optionally substituted alkenyl group having 2 to 20 carbon atoms, an optionally substituted alkylcarbonyl group having 2 to 20 carbon atoms, an optionally substituted alkoxycarbonyl group having 2 to 20 carbon atoms, a formyl group, an $R^5OOC(NC)C=CH—$ group, an $NC(NC)C=CH—$ group, or a substituent represented by the following general formula (II):

[Chem 10]

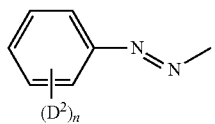

(II)

wherein $D^2$ represents an arbitrary substituent, n represents an integer of 1 to 5, and when n is 2 or larger, two or more $D^2$ groups present in one molecule may be the same or different.

The alkyl group of $A^2$ has the same meaning as the alkyl group exemplified in $R^1$ of the above general formula (I) and the substituent which may be possessed also has the same meaning. As the alkyl group of $A^2$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

In the alkenyl group of $A^2$, the position of the carbon-carbon unsaturated bond is not particularly limited and the alkenyl group may have a plurality of unsaturated bonds. Also, the group may be linear or branched and may have an arbitrary substituent. The alkenyl group includes a vinyl group, a propenyl group, a hexenyl group, and the like. Of these, the alkenyl group preferably has 3 or more carbon atoms. Moreover, the number of carbon atoms is preferably 16 or less, more preferably 12 or less. When the number of carbon atoms falls within an appropriate range, there are cases where the compound is excellent in solubility in solvents and can have a high gram extinction coefficient.

The alkyl group contained in the alkylcarbonyl group of $A^2$ includes those having the same meaning as the alkyl group exemplified in $R^1$ of the above general formula (I) and the number of carbon atoms of the alkyl group is preferably 18 or less, more preferably 16 or less.

The alkoxy group contained in the alkylcarbonyl group of $A^2$ includes those having the same meaning as the alkoxy group exemplified in $D^1$ of the above general formula (I) and the number of carbon atoms of the alkoxy group is preferably 18 or less, more preferably 16 or less.

When the number of carbon atoms of $A^2$ falls within an appropriate range, there are cases where the compound is excellent in solubility in solvents and can have a high gram extinction coefficient.

The substituent which may be possessed by the alkylcarbonyl group of $A^2$ is not particularly limited but specific examples include alkoxy groups having 1 to 20 carbon atoms. The substituent which may be possessed by the alkoxycarbonyl group of $A^2$ is not particularly limited but specific examples include alkyl groups having 1 to 20 carbon atoms. The substituent which may be possessed by the alkenyl group of $A^2$ is not particularly limited but specific examples include alkyl groups having 1 to 20 carbon atoms, alkoxy groups having 1 to 20 carbon atoms, and alkoxycarbonyl groups having 2 to 20 carbon atoms.

$R^5$ represents an optionally substituted alkyl group having 1 to 20 carbon atoms, an optionally substituted aryl group having 6 to 20 carbon atoms, or an optionally substituted heteroaryl group having 2 to 20 carbon atoms.

The alkyl group of $R^5$ specifically has the same meaning as the alkyl group exemplified in $R^1$ of the above general formula (I) and the substituent which may be possessed also has the same meaning. As the alkyl group of $R^5$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The aryl group of $R^5$ specifically has the same meaning as the aryl group exemplified in $R^3$ of the above general formula (I) and the substituent which may be possessed also has the same meaning as in the case of the aryl group exemplified in $R^3$ of the above general formula (I).

The heteroaryl group of $R^5$ specifically has the same meaning as the heteroaryl group exemplified in $R^3$ of the above general formula (I) and the substituent which may be possessed also has the same meaning as in the case of the heteroaryl group exemplified in $R^3$ of the above general formula (I).

$D^2$ represents an arbitrary substituent and is not particularly limited but specifically, $D^2$ is preferably a hydrogen atom, a halogen atom, a cyano group, an optionally substituted alkyl group having 1 to 20 carbon atoms, an optionally substituted alkoxy group having 1 to 20 carbon atoms, a $—COOR^6$ group, a $—COR^9$ group, or an $—OCOR^{10}$ group, since the azo compound has excellent solubility in solvents and further has a high molar extinction coefficient.

Moreover, n represents an integer of 1 to 5, and when n is 2 or larger, two or more $D^2$ groups present in one molecule may be the same or different.

The alkyl group of $D^2$ has the same meaning as the alkyl group exemplified in $R^1$ of the above general formula (I) and the substituent which may be possessed also has the same meaning. As the alkyl group of $D^2$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The alkoxy group of $D^2$ has the same meaning as the alkyl group exemplified in $D^1$ of the above general formula (I) and the substituent which may be possessed also has the same meaning. As the alkoxy group of $D^2$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

$R^6$, $R^9$, and $R^{10}$ each independently represent an optionally substituted alkyl group having 1 to 20 carbon atoms, an optionally substituted aryl group having 6 to 20 carbon atoms, or an optionally substituted heteroaryl group having 2 to 20 carbon atoms.

The alkyl group of each of $R^6$, $R^9$, and $R^{10}$ has the same meaning as the alkyl group exemplified in $R^1$ of the above general formula (I) and each substituent which may be possessed also has the same meaning. As the alkyl group of each of $R^6$, $R^9$, and $R^{10}$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The aryl group of each of $R^6$, $R^9$, and $R^{10}$ has the same meaning as the aryl group exemplified in $R^3$ of the above general formula (I) and each substituent which may be possessed also has the same meaning. The heteroaryl group of each of $R^6$, $R^9$, and $R^{10}$ has the same meaning as the heteroaryl group exemplified in $R^3$ of the above general formula (I) and each substituent which may be possessed also has the same meaning.

When the number of carbon atoms of each group falls within an appropriate range, there are cases where the molecular weight does not become exceedingly large and the gram extinction coefficient does not get worse.

X represents a nitrogen atom or an optionally substituted methine group. The substituent which may be possessed by the methine group is not particularly limited but is preferably a halogen atom, a cyano group, or a —COOR$^7$ group for obtaining a high solubility in solvents and a high molar extinction coefficient.

$R^7$ represents an optionally substituted alkyl group having 1 to 20 carbon atoms, an optionally substituted aryl group having 6 to 20 carbon atoms, or an optionally substituted heteroaryl group having 2 to 20 carbon atoms.

The alkyl group of $R^7$ specifically has the same meaning as the alkyl group exemplified in $R^1$ of the above general formula (I) and the substituent which may be possessed also has the same meaning. As the alkyl group of $R^7$, the number of carbon atoms is preferably 1 or more, and the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The aryl group of $R^7$ specifically has the same meaning as the aryl group exemplified in $R^3$ of the above general formula (I) and the substituent which may be possessed also has the same meaning as the aryl group exemplified in $R^3$ of the above general formula (I). The heteroaryl group of $R^7$ specifically has the same meaning as the heteroaryl group exemplified in $R^3$ of the above general formula (I) and the substituent which may be possessed also has the same meaning as the heteroaryl group exemplified in $R^3$ of the above general formula (I).

The azo compound represented by the above general formula (I) includes compounds represented by the following general formulae (X) and (XI):

[Chem 11]

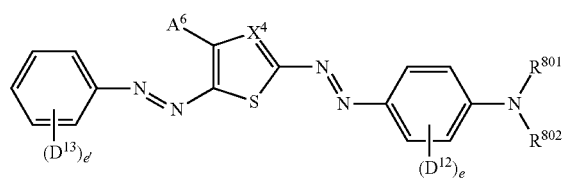

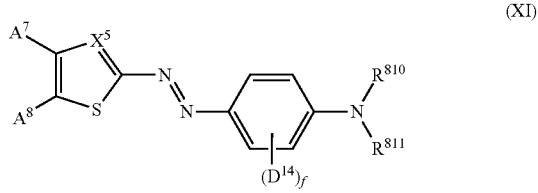

in the general formula (X), $R^{801}$ and $R^{802}$ each independently represent an optionally substituted alkyl group having 1 to 20 carbon atoms, $D^{13}$ represents a hydrogen atom, a halogen atom, an optionally substituted alkyl group having 1 to 10 carbon atoms, an optionally substituted alkoxy group having 1 to 20 carbon atoms, or a —COOR$^{803}$ group, e' represents an integer of 1 to 5, and when e' is 2 or larger, two or more $D^{13}$ groups present in one molecule may be the same or different, $R^{803}$ represents an optionally substituted alkyl group having 1 to 10 carbon atoms, $D^{12}$ represents a hydrogen atom, a halogen atom, an optionally substituted alkyl group having 1 to 10 carbon atoms, an optionally substituted alkoxy group having 1 to 10 carbon atoms, or an optionally substituted —NHCOR$^{804}$ group, e represents an integer of 1 to 4, and when e is 2 or larger, two or more $D^{12}$ groups present in one molecule may be the same or different, $R^{804}$ represents an optionally substituted alkyl group having 1 to 10 carbon atoms, an optionally substituted alkoxy group having 1 to 20 carbon atoms, or an optionally substituted aryl group having 6 to 20 carbon atoms, $X^4$ represents a nitrogen atom or a methine group which may have a halogen atom, a cyano group, or a —COOR$^{805}$ group as a substituent, $R^{805}$ represents an optionally substituted alkyl group having 1 to 10 carbon atoms, $A^6$ represents a hydrogen atom, a halogen atom, a cyano group, an optionally substituted alkyl group having 1 to 10 carbon atoms, an optionally substituted phenyl group, an optionally substituted alkoxy group having 1 to 10 carbon atoms, or a —COOR$^{806}$ group, and R$^{806}$ represents an optionally substituted alkyl group having 1 to 10 carbon atoms;

in the general formula (XI),

R$^{810o}$ and R$^{811}$ each independently represent an optionally substituted branched alkyl group having 1 to 20 carbon atoms, D$^{14}$ represents a hydrogen atom, a halogen atom, an optionally substituted alkyl group having 1 to 10 carbon atoms, an optionally substituted alkoxy group having 1 to 10 carbon atoms, or an —NHCOR$^{813}$ group, R$^{813}$ represents an optionally substituted alkyl group having 1 to 10 carbon atoms, an optionally substituted alkoxy group having 1 to 20 carbon atoms, or an optionally substituted aryl group having 6 to 20 carbon atoms, f represents an integer of 1 to 4, and when f is 2 or larger, two or more D$^{14}$ groups present in one molecule may be the same or different, A$^{7}$ represents a hydrogen atom, a halogen atom, a cyano group, an optionally substituted alkyl group having 1 to 10 carbon atoms, an optionally substituted aryl group having 6 to 20 carbon atoms, an optionally substituted alkoxy group having 1 to 10 carbon atoms, or a —COOR$^{814}$ group, R$^{814}$ represents an optionally substituted alkyl group having 1 to 10 carbon atoms, A$^{8}$ represents an optionally substituted alkyl group having 1 to 20 carbon atoms, an optionally substituted alkoxy group having 1 to 20 carbon atoms, an optionally substituted alkenyl group having 2 to 20 carbon atoms, an optionally substituted alkylcarbonyl group having 2 to 20 carbon atoms, an optionally substituted alkoxycarbonyl group having 2 to 20 carbon atoms, a formyl group, an R$^{815}$OOC(NC)C=CH— group, an NC(NC)C=CH— group, or a group represented by the following general formula (XII):

[Chem 12]

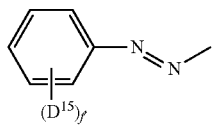
(XII)

R$^{815}$ represents an optionally substituted alkyl group having 1 to 20 carbon atoms, D$^{15}$ represents a hydrogen atom, a halogen atom, a cyano group, an optionally substituted alkyl group having 1 to 20 carbon atoms, an optionally substituted alkoxy group having 1 to 20 carbon atoms, or a —COOR$^{816}$ group, f' represents an integer of 1 to 5, and when f' is 2 or larger, two or more D$^{15}$ groups present in one molecule may be the same or different, R$^{816}$ represents an optionally substituted alkyl group having 1 to 10 carbon atoms, X$^{5}$ represents a nitrogen atom or a methine group which may have a halogen atom, a cyano group, or a —COOR$^{817}$ group as a substituent, and R$^{817}$ represents an optionally substituted alkyl group having 1 to 10 carbon atoms.

In the compound represented by the general formula (X), R$^{801}$ and R$^{802}$ represent an optionally substituted alkyl group having 1 to 20 carbon atoms. R$^{801}$ and R$^{802}$ preferably have 4 or more carbon atoms and is more preferably an alkyl group having 5 or more carbon atoms. Moreover, the number of carbon atoms is preferably 16 or less, and is more preferably 12 or less.

When the number of carbon atoms of the alkyl group is too large, there are cases where the gram extinction coefficient gets worse since the molecular weight becomes too large. Moreover, at least one of R$^{801}$ and R$^{802}$ is preferably a branched alkyl group and further, at least one thereof is preferably a branched alkyl group having 5 to 20 carbon atoms. Furthermore, it is more preferable that both of R$^{801}$ and R$^{802}$ are a branched alkyl group.

D$^{13}$ represents a hydrogen atom, a halogen atom, an optionally substituted alkyl group having 1 to 10 carbon atoms, an optionally substituted alkoxy group having 1 to 20 carbon atoms, or a —COOR$^{803}$ group. Moreover, e' represents an integer of 1 to 5, and when e' is 2 or larger, two or more D$^{13}$ groups present in one molecule may be the same or different.

In the case where D$^{13}$ is an alkyl group, the number of carbon atoms is preferably 2 or more and is preferably 8 or less, more preferably 6 or less.

In the case where D$^{13}$ is an alkoxy group, the number of carbon atoms is preferably 4 or more, more preferably 5 or more. Moreover, the number of carbon atoms is preferably 16 or less, more preferably 12 or less.

In the case where D$^{13}$ is a —COOR$^{803}$ group, R$^{803}$ represents an optionally substituted alkyl group having 1 to 10 carbon atoms. The number of carbon atoms of the alkyl group of R$^{803}$ is preferably 2 or more and is preferably 8 or less, more preferably 6 or less.

When the number of carbon atoms falls within an appropriate range, there are cases where the compound is excellent in solubility in solvents and can have a high gram extinction coefficient.

D$^{12}$ represents a hydrogen atom, a halogen atom, an optionally substituted alkyl group having 1 to 10 carbon atoms, an optionally substituted alkoxy group having 1 to 10 carbon atoms, or an optionally substituted —NHCOR$^{804}$ group.

Moreover, e represents an integer of 1 to 4, and when e is 2 or larger, two or more D$^{12}$ groups present in one molecule may be the same or different.

The number of carbon atoms of the alkyl group and the alkoxy group is preferably 1 or more and is preferably 8 or less, more preferably 6 or less.

R$^{804}$ represents an optionally substituted alkyl group having 1 to 10 carbon atoms, an optionally substituted alkoxy group having 1 to 20 carbon atoms, or an optionally substituted aryl group having 6 to 20 carbon atoms. The number of carbon atoms of each of the alkyl and alkoxy groups of R$^{804}$ is preferably 1 or more and is preferably 8 or less, more preferably 6 or less.

Moreover, the number of carbon atoms of the aryl group of R$^{804}$ is preferably 6 or more, more preferably 10 or more. Also, the number of carbon atoms is preferably 16 or less. When the number of carbon atoms falls within an appropriate range, there are cases where the compound is excellent in solubility in solvents and can have a high gram extinction coefficient.

X$^{4}$ represents a nitrogen atom or a methine group which may have a halogen atom, a cyano group, or a —COOR$^{805}$ group as a substituent.

In the case where the methine group has a —COOR$^{805}$ group, R$^{805}$ represents an optionally substituted alkyl group having 1 to 10 carbon atoms. The number of carbon atoms of the alkyl group of R$^{805}$ is preferably 1 or more and is preferably 8 or less, more preferably 6 or less.

When the number of carbon atoms falls within an appropriate range, there are cases where the compound is excellent in solubility in solvents and can have a high gram extinction coefficient.

$A^6$ represents a hydrogen atom, a halogen atom, a cyano group, an optionally substituted alkyl group having 1 to 10 carbon atoms, an optionally substituted phenyl group, an optionally substituted alkoxy group having 1 to 10 carbon atoms, or a —$COOR^{806}$ group.

Of the alkyl groups and alkoxy groups having 1 to 10 carbon atoms, the number of carbon atoms is preferably 1 or more and is preferably 8 or less, more preferably 6 or less.

$R^{806}$ represents a hydrogen atom or an optionally substituted alkyl group having 1 to 10 carbon atoms. The number of carbon atoms of the alkyl group of $R^{806}$ is preferably 1 or more and is preferably 8 or less, more preferably 6 or less.

When the number of carbon atoms falls within an appropriate range, there are cases where the compound is excellent in solubility in solvents and can have a high gram extinction coefficient.

Incidentally, specific examples of the alkyl group in the above general formula (X) include linear alkyl groups such as methyl, ethyl, propyl, butyl, pentyl, hexyl, heptyl, octyl, nonyl, decyl, and dodecyl groups; branched alkyl groups such as isopropyl, isobutyl, sec-butyl, tert-butyl, isooctyl, and isononyl groups; cyclic alkyl groups such as cyclopropyl, cyclopentyl, cyclohexyl, and cyclopropylmethyl groups; and the like.

Moreover, the alkyl group in the above general formula (X) may have an arbitrary substituent. The arbitrary substituent is preferably a low polar substituent from the standpoint of solubility in solvents and examples thereof include halogen atoms such as fluorine, chlorine, bromine, and iodine atoms; alkoxy groups having 1 to 10 carbon atoms, such as methoxy, ethoxy, propoxy, butoxy, isobutoxy, sec-butoxy, and tert-butoxy groups; and the like.

$R^{810}$ and $R^{811}$ in the general formula (XI) represent an optionally substituted alkyl group having 1 to 20 carbon atoms. The alkyl group of $R^{810}$ and $R^{811}$ which may have a substituent includes methyl, ethyl, propyl, butyl, pentyl, hexyl, heptyl, octyl, nonyl, decyl, and dodecyl groups; branched alkyl groups such as isopropyl, isobutyl, sec-butyl, tert-butyl, isooctyl, and isononyl groups; cyclic alkyl groups such as cyclopropyl, cyclobutyl, cyclopentyl, cyclohexyl, cyclopropylmethyl, cyclohexylmethyl, and 4-butylmethylcyclohexyl groups; and the like.

$R^{810}$ and $R^{811}$ have preferably 4 or more carbon atoms, more preferably 5 or more carbon atoms. Moreover, the number of carbon atoms is preferably 16 or less and more preferably 12 or less. When the number of carbon atoms falls within an appropriate range, there are cases where the compound is excellent in solubility in solvents and can have a high gram extinction coefficient.

Moreover, at least one of $R^{810}$ and $R^{811}$ is preferably a branched alkyl group and further, at least one thereof is preferably a branched alkyl group having 5 to 20 carbon atoms. Furthermore, it is more preferable that both of $R^{810}$ and $R^{811}$ are a branched alkyl group from the standpoint of solubility.

Specific examples of the substituent which may be optionally possessed by the alkyl groups of each of $R^{810}$ and $R^{811}$ are preferably low polar substituents from the standpoint of solubility in solvents, and examples thereof include halogen atoms such as fluorine, chlorine, bromine, and iodine atoms; alkoxy groups having 1 to 20 carbon atoms, such as methoxy, ethoxy, propoxy, butoxy, isobutoxy, sec-butoxy, and tert-butoxy groups; alkoxycarbonyl groups having 2 to 20 carbon atoms, such as methoxycarbonyl, ethoxycarbonyl, and t-utoxycarbonyl groups; a cyano group; and the like.

$D^{14}$ represents a hydrogen atom, a halogen atom, an optionally substituted alkyl group having 1 to 10 carbon atoms, an optionally substituted alkoxy group having 1 to 10 carbon atoms, or an —$NHCOR^{813}$ group.

Moreover, f represents an integer of 1 to 4, and when f is 2 or larger, two or more $D^{14}$ groups present in one molecule may be the same or different.

The alkyl group of $D^{14}$ which may have a substituent has the same meaning as the alkyl group having 1 to 10 carbon atoms, among the alkyl groups having 1 to 20 carbon atoms exemplified in $R^{810}$.

The alkoxy group of $D^{14}$ which may have the substituent includes linear alkoxy groups such as methoxy, ethoxy, propoxy, butoxy, pentyloxy, hexyloxy, heptyloxy, octyloxy, nonyloxy, and decyloxy groups; branched alkoxy groups such as isopropoxy, isobutoxy, sec-butoxy, tert-butoxy, and isooctyloxy groups; alkoxy groups having a cycloalkane structure, such as cyclopropoxy, cyclopentyloxy, cyclohexyloxy, and cyclopropylmethyloxy groups; and the like.

The number of carbon atoms of each of the alkyl and alkoxy groups of $D^{14}$ is preferably 8 or less and is more preferably 6 or less since it is advantageous from the standpoint of the gram extinction coefficient.

Moreover, the substituent which may be possessed by $D^{14}$ is preferably a low polar substituent from the standpoint of solubility in solvents.

Specific examples of the substituent which may be possessed by the alkyl group of $D^{14}$ include halogen atoms, alkoxy groups having 1 to 10 carbon atoms, alkoxycarbonyl groups having 3 to 10 carbon atoms, and the like.

Specific examples of the substituent which may be possessed by the alkoxy group of $D^{14}$ include halogen atoms, alkyl groups having 1 to 10 carbon atoms, carbonyl groups having 1 to 10 carbon atoms such as formyl, acetyl, benzoyl, carbazoyl, and phenylcarbonyl group, and the like.

$R^{813}$ represents an optionally substituted alkyl group having 1 to 10 carbon atoms, an optionally substituted alkoxy group having 1 to 20 carbon atoms, or an optionally substituted aryl group having 6 to 20 carbon atoms.

The alkyl group of $R^{813}$ has the same meaning as the alkyl group exemplified in $D^{14}$. The number of carbon atoms of alkyl group of $R^{813}$ is preferably 9 or less and is more preferably 8 or less. The alkoxy group of $R^{813}$ has the same meaning as the alkoxy group exemplified in $A^8$ to be mentioned later.

The aryl group of $R^{813}$ is a group obtained by removing one hydrogen atom from a monocycle of 5- or 6-membered ring or a condensed ring obtained by condensing 2 to 4 rings of the monocycles. Specific examples thereof include groups of aromatic hydrocarbon ring groups or aromatic heterocyclic groups such as phenyl, tolyl, xylyl, mesityl, naphthyl, thienyl, and pyridyl groups. The number of carbon atoms is preferably 10 or more and the number of carbon atoms is preferably 16 or less, more preferably 12 or less.

Moreover, the substituent which may be possessed by each of the alkyl and alkoxy groups of $R^{813}$ has the same meaning as the substituent which may be possessed by each of the alkyl and alkoxy groups exemplified in $D^{14}$.

The substituent which may be possessed by the aryl group of $R^{813}$ includes halogen atoms, alkyl groups having 1 to 20 carbon atoms, alkoxy groups having 1 to 10 carbon atoms, alkoxycarbonyl groups having 2 to 10 carbon atoms, and the like.

When the number of carbon atoms of $R^{813}$ falls within an appropriate range, there are cases where the compound is excellent in solubility in solvents and can have a high gram extinction coefficient.

$A^7$ represents a hydrogen atom, a halogen atom, a cyano group, an optionally substituted alkyl group having 1 to 10 carbon atoms, an optionally substituted aryl group having 6 to 20 carbon atoms, an optionally substituted alkoxy group having 1 to 10 carbon atoms, or a —COOR$^{814}$ group.

The alkyl group and alkoxy group of $A^7$ have the same meaning as the alkyl group and alkoxy group exemplified in $D^{14}$. In the alkyl group and alkoxy group having 1 to 10 carbon atoms, the number of carbon atoms is preferably 8 or less and is more preferably 6 or less.

The aryl group of $A^7$ has the same meaning as the aryl group exemplified in $R^{813}$. Of the group, it is preferably an optionally substituted phenyl group.

$R^{814}$ represents an optionally substituted alkyl group having 1 to 10 carbon atoms. The alkyl group of $R^{814}$ has the same meaning as the alkyl group exemplified in $D^{14}$. Of the group, the number of carbon atoms is preferably 8 or less and is more preferably 6 or less. When the number of carbon atoms of each of $A^7$ and $R^{814}$ falls within an appropriate range, there are cases where the compound is excellent in solubility in solvents and can have a high gram extinction coefficient.

Moreover, the substituent which may be possessed by each of the alkyl group of $A^7$ and the alkyl group of $R^{814}$ has the same meaning as the substituent which may be possessed by the alkyl group exemplified in $D^{14}$. The substituent which may be possessed by the alkoxy group of $A^7$ has the same meaning as the substituent which may be possessed by the alkoxy group exemplified in $D^{14}$, and the substituent which may be possessed by the aryl group of $A^7$ has the same meaning as the substituent which may be possessed by the aryl group exemplified in $R^{813}$.

$A^8$ represents an optionally substituted alkyl group having 1 to 20 carbon atoms, an optionally substituted alkoxy group having 1 to 20 carbon atoms, an optionally substituted alkenyl group having 2 to 20 carbon atoms, an optionally substituted alkylcarbonyl group having 2 to 20 carbon atoms, an optionally substituted alkoxycarbonyl group having 2 to 20 carbon atoms, a formyl group, an $R^{815}$OOC(NC)C═CH—group, an NC(NC)C═CH—group, or a group represented by the following general formula (XII).

[Chem 13]

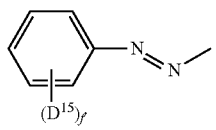

(XII)

The alkyl group of $A^8$ has the same meaning as the alkyl group exemplified in $R^{810}$. The number of carbon atoms is preferably 3 or more. Moreover, the number of carbon atoms is preferably 18 or less and is more preferably 16 or less.

In the alkenyl group of $A^8$, the position of the carbon-carbon unsaturated bond is not particularly limited and the alkenyl group may have a plurality of unsaturated bonds. Also, the group may be linear or branched and may have an arbitrary substituent. The alkenyl group includes a vinyl group, a propenyl group, a hexenyl group, and the like. Of these, the alkenyl group preferably has 3 or more carbon atoms. Moreover, the number of carbon atoms is preferably 16 or less, more preferably 12 or less.

The alkoxy group of $A^8$ includes linear, branched, and cyclic alkoxy groups having 1 to 20 carbon atoms, such as phenoxy, naphthyloxy, dodecanoxy, methoxymethyl methoxyethyl, methoxybutyl, ethoxybutyl, ethoxyethyl, and ethoxybutyl in addition to those having the same meaning as the alkoxy group exemplified in $D^{14}$; and the like Of these, the alkoxy group preferably has 3 or more carbon atoms. Moreover, the number of carbon atoms is preferably 16 or less, more preferably 12 or less.

The alkoxy group contained in the alkoxycarbonyl group of $A^8$ includes those having the same meaning as the alkoxy group exemplified in $A^8$. The number of carbon atoms is preferably 1 or more. Moreover, the number of carbon atoms is preferably 18 or less and is more preferably 16 or less.

When the number of carbon atoms of $A^8$ falls within an appropriate range, there are cases where the compound is excellent in solubility in solvents and can have a high gram extinction coefficient.

$R^{815}$ represents an optionally substituted alkyl group having 1 to 20 carbon atoms. The alkyl group of $A^{815}$ includes those having the same meaning as the alkyl group exemplified in $R^{810}$. The number of carbon atoms of $A^{815}$ is preferably 2 or more, more preferably 4 or more. Moreover, the number of carbon atoms is preferably 18 or less and is more preferably 16 or less. When the number of carbon atoms falls within an appropriate range, there are cases where the compound is excellent in solubility in solvents and can have a high gram extinction coefficient.

Moreover, the substituent which may be possessed by the alkyl group of each of $A^8$ and $R^{815}$ has the same meaning as the substituent which may be possessed by the alkyl group exemplified in $R^{810}$. Specific examples of the substituent which may be possessed by the alkoxy group of $A^8$ include halogen atoms, alkoxy groups having 1 to 20 carbon atoms, alkyl groups having 1 to 20 carbon atoms, carbonyl groups having 1 to 20 carbon atoms, such as formyl, acetyl, benzoyl, carbazoyl, and phenylcarbonyl groups, and the like.

Specific examples of the substituent which may be possessed by the alkylcarbonyl group of $A^8$ include alkoxy groups having 1 to 20 carbon atoms, and specific examples of the substituent which may be possessed by the alkenyl group of $A^8$ include alkyl groups having 1 to 20 carbon atoms, alkoxy groups having 1 to 20 carbon atoms, alkoxycarbonyl groups having 2 to 20 carbon atoms, and the like.

$D^{15}$ represents a hydrogen atom, a halogen atom, a cyano group, an optionally substituted alkyl group having 1 to 20 carbon atoms, an optionally substituted alkoxy group having 1 to 20 carbon atoms, or a —COOR$^{816}$ group.

Moreover, f represents an integer of 1 to 5, and when f is 2 or larger, two or more $D^{15}$ groups present in one molecule may be the same or different.

The alkyl group of $D^{15}$ includes those having the same meaning as the alkyl group exemplified in $R^{810}$. Of these, the alkyl group preferably has 3 or more carbon atoms. Moreover, the number of carbon atoms is preferably 18 or less, more preferably 16 or less.

The alkoxy group of $D^{15}$ includes those having the same meaning as the alkoxy group exemplified in $A^8$. Of these, the alkyl group preferably has 4 or more carbon atoms, more preferably 5 or more carbon atoms. Moreover, the number of carbon atoms is preferably 16 or less, more preferably 12 or less.

$R^{816}$ is an optionally substituted alkyl group having 1 to 10 carbon atoms and specifically, includes those having the same meaning as the alkyl group exemplified in $D^{14}$. Of these, the alkyl group preferably has 2 or more carbon atoms. Moreover, the number of carbon atoms is preferably 8 or less, more preferably 6 or less.

When the number of carbon atoms of each group falls within an appropriate range, there are cases where the compound is excellent in solubility in solvents and can have a high gram extinction coefficient.

Moreover, the substituent which may be possessed by the alkyl group of $D^{15}$ has the same meaning as the substituent which may be possessed by the alkyl group exemplified in $R^{810}$, and the substituent which may be possessed by the alkoxy group of $D^{15}$ has the same meaning as the substituent which may be possessed by the alkoxy group exemplified in $A^8$. The substituent which may be possessed by the alkyl group of $R^{816}$ has the same meaning as the substituent which may be possessed by the alkyl group exemplified in $D^{14}$.

$X^5$ represents a nitrogen atom or a methine group which may have a halogen atom, a cyano group, or a —$COOR^{817}$ group as a substituent.

The alkyl group having 1 to 10 carbon atoms of $R^{817}$ which may have a substituent and the substituent which may be possessed by the alkyl group have the same meaning as the alkyl group and the substituent which may be possessed by the alkyl group, which are exemplified in $D^{14}$. Of these, the number of carbon atoms is preferably 8 or less, more preferably 6 or less. When the number of carbon atoms of each group falls within an appropriate range, there are cases where the compound is excellent in solubility in solvents and can have a high gram extinction coefficient.

Specific examples of the azo compound represented by the above general formula (I) are exemplified in the following. The invention is not limited to these unless it exceeds the gist thereof.

[Chem 14]

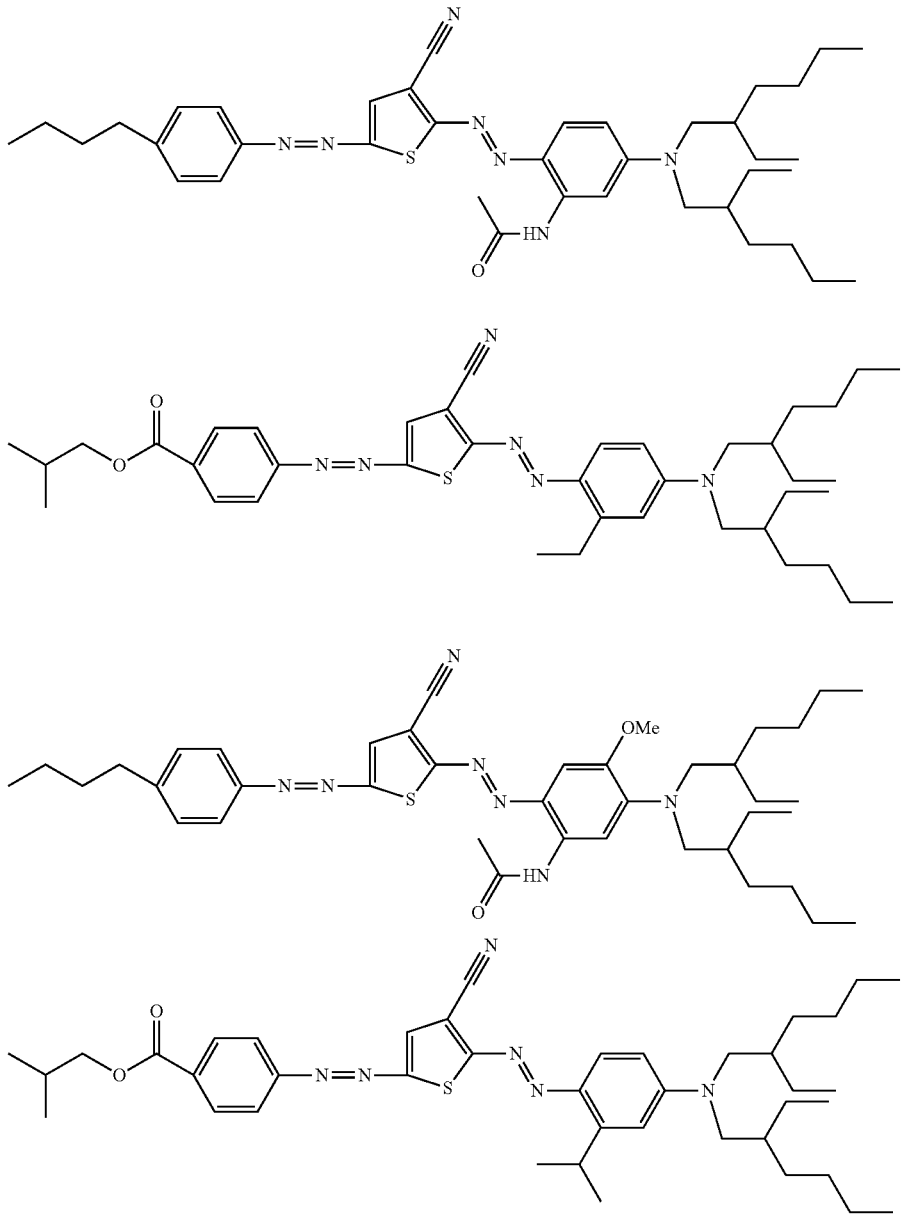

-continued
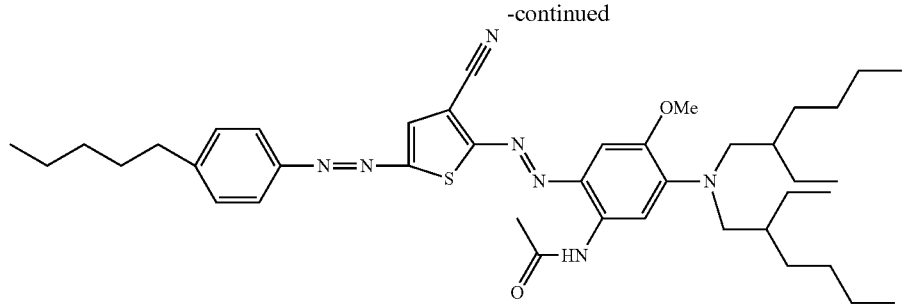
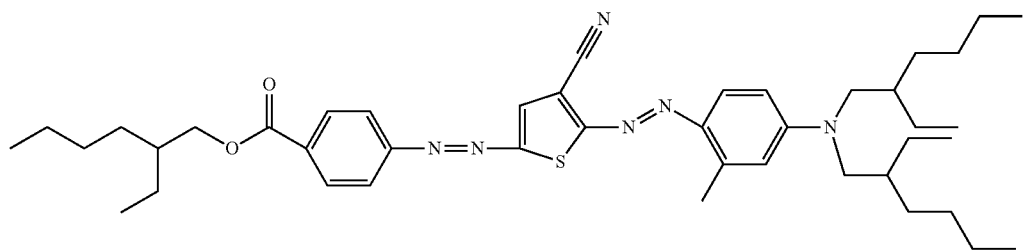
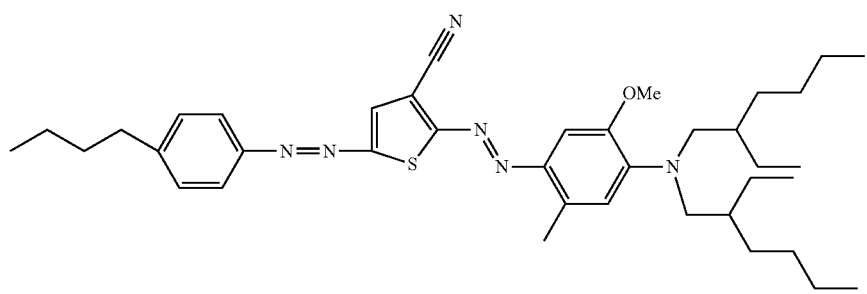
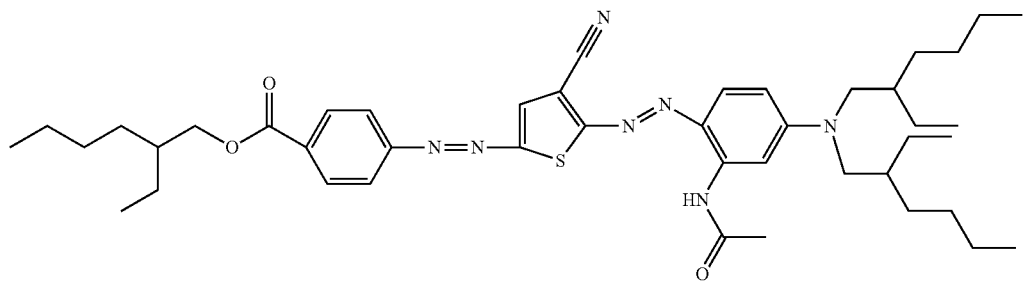
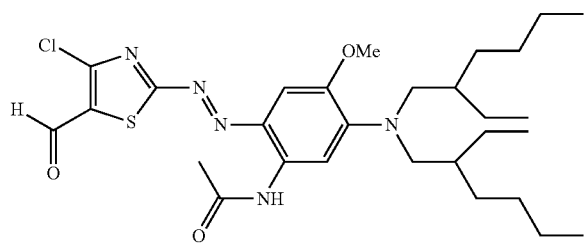
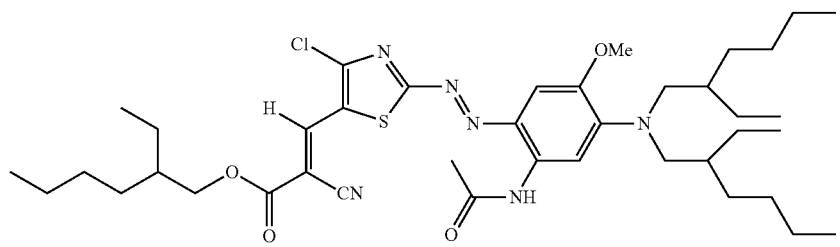

-continued
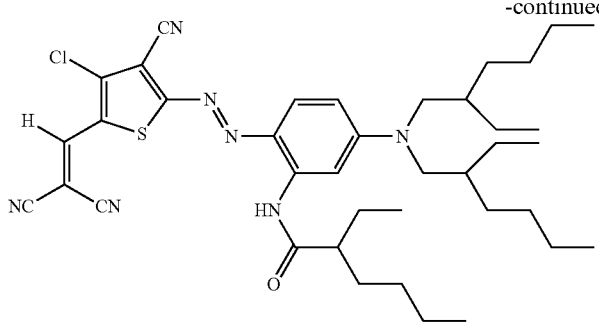
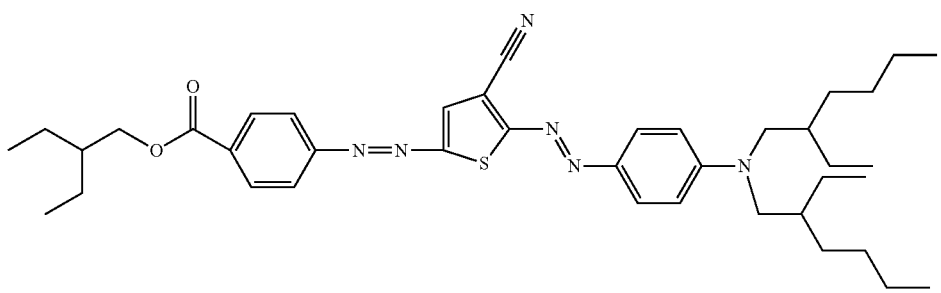
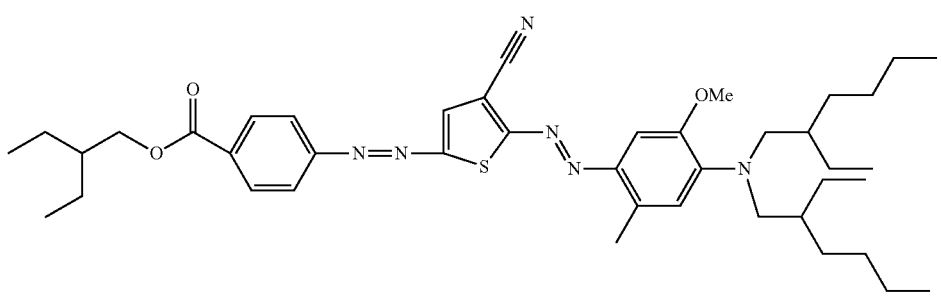
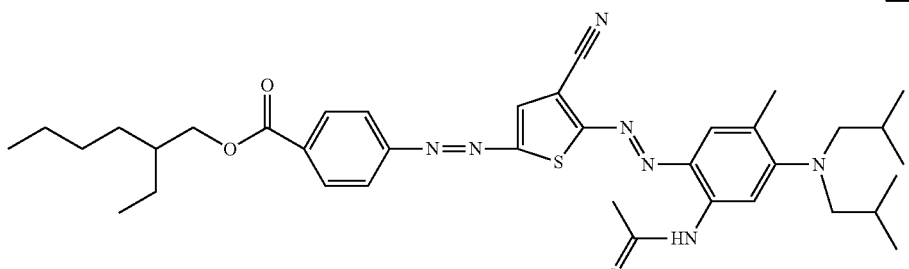
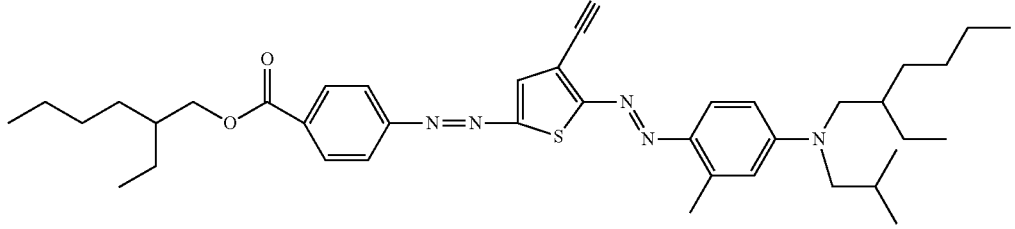
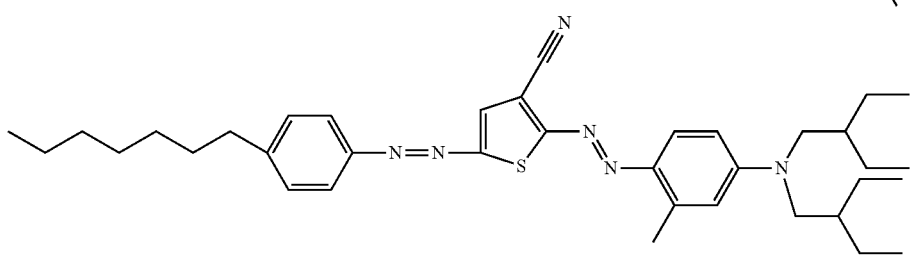

[Chem 15]
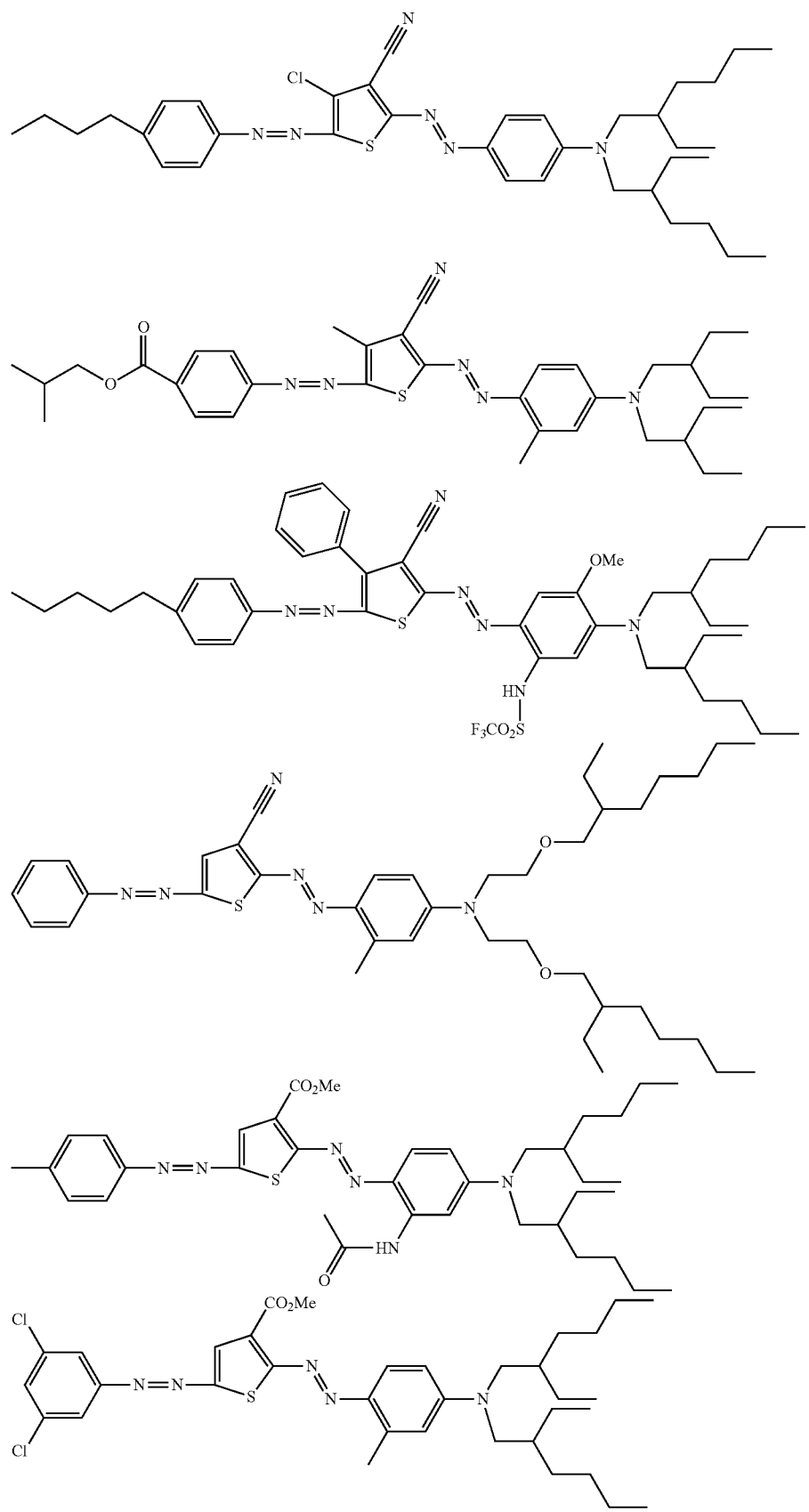

-continued
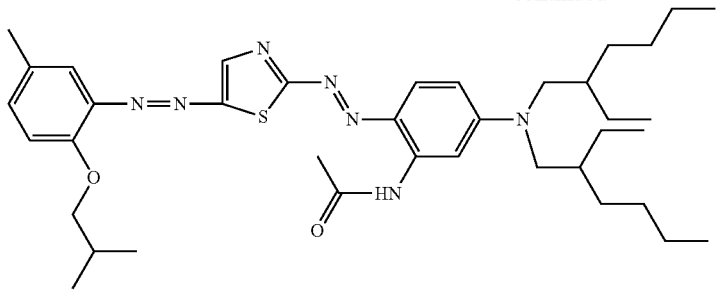
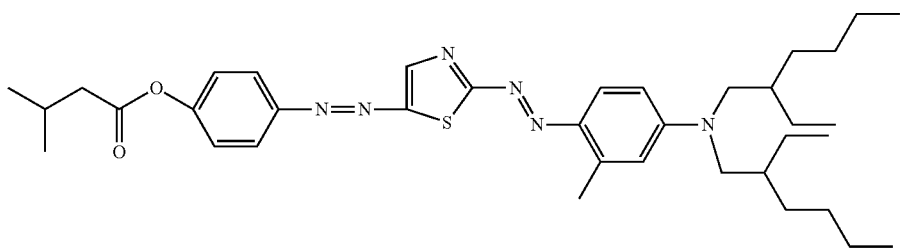
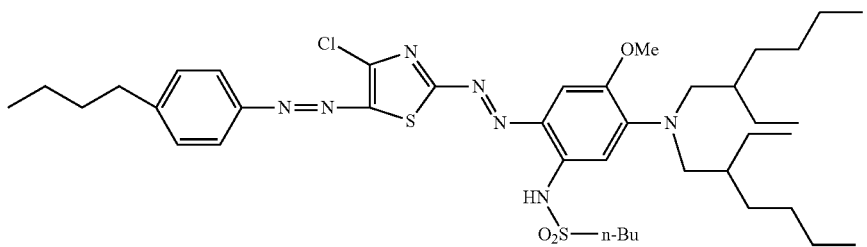
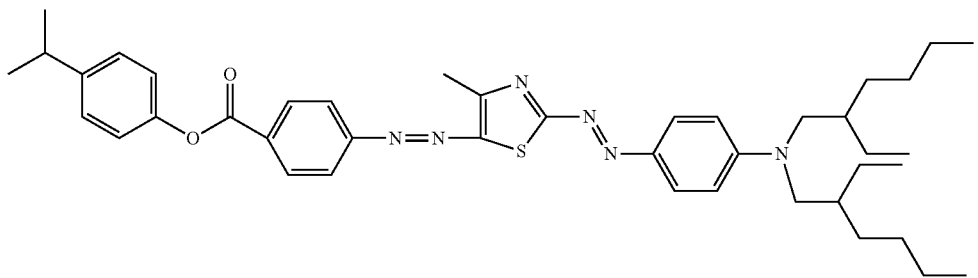
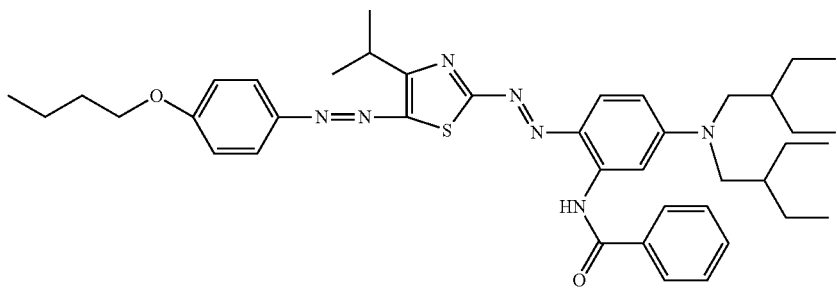
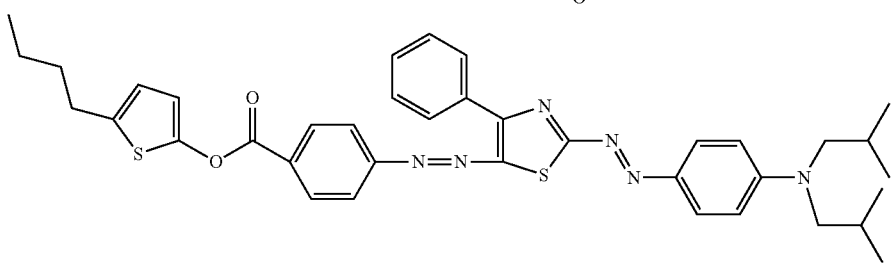

-continued
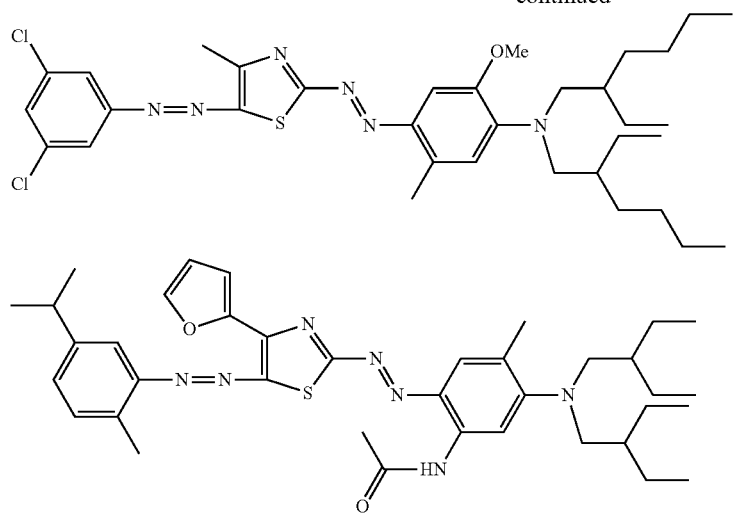
[Chem 16]
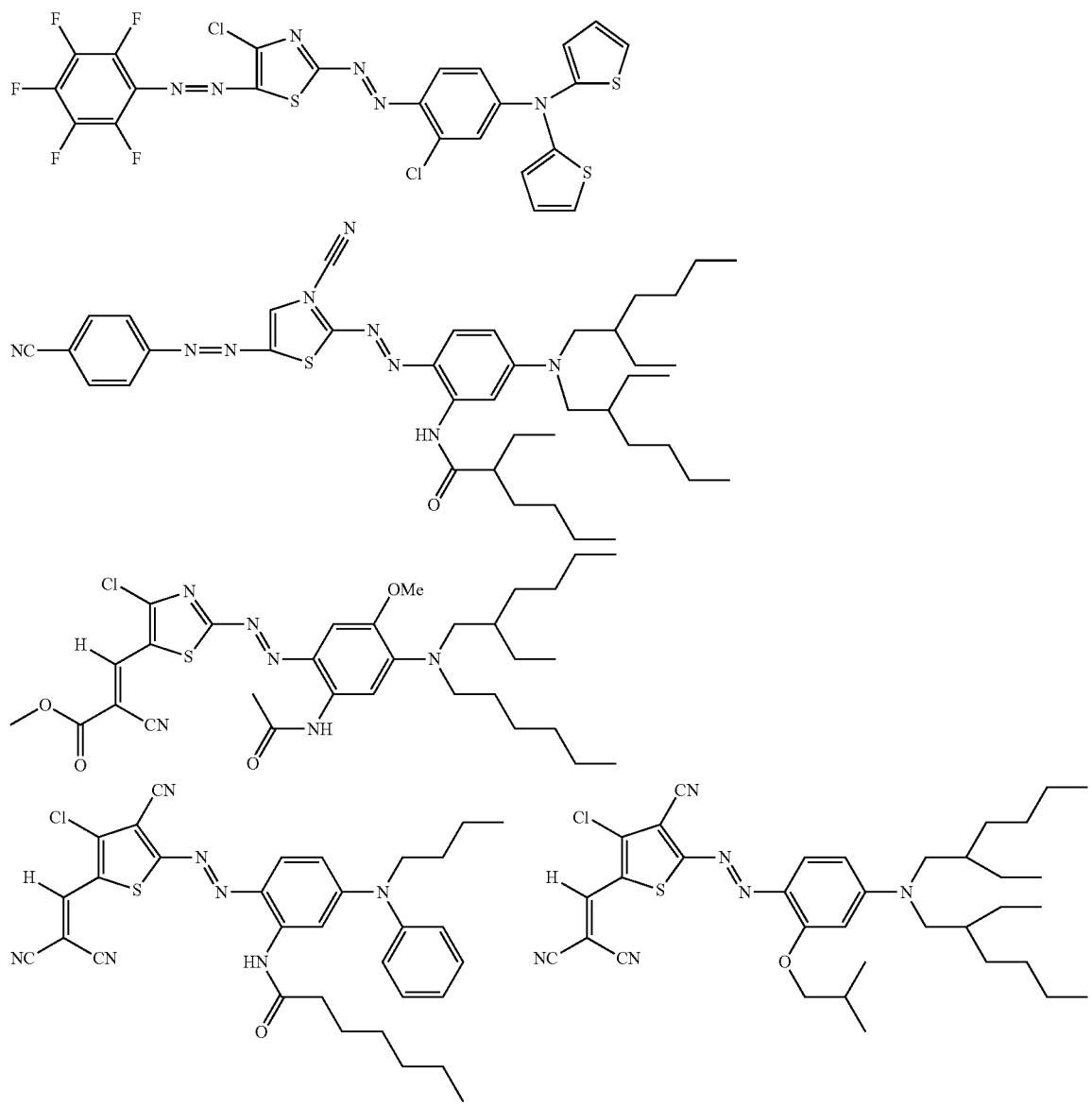

-continued
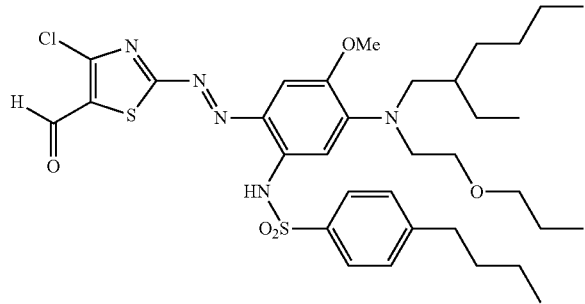
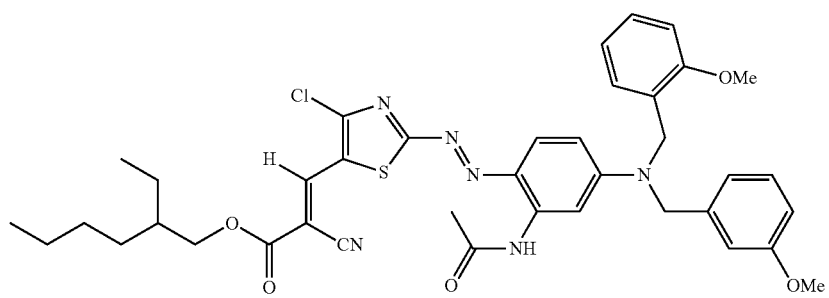
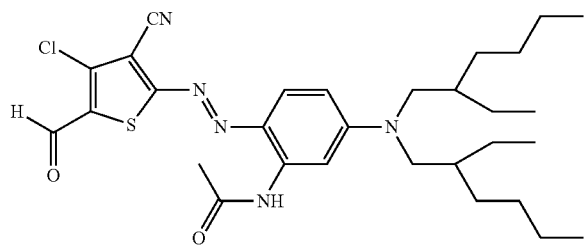
[Chem 17]
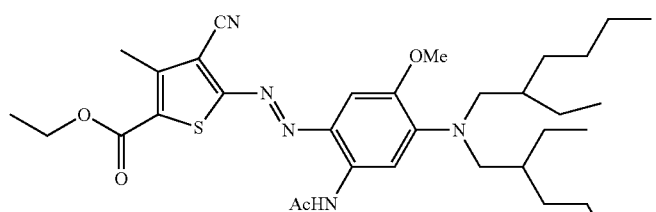
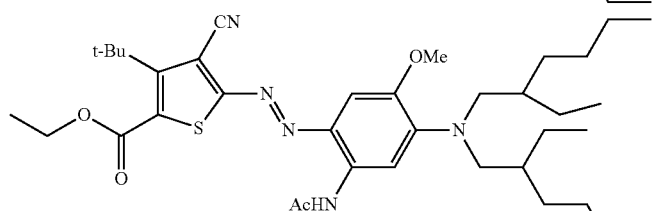
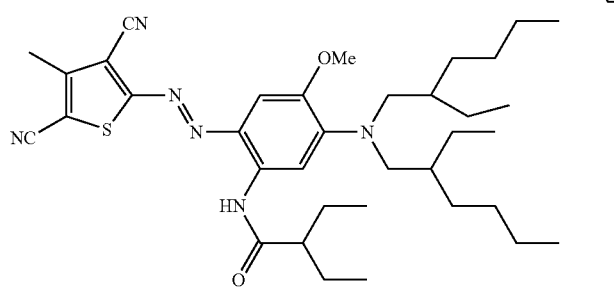

-continued
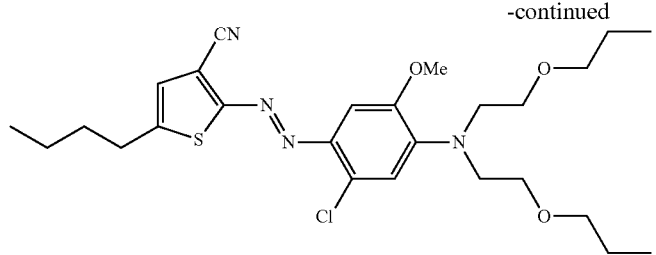
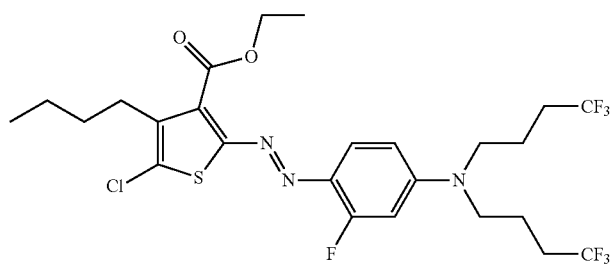
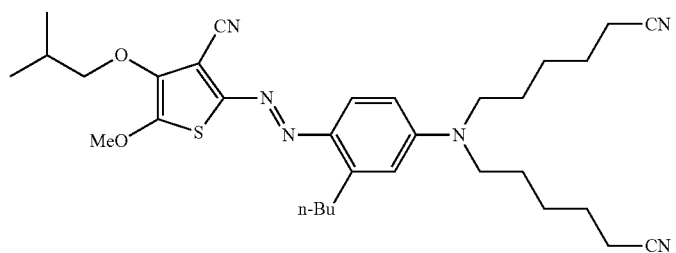
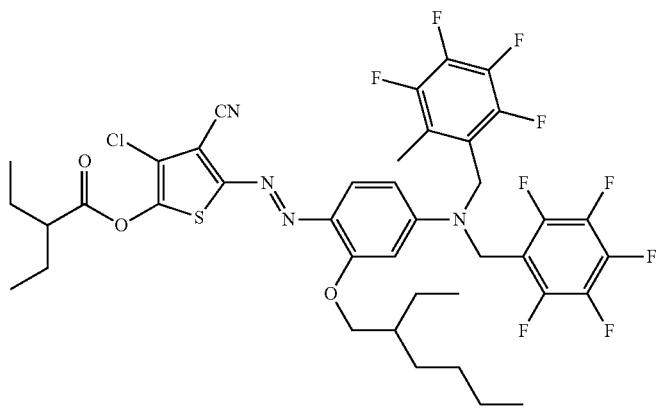
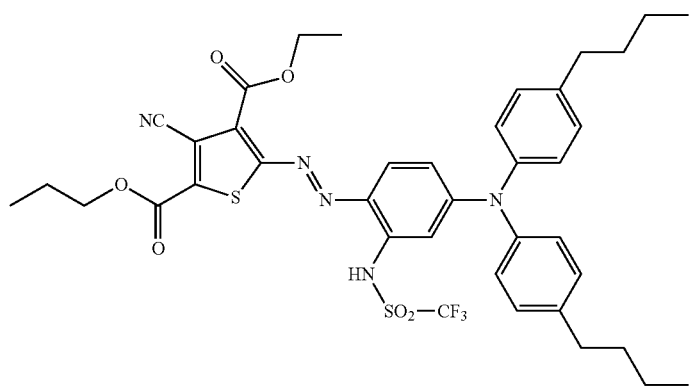

-continued
[Chem 18]
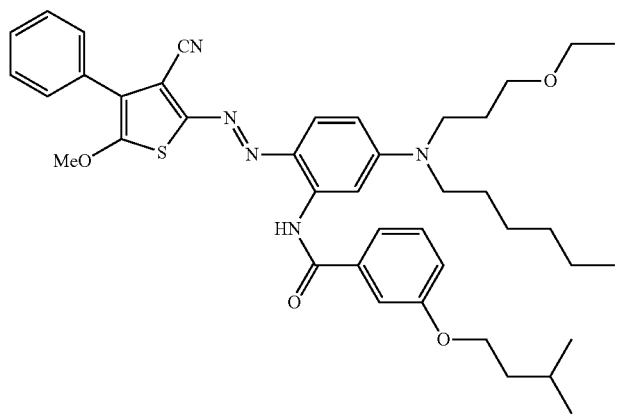
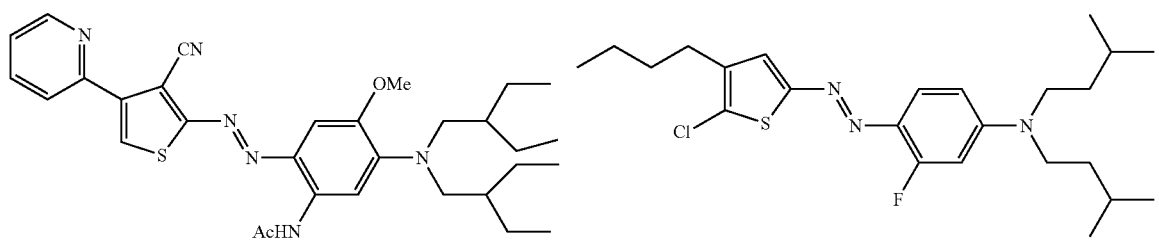
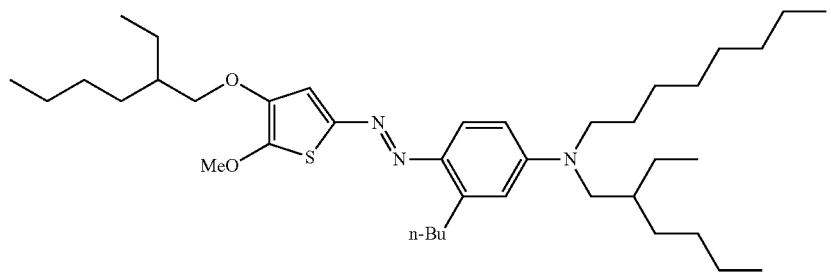
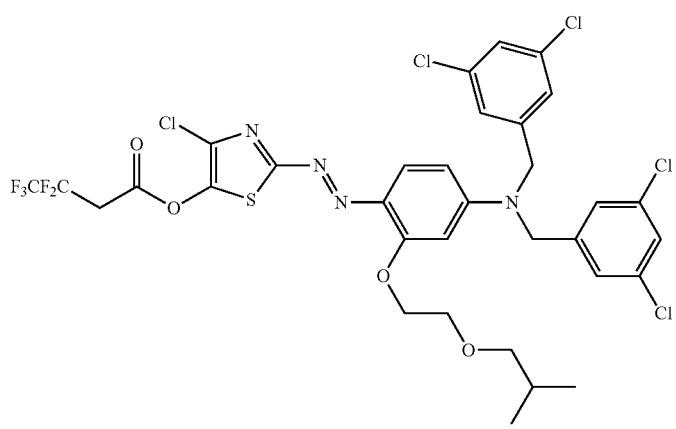

-continued

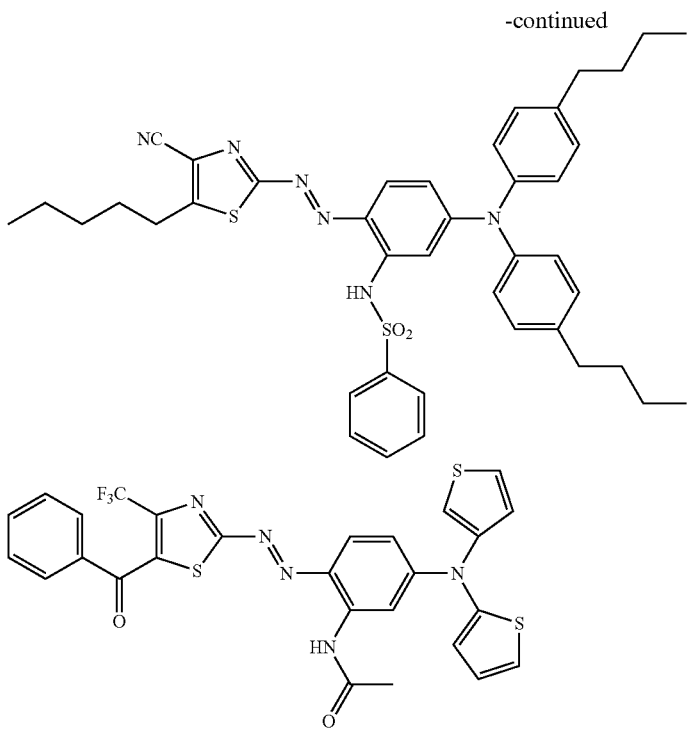

The use of the compounds represented by the following general formulae (VIII) and (IX) as azo compounds of the invention is more preferable since the solubility in solvents can be improved.

[Chem 19]

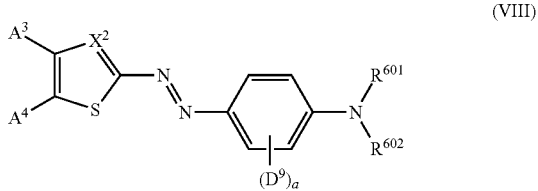

(VIII)

wherein $R^{601}$ and $R^{602}$ each independently represent an optionally substituted branched alkyl group having 7 to 20 carbon atoms, $D^9$ represents a hydrogen atom, a halogen atom, an optionally substituted alkyl group having 1 to 20 carbon atoms, an optionally substituted alkoxy group having 1 to 20 carbon atoms, an —NHCOR$^{603}$ group, or an —NHSO$_2$R$^{608}$ group, $R^{603}$ and $R^{608}$ each independently represent an optionally substituted alkyl group having 1 to 20 carbon atoms, an optionally substituted aryl group having 6 to 20 carbon atoms, or an optionally substituted heteroaryl group having 2 to 20 carbon atoms, a represents an integer of 1 to 4, and when a is 2 or larger, two or more $D^9$ groups present in one molecule may be the same or different, $A^3$ represents a halogen atom, a cyano group, an optionally substituted alkyl group having 1 to 20 carbon atoms, an optionally substituted aryl group having 6 to 20 carbon atoms, an optionally substituted heteroaryl group having 2 to 20 carbon atoms, an optionally substituted alkoxy group having 1 to 20 carbon atoms, or a —COOR$^{604}$ group, $R^{604}$ represents an optionally substituted alkyl group having 1 to 20 carbon atoms, an optionally substituted aryl group having 6 to 20 carbon atoms, or an optionally substituted heteroaryl group having 2 to 20 carbon atoms, $A^4$ represents a halogen atom, an optionally substituted alkyl group having 1 to 20 carbon atoms, an optionally substituted alkenyl group having 2 to 20 carbon atoms, an optionally substituted alkylcarbonyl group having 2 to 20 carbon atoms, an optionally substituted alkoxycarbonyl group having 2 to 20 carbon atoms, a formyl group, an R$^{605}$OOC(NC)C=CH— group, or an NC(NC)C=CH— group, $R^{605}$ represents an optionally substituted alkyl group having 1 to 20 carbon atoms, an optionally substituted aryl group having 6 to 20 carbon atoms, or an optionally substituted heteroaryl group having 2 to 20 carbon atoms, $X^2$ represents a nitrogen atom or a methine group which may have a halogen atom, a cyano group, or a —COOR$^{607}$ group, and $R^{607}$ represents an optionally substituted alkyl group having 1 to 20 carbon atoms, an optionally substituted aryl group having 6 to 20 carbon atoms, or an optionally substituted heteroaryl group having 2 to 20 carbon atoms.

[Chem 20]

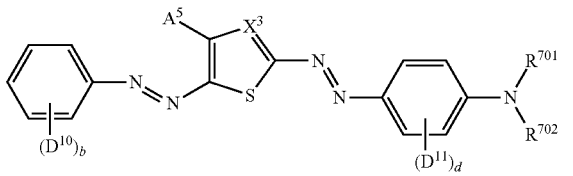

(IX)

wherein $R^{701}$ and $R^{702}$ each independently represent an optionally substituted branched alkyl group having 5 to 20 carbon atoms, $D^{11}$ represents a hydrogen atom, a halogen atom, an optionally substituted alkyl group having 1 to 20 carbon atoms, an optionally substituted alkoxy group having 1 to 20 carbon atoms, an —NHCOR$^{703}$ group, or an —NHSO$_2$R$^{708}$ group, $R^{703}$ and $R^{708}$ each independently represent an optionally substituted alkyl group having 1 to 20 carbon atoms, an optionally substituted aryl group having 6 to 20 carbon atoms, or an optionally substituted heteroaryl group having 2 to 20 carbon atoms, d represents an integer of 1 to 4, and when d is 2 or larger, two or more $D^{11}$ groups present in one molecule may be the same or different, $A^5$ represents a hydrogen atom, a halogen atom, a cyano group, an optionally substituted alkyl group having 1 to 20 carbon atoms, an optionally substituted aryl group having 6 to 20 carbon atoms, an optionally substituted heteroaryl group having 2 to 20 carbon atoms, an optionally substituted alkoxy group having 1 to 20 carbon atoms, or a —COOR$^{704}$ group, $R^{704}$ represents an optionally substituted alkyl group having 1 to 20 carbon atoms, an optionally substituted aryl group having 6 to 20 carbon atoms, or an optionally substituted heteroaryl group having 2 to 20 carbon atoms, $D^{10}$ represents a hydrogen atom, a halogen atom, a cyano group, an optionally substituted alkyl group having 1 to 20 carbon atoms, an optionally substituted alkoxy group having 1 to 20 carbon atoms, a —COOR$^{706}$ group, a —COR$^{709}$ group, or an —OCOR$^{710}$ group, b represents an integer of 1 to 5, and when b is 2 or larger, two or more $D^{10}$ groups present in one molecule may be the same or different, $R^{706}$, $R^{709}$, and $R^{710}$ each independently represent an optionally substituted alkyl group having 1 to 20 carbon atoms, an optionally substituted aryl group having 6 to 20 carbon atoms, or an optionally substituted heteroaryl group having 2 to 20 carbon atoms, $X^3$ represents a nitrogen atom or a methine group which may have a halogen atom, a cyano group, or a —COOR$^{707}$ group, and $R^{707}$ represents an optionally substituted alkyl group having 1 to 20 carbon atoms, an optionally substituted aryl group having 6 to 20 carbon atoms, or an optionally substituted heteroaryl group having 2 to 20 carbon atoms.

In the compounds represented by the general formulae (VIII) and (IX), $R^{601}$ and $R^{602}$ each independently represent an optionally substituted branched alkyl group having 7 to 20 carbon atoms and $R^{701}$ and $R^{702}$ each independently represent an optionally substituted branched alkyl group having 5 to 20 carbon atoms.

The alkyl group of each of $R^{601}$ and $R^{602}$ specifically has the same meaning as the branched alkyl group having 7 or more carbon atoms, among the alkyl groups exemplified in $R^1$ of the above general formula (I) and each substituent which may be possessed also has the same meaning. Moreover, the alkyl group of each of $R^{701}$ and $R^{702}$ specifically has the same meaning as the branched alkyl group having 5 or more carbon atoms, among the alkyl groups exemplified in $R^1$ of the above general formula (I) and each substituent which may be possessed also has the same meaning.

As the alkyl group of each of $R^{601}$ and $R^{602}$, the number of carbon atoms is preferably 7 or more, preferably 8 or more and the number of carbon atoms is preferably 18 or less, more preferably 16 or less.

As the alkyl group of each of $R^{701}$ and $R^{702}$, the number of carbon atoms is preferably 5 or more, preferably 6 or more and the number of carbon atoms is preferably 18 or less, more preferably 16 or less.

When the number of carbon atoms of each of $R^{601}$, $R^{602}$, $R^{701}$, and $R^{702}$ falls within an appropriate range, there are cases where the compound is excellent in solubility in solvents and can have a high gram extinction coefficient.

$D^9$ represents a hydrogen atom, a halogen atom, an optionally substituted alkyl group having 1 to 20 carbon atoms, an optionally substituted alkoxy group having 1 to 20 carbon atoms, an —NHCOR$^{603}$ group, or an —NHSO$_2$R$^{608}$ group, $D^{11}$ represents a hydrogen atom, a halogen atom, an optionally substituted alkyl group having 1 to 20 carbon atoms, an optionally substituted alkoxy group having 1 to 20 carbon atoms, an —NHCOR$^{703}$ group, or an —NHSO$_2$R$^{708}$ group, The alkyl group of each of $D^9$ and $D^{11}$ specifically has the same meaning as the alkyl group exemplified in $R^1$ of the above general formula (I) and each substituent which may be possessed also has the same meaning. As the alkyl group of each of $D^9$ and $D^{11}$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The alkoxy group of each of $D^9$ and $D^{11}$ specifically has the same meaning as the alkoxy group exemplified in $D^1$ of the above general formula (I) and each substituent which may be possessed also has the same meaning. As the alkoxy group of each of $D^9$ and $D^{11}$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

$R^{603}$ and $R^{608}$ each independently represent an optionally substituted alkyl group having 1 to 20 carbon atoms, an optionally substituted aryl group having 6 to 20 carbon atoms, or an optionally substituted heteroaryl group having 2 to 20 carbon atoms, and $R^{703}$ and $R^{708}$ each independently represent an optionally substituted alkyl group having 1 to 20 carbon atoms, an optionally substituted aryl group having 6 to 20 carbon atoms, or an optionally substituted heteroaryl group having 2 to 20 carbon atoms.

The alkyl group of each of $R^{603}$ and $R^{608}$ specifically has the same meaning as the alkyl group exemplified in $R^1$ of the above general formula (I) and each substituent which may be possessed also has the same meaning. As the alkyl group of each of $R^{603}$ and $R^{608}$, the number of carbon atoms is preferably 1 or more and the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The aryl group of each of $R^{603}$ and $R^{608}$ specifically has the same meaning as the aryl group exemplified in $R^3$ of the above general formula (I) and each substituent which may be possessed also has the same meaning as the aryl group exemplified in $R^3$ of the above general formula (I). The heteroaryl group of each of $R^{603}$ and $R^{608}$ specifically has the same meaning as the heteroaryl group exemplified in $R^3$ of the above general formula (I) and each substituent which may be possessed also has the same meaning as the heteroaryl group exemplified in $R^3$ of the above general formula (I).

a represents an integer of 1 to 4, and when a is 2 or larger, two or more $D^9$ groups present in one molecule may be the same or different, and d represents an integer of 1 to 4, and when d is 2 or larger, two or more $D^{11}$ groups present in one molecule may be the same or different.

$A^3$ represents a halogen atom, a cyano group, an optionally substituted alkyl group having 1 to 20 carbon atoms, an optionally substituted aryl group having 6 to 20 carbon atoms, an optionally substituted heteroaryl group having 2 to 20 carbon atoms, an optionally substituted alkoxy group having 1 to 20 carbon atoms, or a —$COOR^{604}$ group, and $A^5$ represents a hydrogen atom, a halogen atom, a cyano group, an optionally substituted alkyl group having 1 to 20 carbon atoms, an optionally substituted aryl group having 6 to 20 carbon atoms, an optionally substituted heteroaryl group having 2 to 20 carbon atoms, an optionally substituted alkoxy group having 1 to 20 carbon atoms, or a —$COOR^{704}$ group.

The alkyl group of each of $A^3$ and $A^5$ specifically has the same meaning as the alkyl group exemplified in $R^1$ of the above general formula (I) and each substituent which may be possessed also has the same meaning. As the alkyl group of each of $A^3$ and $A^5$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The alkoxy group of each of $A^3$ and $A^5$ specifically has the same meaning as the alkoxy group exemplified in $D^1$ of the above general formula (I) and each substituent which may be possessed also has the same meaning. As the alkoxy group of each of $A^3$ and $A^5$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The aryl group of each of $A^3$ and $A^5$ has the same meaning as the aryl group exemplified in $R^3$ of the above general formula (I) and each substituent which may be possessed also has the same meaning as the aryl group exemplified in $R^3$ of the above general formula (I).

As the aryl group of each of $A^3$ and $A^5$, for the reason of high solubility in solvents, an optionally substituted phenyl group or naphthyl group is preferable. As the substituent which may be possessed by the phenyl group or the naphthyl group, for the reason of high solubility in solvents, a halogen atom, an optionally substituted alkyl group having 1 to 10 carbon atoms, or an optionally substituted alkoxy group having 1 to 10 carbon atoms is preferable.

The heteroaryl group of each of $A^3$ and $A^5$ has the same meaning as the heteroaryl group exemplified in $R^3$ of the above general formula (I) and each substituent which may be possessed also has the same meaning as the heteroaryl group exemplified in $R^3$ of the above general formula (I). As the heteroaryl group of each of $A^3$ and $A^5$, for the reason of high solubility in solvents, an optionally substituted thienyl group is preferable. As the substituent which may be possessed by the thienyl group, for the reason of high solubility in solvents, a halogen atom, an optionally substituted alkyl group having 1 to 10 carbon atoms, or an optionally substituted alkoxy group having 1 to 10 carbon atoms is preferable.

$R^{604}$ represents an optionally substituted alkyl group having 1 to 20 carbon atoms, an optionally substituted aryl group having 6 to 20 carbon atoms, or an optionally substituted heteroaryl group having 2 to 20 carbon atoms, and $R^{704}$ represents an optionally substituted alkyl group having 1 to 20 carbon atoms, an optionally substituted aryl group having 6 to 20 carbon atoms, or an optionally substituted heteroaryl group having 2 to 20 carbon atoms.

The alkyl group of each of $R^{604}$ and $R^{704}$ specifically has the same meaning as the alkyl group exemplified in $R^1$ of the above general formula (I) and each substituent which may be possessed also has the same meaning. As the alkyl group of each of $R^{604}$ and $R^{704}$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The aryl group of each of $R^{604}$ and $R^{704}$ specifically has the same meaning as the aryl group exemplified in $R^3$ of the above general formula (I) and each substituent which may be possessed also has the same meaning as the aryl group exemplified in $R^3$ of the above general formula (I).

The heteroaryl group of each of $R^{604}$ and $R^{704}$ specifically has the same meaning as the heteroaryl group exemplified in $R^3$ of the above general formula (I) and each substituent which may be possessed also has the same meaning as the heteroaryl group exemplified in $R^3$ of the above general formula (I).

$X^2$ represents a nitrogen atom or a methine group which may have a halogen atom, a cyano group, or a —$COOR^{607}$ group, and $X^3$ represents a nitrogen atom or a methine group which may have a halogen atom, a cyano group, or a —$COOR^{707}$ group.

Moreover, $R^{607}$ represents an optionally substituted alkyl group having 1 to 20 carbon atoms, an optionally substituted aryl group having 6 to 20 carbon atoms, or an optionally substituted heteroaryl group having 2 to 20 carbon atoms, and $R^{707}$ represents an optionally substituted alkyl group having 1 to 20 carbon atoms, an optionally substituted aryl group having 6 to 20 carbon atoms, or an optionally substituted heteroaryl group having 2 to 20 carbon atoms.

The alkyl group of each of $X^2$ and $X^3$ specifically has the same meaning as the alkyl group exemplified in $R^1$ of the above general formula (I) and each substituent which may be possessed also has the same meaning. As the alkyl group of each of $X^2$ and $X^3$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The aryl group of each of $X^2$ and $X^3$ specifically has the same meaning as the aryl group exemplified in $R^3$ of the above general formula (I) and each substituent which may be possessed also has the same meaning as the aryl group exemplified in $R^3$ of the above general formula (I).

The heteroaryl group of each of $X^2$ and $X^3$ specifically has the same meaning as the heteroaryl group exemplified in $R^3$ of the above general formula (I) and each substituent which may be possessed also has the same meaning as the heteroaryl group exemplified in $R^3$ of the above general formula (I).

$A^4$ represents a halogen atom, an optionally substituted alkyl group having 1 to 20 carbon atoms, an optionally substituted alkenyl group having 2 to 20 carbon atoms, an optionally substituted alkylcarbonyl group having 2 to 20 carbon atoms, an optionally substituted alkoxycarbonyl group having 2 to 20 carbon atoms, a formyl group, an $R^{605}$OOC(NC)C═CH— group, or an NC(NC)C═CH— group, and $R^{605}$ represents an optionally substituted alkyl group having 1 to 20 carbon atoms, an optionally substituted aryl group having 6 to 20 carbon atoms, or an optionally substituted heteroaryl group having 2 to 20 carbon atoms.

The alkyl group of each of $A^4$ and $R^{605}$ specifically has the same meaning as the alkyl group exemplified in $R^1$ of the above general formula (I) and each substituent which may be possessed also has the same meaning.

As the alkyl group of each of $A^4$ and $R^{605}$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The alkenyl group of $A^4$ specifically has the same meaning as the alkenyl group exemplified in $A^2$ of the above general formula (I) and the substituent which may be possessed also has the same meaning. Of the group, the alkenyl group preferably has 3 or more carbon atoms. Moreover, the number of carbon atoms is preferably 16 or less, more preferably 12 or less. When the number of carbon atoms falls within an appropriate range, there are cases where the compound is excellent in solubility in solvents and can have a high gram extinction coefficient.

The alkylcarbonyl group of $A^4$ specifically has the same meaning as the alkylcarbonyl group exemplified in $A^2$ of the above general formula (I) and the substituent which may be possessed also has the same meaning. The number of carbon atoms of the alkyl group in the alkylcarbonyl group of $A^4$ preferably has 1 or more carbon atoms and the number of carbon atoms is preferably 18 or less, more preferably 16 or less.

The alkoxycarbonyl group of $A^4$ specifically has the same meaning as the alkoxycarbonyl group exemplified in $A^2$ of the above general formula (I) and the substituent which may be possessed also has the same meaning. The number of carbon atoms of the alkyl group in the alkoxycarbonyl group of $A^4$ preferably has 1 or more carbon atoms and the number of carbon atoms is preferably 18 or less, more preferably 16 or less.

When the number of carbon atoms of $A^4$ falls within an appropriate range, there are cases where the compound is excellent in solubility in solvents and can have a high gram extinction coefficient.

The aryl group of $R^{605}$ specifically has the same meaning as the aryl group exemplified in $R^3$ of the above general formula (I) and the substituent which may be possessed also has the same meaning as the aryl group exemplified in $R^3$ of the above general formula (I).

The heteroaryl group of $R^{605}$ specifically has the same meaning as the heteroaryl group exemplified in $R^3$ of the above general formula (I) and the substituent which may be possessed also has the same meaning as the heteroaryl group exemplified in $R^3$ of the above general formula (I).

$D^{10}$ represents a hydrogen atom, a halogen atom, a cyano group, an optionally substituted alkyl group having 1 to 20 carbon atoms, an optionally substituted alkoxy group having 1 to 20 carbon atoms, a —$COOR^{706}$ group, a —$COR^{709}$ group, or a —$OCOR^{710}$ group.

Moreover, $R^{706}$, $R^{709}$, and $R^{710}$ each independently represent an optionally substituted alkyl group having 1 to 20 carbon atoms, an optionally substituted aryl group having 6 to 20 carbon atoms, or an optionally substituted heteroaryl group having 2 to 20 carbon atoms.

The alkyl group of each of $D^{10}$, $R^{706}$, $R^{709}$, and $R^{710}$ specifically has the same meaning as the alkyl group exemplified in $R^1$ of the above general formula (I) and each substituent which may be possessed also has the same meaning. As the alkyl group of each of $D^{10}$, $R^{706}$, $R^{709}$, and $R^{710}$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The alkoxy group of $D^{10}$ has the same meaning as the alkoxy group exemplified in $D^1$ of the above general formula (I) and the substituent which may be possessed also has the same meaning. As the alkoxy group of $D^{10}$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The aryl group of each of $R^{706}$, $R^{709}$, and $R^{710}$ specifically has the same meaning as the aryl group exemplified in $R^3$ of the above general formula (I) and each substituent which may be possessed also has the same meaning as the aryl group exemplified in $R^3$ of the above general formula (I).

The heteroaryl group of each of $R^{706}$, $R^{709}$, and $R^{710}$ specifically has the same meaning as the heteroaryl group exemplified in $R^3$ of the above general formula (I) and each substituent which may be possessed also has the same meaning as the heteroaryl group exemplified in $R^3$ of the above general formula (I).

With regard to the azo compound of the invention, the molecular weight thereof is preferably 3,000 or less, more preferably 1,500 or less, including substituent(s) in the case where the compound has the substituent(s). Also, the molecular weight is preferably 400 or more, more preferably 500 or more. When the molecular weight falls within an appropriate range, there are cases where a good gram extinction coefficient can be obtained.

The compounds represented by the general formulae (I) and (VIII) to (XI) can be synthesized, for example, in accordance with the methods described in JP-A-3-256793.

The azo compound of the invention is characterized by having excellent solubility in solvents, in particular, in a solvent having a relative permittivity of 3 or less, as measured at a frequency of 1 kHz and at 22° C. and a solubility in water of 20 mg/L or less at 25° C. The azo compound of the invention has a solubility in n-decane of generally $1 \times 10^{-2}$ mol·$L^{-1}$ or more, preferably $3 \times 10^{-2}$ mol·$L^{-1}$ or more, more preferably $5 \times 10^{-2}$ mol·$L^{-1}$ or more. The higher the solubility is, the more the compound is preferred. However, the solubility thereof is generally about 2 mol·$L^{-1}$ or less. When the solubility is higher than a specific value, there are cases where it becomes possible to display display devices such as a display.

In the case where the azo compound of the invention is to be used in electrowetting displays, it is desirable that the compound should be water-insoluble, in view of the principle thereof. The term "water-insoluble" herein means that the solubility in water under the conditions of 25° C. and 1 atm is 0.1% by mass or less, preferably 0.01% by mass or less.

Moreover, the molar extinction coefficient is preferably 10,000 (L·$mol^{-1}$·$cm^{-1}$) or more, and is more preferably 40,000 (L·$mol^{-1}$·$cm^{-1}$) or more for satisfying the performance of a display device.

Furthermore, the value of the product of the molar extinction coefficient $\epsilon$ (L·$mol^{-1}$·$cm^{-1}$) of n-decane solution of the azo compound of the invention at the absorption-maximum wavelength and the saturated concentration $C$ (mol·$L^{-1}$) of the azo compound in n-decane at 5° C., $\epsilon C$, is preferably 1,000 $cm^{-1}$ or more, more preferably 2,000 $cm^{-1}$ or more. The more the value of $\epsilon C$ is, the more the compound is preferred since the coloration degree becomes high. Although there is no particular upper limit thereon, the value is generally 100,000 cm$^{-1}$ or less.

With respect to the concentration of the azo compound in the ink of the invention, the ink is prepared so as to have any desired concentration in accordance with the intended use thereof. For example, in the case where the compound is to be used as a colorant for electrowetting displays, the compound is used after being diluted with a solvent to a concentration of generally 1% by mass or more in accordance with the desired value of εC. However, the concentration thereof is preferably 3% by mass or more, more preferably 5% by mass or more. Also, the concentration is usually about 80% by mass or less.

The ink of the invention may contain the above azo compound alone or may contain two or more thereof in any combination and ratio.

Since the azo compound of the invention is excellent in solubility in solvents and has a high extinction coefficient, the compound is useful as a material for an optical shutter, a display material, in particular, an electrowetting display material or an electrophoretic display material.

There is no particular lower limit on the viscosity of the ink of the invention which has a temperature of 25° C. However, usually the viscosity is preferably 0.1 mPa·s or more. Meanwhile, the upper limit thereof is preferably 10,000 mPa·s or less, more preferably 1,000 mPa·s or less, particularly preferably 100 mPa·s or less. When the ink has an appropriate viscosity, there are cases where the operation of the display device becomes good.

With respect to the relative permittivity and viscosity of the solvent in the invention and those of the ink containing the solvent, the colorant, and the like, the difference between the solvent and the ink in to values thereof is preferably smaller, because influences on the operation characteristics in the case of use in display devices or the like are lessened.

Consequently, although the ink of the invention may contain any additives suitable for each application according to need within the range where the effects of the invention are not impaired, it is preferable that the properties of the solvent should be kept unchanged.

(Other Compounds)

The above azo compound may be used alone in the ink of the invention or the ink may contain other compound(s) in order to obtain a desired color tone. For example, it is possible to mix a plurality of colored compounds such as yellow, red, blue, purple, and orange compounds with the azo compound of the invention to render the ink black or other color.

Other compounds which may be contained in the ink of the invention can be selected at will from compounds which have solubility or dispersibility in the medium to be used in the invention, so long as the selected compounds do not impair the effects of the invention.

In the case where the ink of the invention is to be used in electrowetting displays, any compounds can be selected and used as other compounds. Examples thereof include nitroso compounds, nitro compounds, monoazo compounds, disazo compounds, trisazo compounds, polyazo compounds, stilbene compounds, carotenoid compounds, diarylmethane compounds, triarylmethane compounds, xanthene compounds, acridine compounds, quinoline compounds, methine compounds, thiazole compounds, isothiazole compounds, indamine compounds, indophenol compounds, azine compounds, oxazine compounds, thiazine compounds, heterocyclic compounds, sulfide dyes, lactone compounds, hydroxyketone compounds, aminoketone compounds, anthraquinone compounds, indigo compounds, phthalocyanine compounds, pyrazole-based compounds, cyanovinyl compounds, natural dyes, oxidation dyes, inorganic pigments, metal complexes, carbon black, and the like.

Specific examples thereof include: Oil Blue N (alkylamine-substituted anthraquinone), Solvent Green, Solvent Blue, Sudan Blue, Sudan Red, Sudan Yellow, Sudan Black, Disperse Violet, Disperse Red, Disperse Blue, and Disperse Yellow; the compounds described in International Publication WO2009/063880; and the compounds described in International Publication WO2010/031860. These compounds themselves are known and are available as commercial products.

In particular, the ink according to the invention preferably contains at least one selected from the group consisting of heterocyclic compounds, cyanovinyl compounds, and anthraquinone compounds. A preferred each colored ink such as a black ink can be rendered possible by using these compounds in any desired combination.

Specific examples of the heterocyclic compounds are not particularly limited but at least one compound selected from the group consisting of the following general formulae (III) to (V) is preferred.

As the heterocyclic compound, a compound represented by the following general formula (III) is mentioned:

[Chem 21]

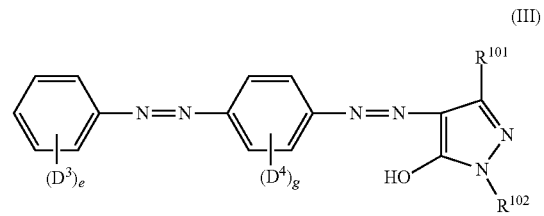

(III)

wherein $R^{101}$, $R^{102}$, $D^3$ and $D^4$ each independently represent an arbitrary substituent, e represents an integer of 1 to 5, and when e is 2 or larger, two or more $D^3$ groups present in one molecule may be the same or different, and g represents an integer of 1 to 4, and when g is 2 or larger, two or more $D^4$ groups present in one molecule may be the same or different.

In the general formula (III), $R^{101}$ and $R^{102}$ each independently represent an arbitrary substituent.

$R^{101}$ is not particularly limited so long as it does not impair the effects of the invention but is preferably an optionally substituted alkyl group having 1 to 20 carbon atoms, an optionally substituted alkoxy group having 1 to 20 carbon atoms, an optionally substituted aryl group having 6 to 20 carbon atoms, an optionally substituted heteroaryl group having 2 to 20 carbon atoms, a —COOR$^{103}$ group, an —NR$^{107}$R$^{108}$ group, or a —COR$^{112}$ group, for a high solubility in solvents and a high extinction coefficient.

Also, $R^{102}$ is not particularly limited so long as it does not impair the effects of the invention but is preferably an optionally substituted alkyl group having 1 to 20 carbon atoms, an optionally substituted aryl group having 6 to 20 carbon atoms, or an optionally substituted heteroaryl group having 2 to 20 carbon atoms, for a high solubility in solvents and a high extinction coefficient.

$R^{103}$ and $R^{112}$ each independently represent an optionally substituted alkyl group having 1 to 20 carbon atoms, an optionally substituted aryl group having 6 to 20 carbon atoms, or an optionally substituted heteroaryl group having 2 to 20 carbon atoms, and $R^{107}$ and $R^{108}$ each independently represent a hydrogen atom, an optionally substituted alkyl group having 1 to 20 carbon atoms, an optionally substituted aryl group having 6 to 20 carbon atoms, or an optionally substituted heteroaryl group having 2 to 20 carbon atoms.

The alkyl group of each of $R^{101}$, $R^{102}$, $R^{103}$, $R^{107l, R108}$, and $R^{112}$ specifically has the same meaning as the alkyl group exemplified in $R^1$ of the above general formula (I) and each substituent which may be possessed also has the same meaning. As the alkyl group of each of $R^{101}$, $R^{102}$, $R^{107}$, $R^{108}$, and $R^{112}$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The aryl group of each of $R^{101}$, $R^{102}$, $R^{103}$, $R^{107}$, $R^{108}$, and $R^{112}$ specifically has the same meaning as the aryl group exemplified in $R^3$ of the above general formula (I) and each substituent which may be possessed also has the same meaning as the aryl group exemplified in $R^3$ of the above general formula (I).

The heteroaryl group of each of $R^{101}$, $R^{102}$, $R^{103}$, $R^{107}$, $R^{108}$, and $R^{112}$ specifically has the same meaning as the heteroaryl group exemplified in $R^3$ of the above general formula (I) and each substituent which may be possessed also has the same meaning as the heteroaryl group exemplified in $R^3$ of the above general formula (I).

$D^3$ represents an arbitrary substituent and is not particularly limited so long as it does not impair the effects of the invention but is preferably a hydrogen atom, a halogen atom, an optionally substituted alkyl group having 1 to 20 carbon atoms, an optionally substituted alkoxy group having 1 to 20 carbon atoms, a cyano group, a hydroxy group, a —COOR$^{104}$ group, an —NHCOR$^{109}$ group, an —NHSO$_2$R$^{110}$ group, a —COR$^{113}$ group, or an —OCOR$^{115}$ group, for a high solubility in solvents and a high extinction coefficient.

Moreover, e represents an integer of 1 to 5, and when e is 2 or larger, two or more $D^3$ groups present in one molecule may be the same or different.

$R^{104}$, $R^{109}$, $R^{110}$, $R^{113}$, and $R^{115}$ each independently represent an optionally substituted alkyl group having 1 to 20 carbon atoms, an optionally substituted aryl group having 6 to 20 carbon atoms, or an optionally substituted heteroaryl group having 2 to 20 carbon atoms.

The alkyl group of each of $D^3$, $R^{104}$, $R^{109}$, $R^{110}$, $R^{113}$, and $R^{115}$ specifically has the same meaning as the alkyl group exemplified in $R^1$ of the above general formula (I) and each substituent which may be possessed also has the same meaning. As the alkyl group of each of $D^3$, $R^{104}$, $R^{109}$, $R^{110}$, $R^{113}$, and $R^{115}$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The alkoxy group of $D^3$ has the same meaning as the alkoxy group exemplified in $D^1$ of the above general formula (I) and each substituent which may be possessed also has the same meaning. As the alkoxy group of $D^3$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The aryl group of each of $R^{104}$, $R^{109}$, $R^{110}$, $R^{113}$, and $R^{115}$ specifically has the same meaning as the aryl group exemplified in $R^3$ of the above general formula (I) and each substituent which may be possessed also has the same meaning as the aryl group exemplified in $R^3$ of the above general formula (I).

The heteroaryl group of each of $R^{104}$, $R^{109}$, $R^{110}$, $R^{113}$, and $R^{115}$ specifically has the same meaning as the heteroaryl group exemplified in $R^3$ of the above general formula (I) and each substituent which may be possessed also has the same meaning as the heteroaryl group exemplified in $R^3$ of the above general formula (I).

$D^4$ represents an arbitrary substituent and is not particularly limited so long as it does not impair the effects of the invention but is preferably a hydrogen atom, a halogen atom, an optionally substituted alkyl group having 1 to 20 carbon atoms, an optionally substituted alkoxy group having 1 to 20 carbon atoms, a cyano group, a —COOR$^{105}$ group, an —NHCOR$^{106}$ group, an —NHSO$_2$R$^{111}$ group, or a —COR$^{114}$ group, for a high solubility in solvents and a high extinction coefficient.

g represents an integer of 1 to 4, and when g is 2 or larger, two or more $D^4$ groups present in one molecule may be the same or different.

$R^{105}$, $R^{106}$, $R^{111}$, and $R^{114}$ each independently represent an optionally substituted alkyl group having 1 to 20 carbon atoms, an optionally substituted aryl group having 6 to 20 carbon atoms, or an optionally substituted heteroaryl group having 2 to 20 carbon atoms.

The alkyl group of each of $D^4$, $R^{105}$, $R^{106}$, $R^{111}$, and $R^{114}$ specifically has the same meaning as the alkyl group exemplified in $R^1$ of the above general formula (I) and each substituent which may be possessed also has the same meaning. As the alkyl group of each of $D^4$, $R^{105}$, $R^{106}$, $R^{111}$, and $R^{114}$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The alkoxy group of $D^4$ has the same meaning as the alkoxy group exemplified in $D^1$ of the above general formula (I) and the substituent which may be possessed also has the same meaning. In the alkoxy group of $D^4$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The aryl group of each of $R^{105}$, $R^{106}$, $R^{111}$, and $R^{114}$ specifically has the same meaning as the aryl group exemplified in $R^3$ of the above general formula (I) and each substituent which may be possessed also has the same meaning as the aryl group exemplified in $R^3$ of the above general formula (I).

The heteroaryl group of each of $R^{105}$, $R^{106}$, $R^{111}$, and $R^{110}$ specifically has the same meaning as the heteroaryl group exemplified in $R^3$ of the above general formula (I) and each substituent which may be possessed also has the same meaning as the heteroaryl group exemplified in $R^3$ of the above general formula (I).

Specific examples of the compound represented by the above general formula (III) are shown in the following. The invention is not limited to these unless it exceeds the gist thereof.

[Chem 22]
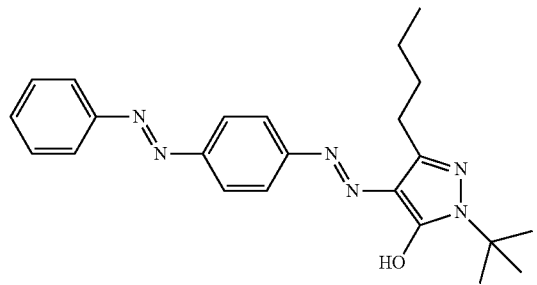
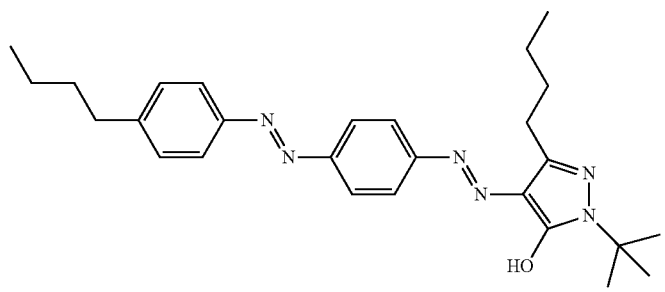
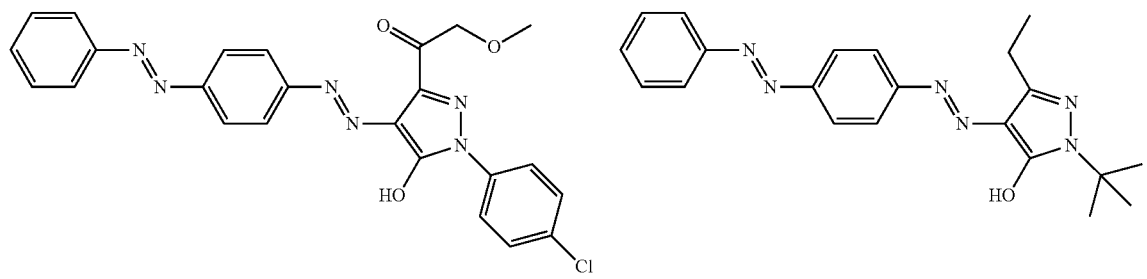
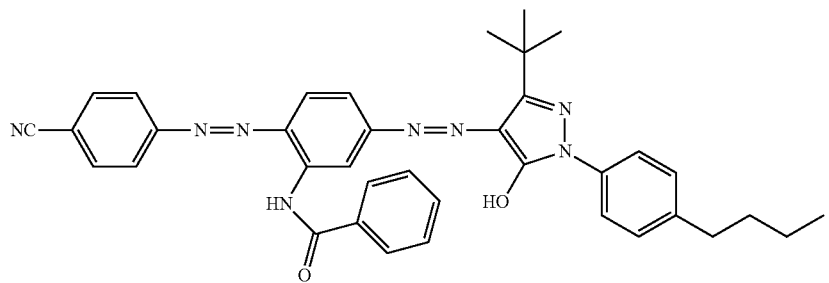
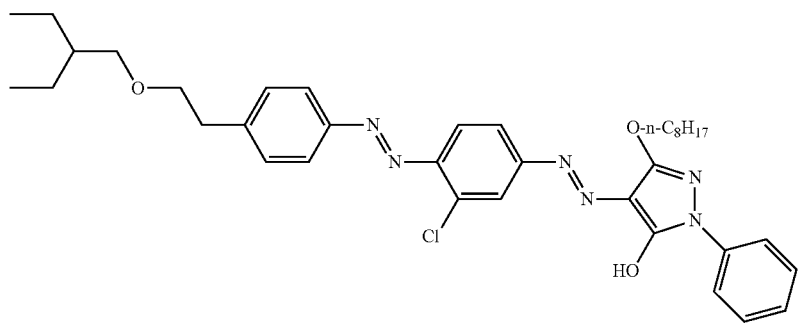

-continued
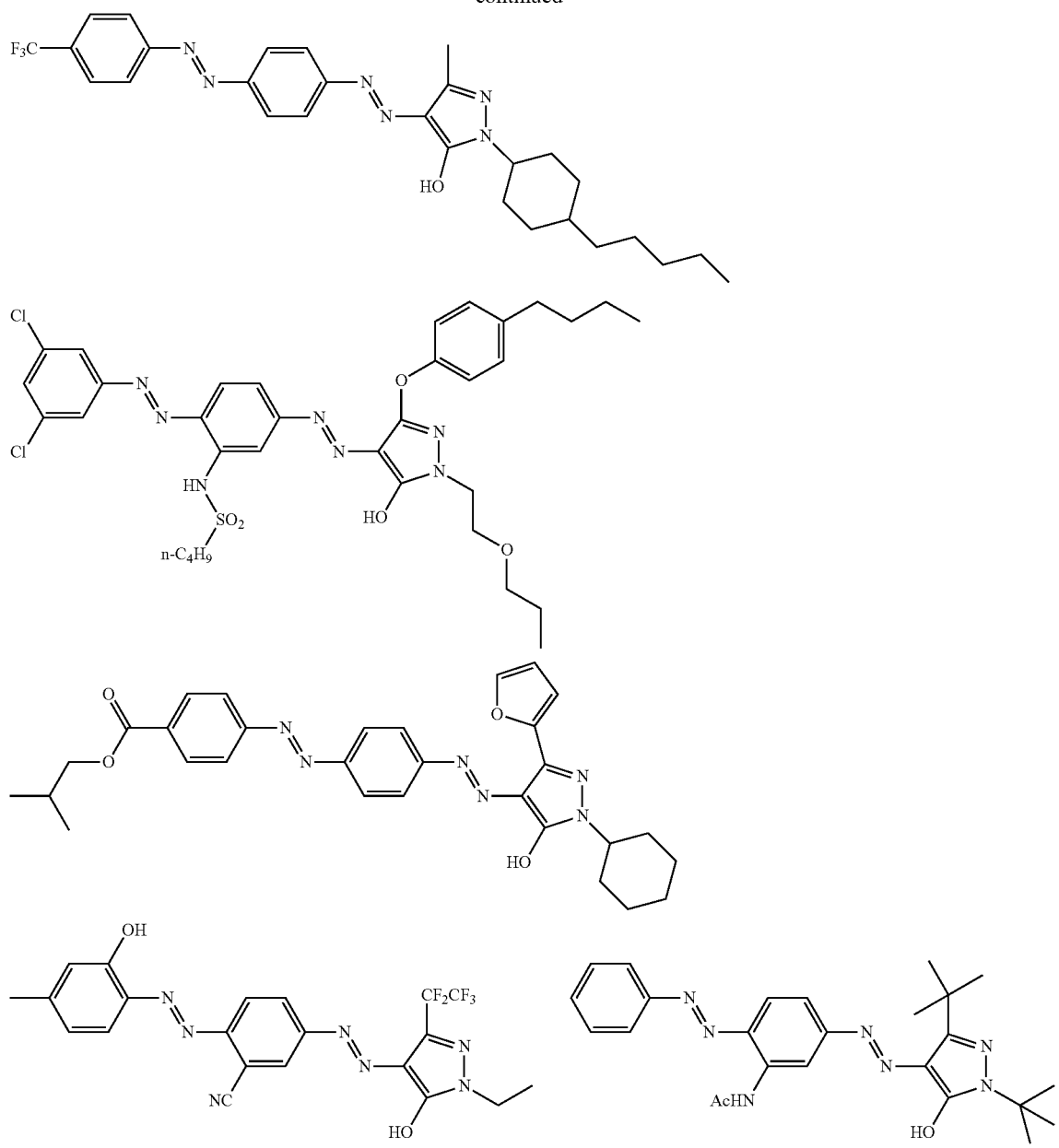
[Chem 23]
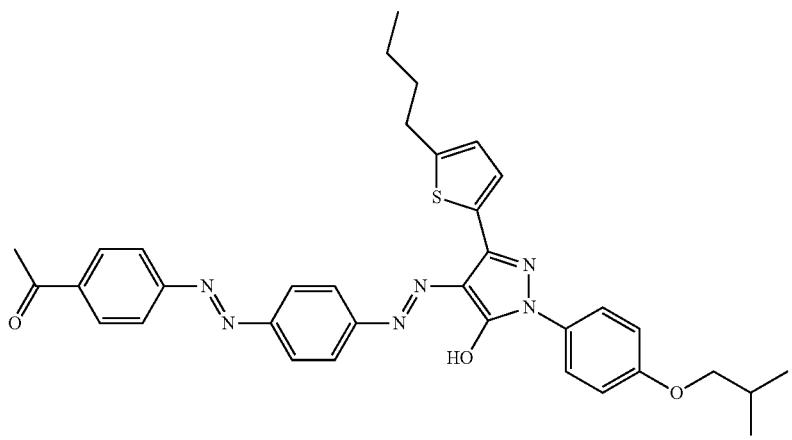

-continued
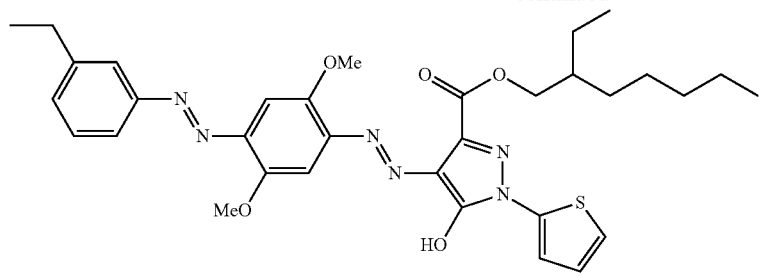
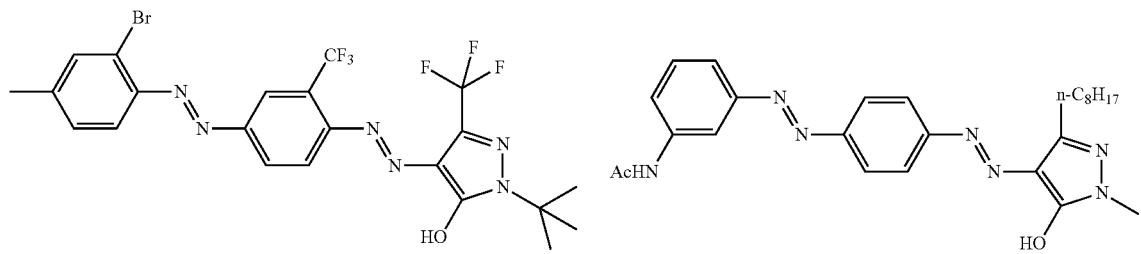
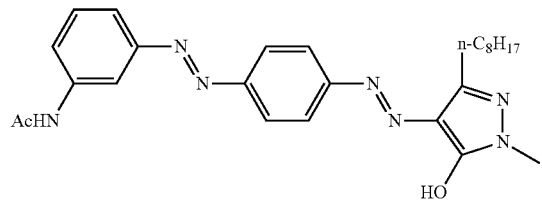
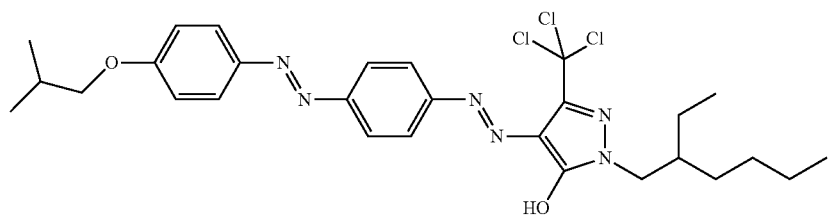
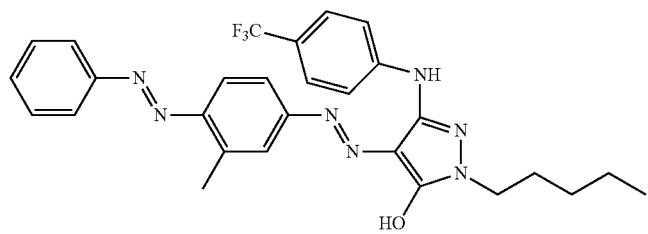
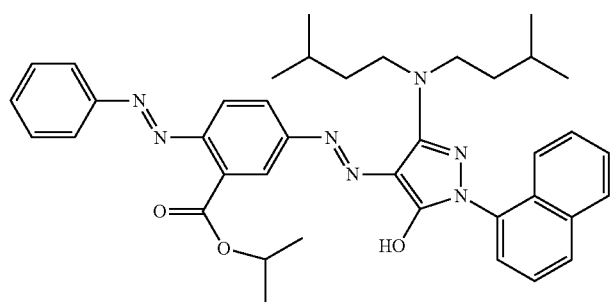
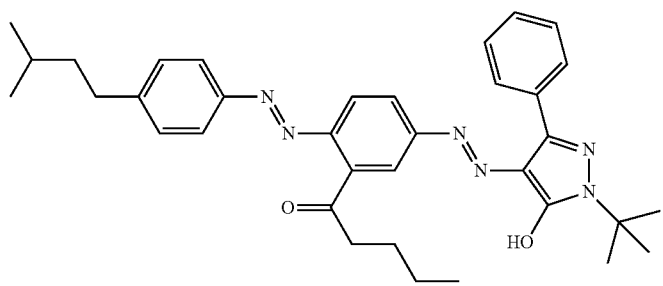

-continued
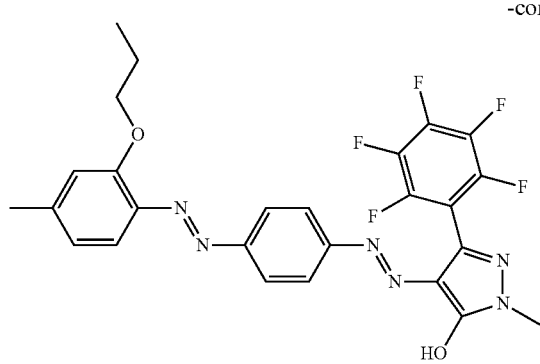
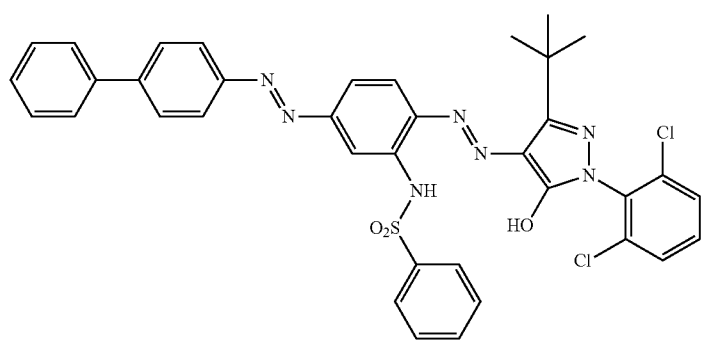
[Chem 24]
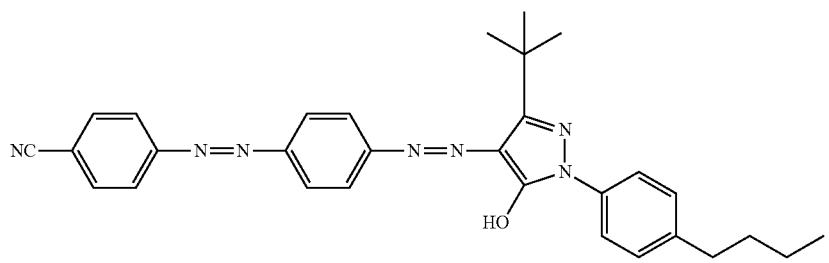
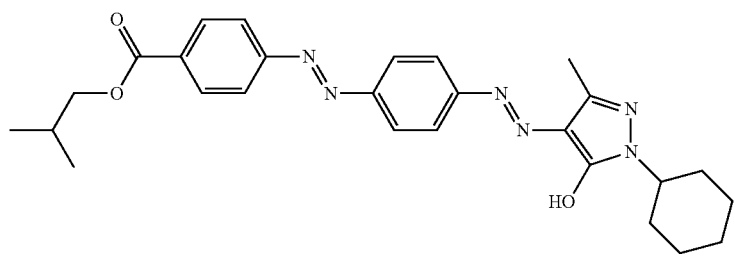
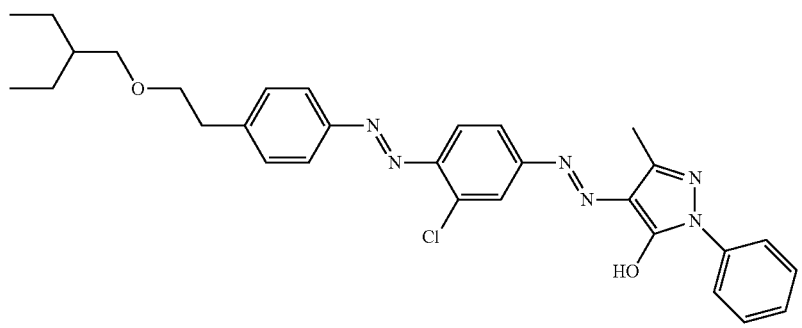

-continued
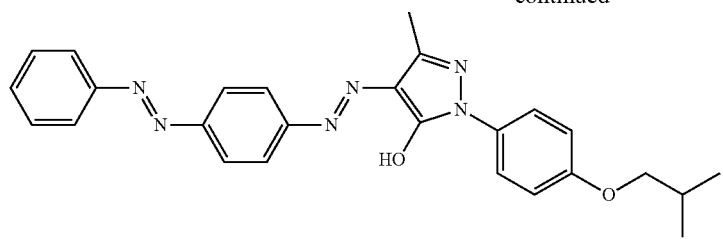
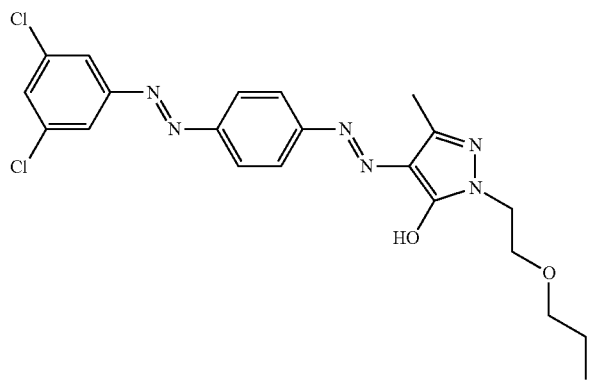
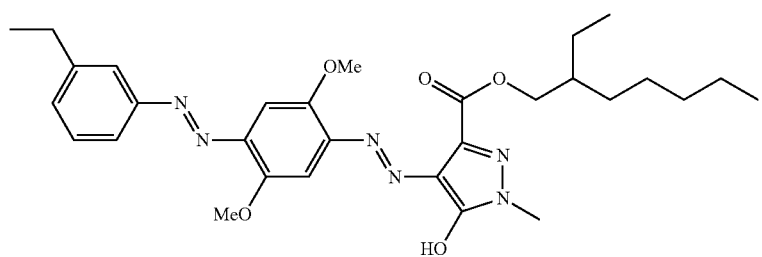
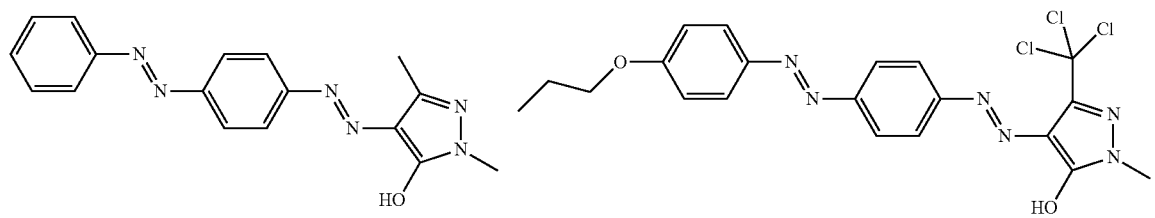
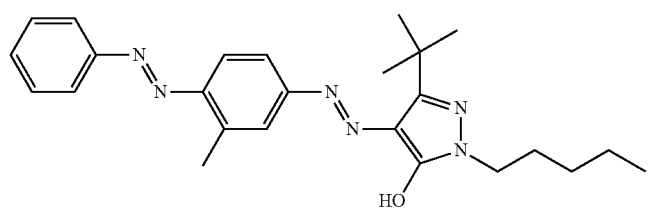
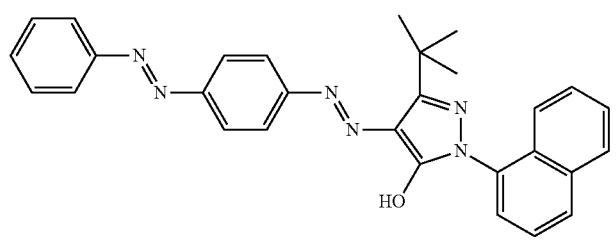

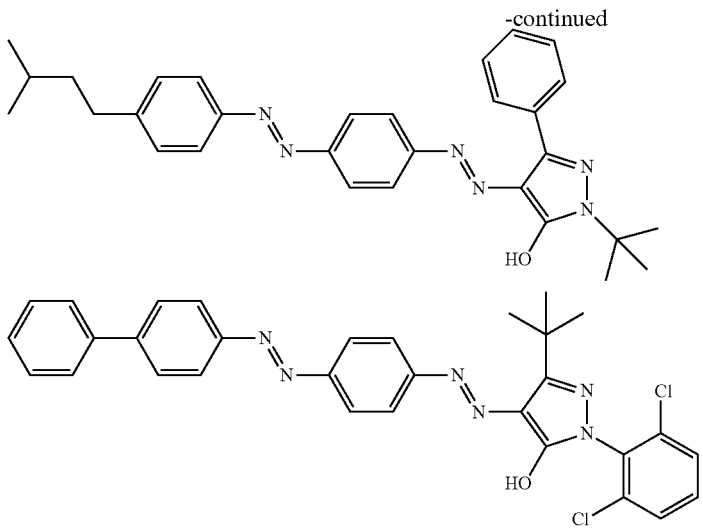

The compound represented by general formula (III) can be synthesized, for example, by the methods described in International Publication WO2009/063880.

As the heterocyclic compound, a compound represented by the following general formula (IV) may be mentioned:

[Chem 25]

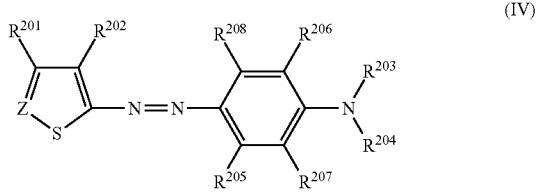

wherein $R^{201}$, $R^{202}$, $R^{203}$, $R^{204}$, $R^{205}$, $R^{206}$, $R^{207}$, and $R^{208}$ each independently represent an arbitrary substituent and Z represents a nitrogen atom or an optionally substituted methine group.

$R^{201}$ represents an arbitrary substituent. $R^{201}$ is not particularly limited so long as it does not impair the effects of the invention but is preferably a hydrogen atom or an optionally substituted alkyl group having 1 to 20 carbon atoms, for a high extinction coefficient.

The alkyl group having 1 to 20 carbon atoms of $R^{201}$ which may have a substituent has the same meaning as the alkyl group exemplified in $R^1$ of the above general formula (I) and the substituent which may be possessed also has the same meaning. Moreover, $R^{201}$ may be combined with Z to form a cyclic structure.

$R^{201}$ is preferably a substituent having a small molecular weight from the viewpoint of the gram extinction coefficient. Specifically, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

Moreover, $R^{201}$ is preferably an unsubstituted alkyl group from the viewpoint of production and is particularly prefer- ably an unsubstituted alkyl group having 1 to 4 carbon atoms, such as methyl, ethyl, propyl, isopropyl, or butyl group.

$R^{202}$ represents an arbitrary substituent. $R^{202}$ is not particularly limited so long as it does not impair the effects of the invention but is preferably a cyano group or a —COOR$^{209}$ group, for a high solubility in solvents and a high extinction coefficient.

$R^{209}$ represents an optionally substituted alkyl group having 1 to 20 carbon atoms, an optionally substituted aryl group having 6 to 20 carbon atoms, or an optionally substituted heteroaryl group having 2 to 20 carbon atoms.

The alkyl group of $R^{209}$ specifically has the same meaning as the alkyl group exemplified in $R^1$ of the above general formula (I) and the substituent which may be possessed also has the same meaning. As the alkyl group of $R^{209}$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The aryl group of $R^{209}$ specifically has the same meaning as the aryl group exemplified in $R^3$ of the above general formula (I) and the substituent which may be possessed also has the same meaning as the aryl group exemplified in $R^3$ of the above general formula (I).

The heteroaryl group of $R^{209}$ specifically has the same meaning as the heteroaryl group exemplified in $R^3$ of the above general formula (I) and the substituent which may be possessed also has the same meaning as the heteroaryl group exemplified in $R^3$ of the above general formula (I).

$R^{203}$ and $R^{204}$ represent an arbitrary substituent. $R^{203}$ and $R^{204}$ are not particularly limited so long as they do not impair the effects of the invention but are each independently preferably an optionally substituted alkyl group having 1 to 20 carbon atoms, for a high solubility in solvents and a high extinction coefficient.

$R^{203}$ and $R^{204}$ may be combined each other to form a cyclic structure. Also, $R^{203}$ and $R^{204}$ may be combined with $R^{206}$ and $R^{207}$, respectively, to form a cyclic structure.

The alkyl group of each of $R^{203}$ and $R^{204}$ specifically has the same meaning as the alkyl group exemplified in $R^1$ of the above general formula (I) and each substituent which may be possessed also has the same meaning. As the alkyl group of each of $R^{203}$ and $R^{204}$, the number of carbon atoms is preferably 2 or more, more preferably 4 or more. Also, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

$R^{205}$, $R^{206}$, $R^{207}$, and $R^{208}$ each independently represent an arbitrary substituent. $R^{205}$, $R^{206}$, $R^{207}$, and $R^{208}$ are not particularly limited so long as they do not impair the effects of the invention but are preferably, a hydrogen atom, a halogen atom, an optionally substituted alkyl group having 1 to 20 carbon atoms, an optionally substituted alkoxy group having 1 to 20 carbon atoms, an —NHCOR$^{210}$ group, or an —NHSO$_2$R$^{212}$ group, for a high solubility in solvents and a high extinction coefficient.

$R^{210}$ and $R^{212}$ each independently represent an optionally substituted alkyl group having 1 to 20 carbon atoms, an optionally substituted aryl group having 6 to 20 carbon atoms, or an optionally substituted heteroaryl group having 2 to 20 carbon atoms.

The alkyl group of each of $R^{205}$, $R^{206}$, $R^{207}$, $R^{208}$, $R^{210}$, and $R^{212}$ specifically has the same meaning as the alkyl group exemplified in $R^1$ of the above general formula (I) and each substituent which may be possessed also has the same meaning. As the alkyl group of each of $R^{205}$, $R^{206}$, $R^{207}$, $R^{208}$, $R^{210}$, and $R^{212}$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The alkoxy group of each of $R^{205}$, $R^{206}$, $R^{207}$, and $R^{208}$ has the same meaning as the alkoxy group exemplified in $D^1$ of the above general formula (I) and each substituent which may be possessed also has the same meaning. As the alkoxy group of each of $R^{205}$, $R^{206}$, $R^{207}$, and $R^{208}$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

Furthermore, $R^{205}$, $R^{206}$, $R^{207}$, and $R^{208}$ are each independently preferably an alkyl group having 1 to 4 carbon atoms, such as methyl, ethyl, propyl, isopropyl, cyclopropyl, butyl, isobutyl, sec-butyl, or tert-butyl group, an —NHCOR$^{210}$ group, or an —NHSO$_2$R$^{212}$ group, and are particularly preferably methyl, an —NHCOR$^{210}$ group, or an —NHSO$_2$R$^{212}$ group, from the standpoints of high solubility in solvents and gram extinction coefficient.

The aryl group of each of $R^{210}$ and $R^{212}$ specifically has the same meaning as the aryl group exemplified in $R^3$ of the above general formula (I) and each substituent which may be possessed also has the same meaning as the aryl group exemplified in $R^3$ of the above general formula (I).

The heteroaryl group of $R^{210}$ and $R^{212}$ specifically has the same meaning as the heteroaryl group exemplified in $R^3$ of the above general formula (I) and each substituent which may be possessed also has the same meaning as the heteroaryl group exemplified in $R^3$ of the above general formula (I).

Z represents a nitrogen atom or an optionally substituted methine group. In the case where Z is a methine group, Z may be unsubstituted or optionally substituted but the substituent which may be possessed by Z includes an optionally substituted alkyl group having 1 to 10 carbon atoms, a —COOR$^{211}$ group, and the like.

$R^{211}$ represents an optionally substituted alkyl group having 1 to 20 carbon atoms. The alkyl group of $R^{211}$ specifically has the same meaning as the alkyl group exemplified in $R^1$ of the above general formula (I) and the substituent which may be possessed also has the same meaning. As the alkyl group of $R^{211}$, the number of carbon atoms is preferably 16 or less, more preferably 10 or less, particularly preferably 6 or less.

When the number of carbon atoms falls within an appropriate range, there are cases where the compound is excellent in solubility in solvents and can have a high gram extinction coefficient.

Z is preferably a nitrogen atom, a methine group, a methine group substituted with an alkyl group having 1 to 4 carbon atoms, or a methine group substituted with an alkoxycarbonyl group having 2 to 5 carbon atoms.

As particularly preferable compounds among the compounds represented by the above general formula (IV), compounds shown in the following Tables 1 to 3 may be mentioned.

TABLE 1

| No. | Z | $R^{201}$ | $R^{202}$ | $R^{203}$ |
|---|---|---|---|---|
| 1 | N | CH$_2$CH$_3$ | CN | i-C$_4$H$_9$ |
| 2 | N | CH$_3$ | CN | CH$_2$CH(CH$_2$CH$_3$)CH$_2$CH$_2$CH$_2$CH$_3$ |
| 3 | C—CO$_2$CH$_2$CH$_3$ | CH$_3$ | CO$_2$CH$_2$CH$_3$ | CH$_2$CH(CH$_2$CH$_3$)CH$_2$CH$_2$CH$_2$CH$_3$ |
| 4 | N | CH$_2$CH$_3$ | CN | CH$_2$CH(CH$_2$CH$_3$)CH$_2$CH$_2$CH$_2$CH$_3$ |
| 5 | N | CH$_3$ | CN | CH$_2$CH(CH$_2$CH$_3$)CH$_2$CH$_2$CH$_2$CH$_3$ |
| 6 | C—CO$_2$CH$_2$CH$_3$ | CH$_3$ | CO$_2$CH$_2$CH$_3$ | CH$_2$CH(CH$_2$CH$_3$)CH$_2$CH$_2$CH$_2$CH$_3$ |
| 7 | C—CO$_2$CH$_2$CH$_3$ | CH$_3$ | CO$_2$CH$_2$CH$_3$ | CH$_2$CH(CH$_2$CH$_3$)CH$_2$CH$_2$CH$_2$CH$_3$ |
| 8 | N | CH$_3$ | CN | CH$_2$CH(CH$_2$CH$_3$)CH$_2$CH$_2$CH$_2$CH$_3$ |
| 9 | N | CH$_3$ | CN | CH$_2$CH(CH$_2$CH$_3$)CH$_2$CH$_2$CH$_2$CH$_3$ |
| 10 | N | CH$_2$CH$_3$ | CN | CH$_2$CH(CH$_2$CH$_3$)CH$_2$CH$_2$CH$_2$CH$_3$ |
| 11 | N | CH$_2$CH$_3$ | CN | CH$_2$CH(CH$_2$CH$_3$)CH$_2$CH$_2$CH$_2$CH$_3$ |
| 12 | N | n-C$_4$H$_9$ | CN | i-C$_4$H$_9$ |
| 13 | N | n-C$_4$H$_9$ | CN | CH$_2$CH(CH$_2$CH$_3$)CH$_2$CH$_2$CH$_2$CH$_3$ |
| 14 | N | i-C$_3$H$_7$ | CN | CH$_2$CH(CH$_2$CH$_3$)CH$_2$CH$_2$CH$_2$CH$_3$ |
| 15 | N | CH$_3$ | CN | CH$_2$CH(CH$_2$CH$_3$)CH$_2$CH$_2$CH$_2$CH$_3$ |
| 16 | N | CH$_3$ | CN | CH$_2$CH(CH$_2$CH$_3$)CH$_2$CH$_2$CH$_2$CH$_3$ |
| 17 | N | CH$_3$ | CN | CH$_2$CH(CH$_2$CH$_3$)CH$_2$CH$_2$CH$_2$CH$_3$ |
| 18 | C—CO$_2$CH$_2$CH$_3$ | CH$_3$ | CO$_2$CH$_2$CH$_3$ | i-C$_4$H$_9$ |
| 19 | C—CO$_2$CH$_2$CH$_3$ | CH$_3$ | CN | CH$_2$CH(CH$_2$CH$_3$)CH$_2$CH$_2$CH$_2$CH$_3$ |
| 20 | C—CO$_2$CH$_2$CH$_3$ | CH$_3$ | CN | CH$_2$CH(CH$_2$CH$_3$)CH$_2$CH$_2$CH$_2$CH$_3$ |

TABLE 1-continued

| No. | R$^{204}$ | R$^{205}$ | R$^{206}$ | R$^{207}$ | R$^{208}$ |
|---|---|---|---|---|---|
| 1 | i-C$_4$H$_9$ | NHCOCH$_3$ | H | H | H |
| 2 | CH$_2$CH(CH$_2$CH$_3$)CH$_2$CH$_2$CH$_2$CH$_3$ | NHCOCH$_3$ | H | H | H |
| 3 | CH$_2$CH(CH$_2$CH$_3$)CH$_2$CH$_2$CH$_2$CH$_3$ | NHCOCH$_3$ | H | H | H |
| 4 | CH$_2$CH(CH$_2$CH$_3$)CH$_2$CH$_2$CH$_2$CH$_3$ | CH$_3$ | H | H | H |
| 5 | n-C$_8$H$_{17}$ | CH$_3$ | H | H | H |
| 6 | CH$_2$CH(CH$_2$CH$_3$)CH$_2$CH$_2$CH$_2$CH$_3$ | CH$_3$ | H | H | H |
| 7 | CH$_2$CH(CH$_2$CH$_3$)CH$_2$CH$_2$CH$_2$CH$_3$ | NHCOCH$_2$CH$_3$ | H | H | H |
| 8 | CH$_2$CH(CH$_2$CH$_3$)CH$_2$CH$_2$CH$_2$CH$_3$ | CH$_2$CH$_3$ | H | H | H |
| 9 | CH$_2$CH(CH$_2$CH$_3$)CH$_2$CH$_2$CH$_2$CH$_3$ | NHCOCH$_2$CH$_3$ | H | H | H |
| 10 | CH$_2$CH(CH$_2$CH$_3$)CH$_2$CH$_2$CH$_2$CH$_3$ | NHCOCH$_3$ | H | H | H |
| 11 | CH$_2$CH$_3$ | NHCOCH$_3$ | H | H | H |
| 12 | i-C$_4$H$_9$ | NHCOCH$_3$ | H | H | H |
| 13 | CH$_2$CH(CH$_2$CH$_3$)CH$_2$CH$_2$CH$_2$CH$_3$ | CH$_3$ | H | H | H |
| 14 | CH$_2$CH(CH$_2$CH$_3$)CH$_2$CH$_2$CH$_2$CH$_3$ | CH$_3$ | H | H | H |
| 15 | CH$_2$CH(CH$_2$CH$_3$)CH$_2$CH$_2$CH$_2$CH$_3$ | i-C$_3$H$_7$ | H | H | H |
| 16 | CH$_2$CH(CH$_2$CH$_3$)CH$_2$CH$_2$CH$_2$CH$_3$ | CH$_3$ | OCH$_3$ | H | H |
| 17 | CH$_2$CH(CH$_2$CH$_3$)CH$_2$CH$_2$CH$_2$CH$_3$ | H | H | H | H |
| 18 | i-C$_4$H$_9$ | CH$_3$ | H | H | H |
| 19 | CH$_2$CH(CH$_2$CH$_3$)CH$_2$CH$_2$CH$_2$CH$_3$ | CH$_3$ | OCH$_3$ | H | H |
| 20 | CH$_2$CH(CH$_2$CH$_3$)CH$_2$CH$_2$CH$_2$CH$_3$ | CH$_2$CH$_3$ | H | H | H |

TABLE 2

| No. | Z | R$^{201}$ | R$^{202}$ | R$^{203}$ |
|---|---|---|---|---|
| 21 | N | i-C$_3$H$_7$ | CN | i-C$_4$H$_9$ |
| 22 | N | CH$_3$ | CO$_2$CH$_3$ | CH$_2$CH(CH$_2$CH$_3$)CH$_2$CH$_2$CH$_2$CH$_3$ |
| 23 | N | CH$_3$ | CO$_2$-n-C$_3$H$_7$ | i-C$_4$H$_9$ |
| 24 | N | CH$_3$ | CN | (CF$_2$)$_5$CF$_3$ |
| 25 | N | CH$_3$ | CN | CH$_2$CH(CH$_2$CH$_3$)CH$_2$CH$_2$CH$_2$CH$_3$ |
| 26 | N | CH$_3$ | CN | i-C$_4$H$_9$ |
| 27 | N | CH$_3$ | CN | CH$_2$CH(CH$_2$CH$_3$)CH$_2$CH$_2$CH$_2$CH$_3$ |
| 28 | C—CO$_2$CH$_3$ | CH$_3$ | CO$_2$CH$_3$ | CH$_2$CH(CH$_2$CH$_3$)CH$_2$CH$_2$CH$_2$CH$_3$ |
| 29 | C—CO$_2$-n-C$_4$H$_9$ | CH$_3$ | CO$_2$-n-C$_4$H$_9$ | i-C$_4$H$_9$ |
| 30 | C—CH$_3$ | CH$_3$ | CO$_2$CH$_3$ | CH$_2$CH(CH$_2$CH$_3$)CH$_2$CH$_2$CH$_2$CH$_3$ |
| 31 | C-n-C$_4$H$_9$ | CH$_3$ | CO$_2$CH$_3$ | i-C$_4$H$_9$ |
| 32 | C—CO$_2$—CH$_2$CH$_3$ | CH$_3$ | CN | CH$_2$CH(CH$_2$CH$_3$)CH$_2$CH$_2$CH$_2$CH$_3$ |
| 33 | C—CO$_2$—CH$_2$CH$_3$ | CH$_3$ | CO$_2$—CH$_2$CH$_3$ | CH$_2$CH(CH$_2$CH$_3$)CH$_2$CH$_2$CH$_2$CH$_3$ |
| 34 | C—CO$_2$—CH$_2$CH$_3$ | CH$_3$ | CO$_2$—CH$_2$CH$_3$ | CH$_2$CH(CH$_2$CH$_3$)CH$_2$CH$_2$CH$_2$CH$_3$ |
| 35 | C—CO$_2$—CH$_2$CH$_3$ | CH$_3$ | CN | CH$_2$CH(CH$_2$CH$_3$)CH$_2$CH$_2$CH$_2$CH$_3$ |
| 36 | C—CN | CH$_3$ | CN | CH$_2$CH(CH$_2$CH$_3$)CH$_2$CH$_2$CH$_2$CH$_3$ |
| 37 | C—CN | CH$_3$ | CN | CH$_2$CH(CH$_2$CH$_3$)CH$_2$CH$_2$CH$_2$CH$_3$ |
| 38 | N | CH$_3$ | CN | CH$_2$CH(CH$_2$CH$_3$)CH$_2$CH$_2$CH$_2$CH$_3$ |
| 39 | N | CH$_3$ | CN | CH$_2$CH(CH$_2$CH$_3$)CH$_2$CH$_2$CH$_2$CH$_3$ |
| 40 | C—CO$_2$CH$_3$ | CH$_3$ | CO$_2$CH$_3$ | CH$_2$CH(CH$_2$CH$_3$)CH$_2$CH$_2$CH$_2$CH$_3$ |

| No. | R$^{204}$ | R$^{205}$ | R$^{206}$ | R$^{207}$ | R$^{208}$ |
|---|---|---|---|---|---|
| 21 | i-C$_4$H$_9$ | H | H | H | H |
| 22 | CH$_2$CH(CH$_2$CH$_3$)CH$_2$CH$_2$CH$_2$CH$_3$ | NHCOCH$_3$ | H | H | H |
| 23 | i-C$_4$H$_9$ | NHCOCH$_3$ | H | H | H |
| 24 | (CF$_2$)$_5$CF$_3$ | NHCOCH$_3$ | H | H | H |
| 25 | CH$_2$CH(CH$_2$CH$_3$)CH$_2$CH$_2$CH$_2$CH$_3$ | NHCOPh | H | H | H |
| 26 | i-C$_4$H$_9$ | NHCO-i-C$_4$H$_9$ | H | H | H |
| 27 | CH$_2$CH(CH$_2$CH$_3$)CH$_2$CH$_2$CH$_2$CH$_3$ | NHCOCH$_3$ | OCH$_3$ | H | H |
| 28 | CH$_2$CH(CH$_2$CH$_3$)CH$_2$CH$_2$CH$_2$CH$_3$ | Cl | H | CH$_3$ | H |
| 29 | i-C$_4$H$_9$ | NHCOCH$_3$ | CH$_3$ | H | H |
| 30 | CH$_2$CH(CH$_2$CH$_3$)CH$_2$CH$_2$CH$_2$CH$_3$ | CH$_3$ | H | OCH$_3$ | H |
| 31 | i-C$_4$H$_9$ | NHCO-i-C$_4$H$_9$ | H | H | H |
| 32 | CH$_2$CH(CH$_2$CH$_3$)CH$_2$CH$_2$CH$_2$CH$_3$ | NHCOCH$_3$ | H | H | H |
| 33 | CH$_2$CH(CH$_2$CH$_3$)CH$_2$CH$_2$CH$_2$CH$_3$ | NHCOCH$_3$ | OCH$_3$ | H | H |
| 34 | CH$_2$CH(CH$_2$CH$_3$)CH$_2$CH$_2$CH$_2$CH$_3$ | CH$_3$ | OCH$_3$ | H | H |
| 35 | CH$_2$CH(CH$_2$CH$_3$)CH$_2$CH$_2$CH$_2$CH$_3$ | CH$_3$ | H | H | H |
| 36 | CH$_2$CH(CH$_2$CH$_3$)CH$_2$CH$_2$CH$_2$CH$_3$ | NHCOCH$_3$ | H | H | H |
| 37 | CH$_2$CH(CH$_2$CH$_3$)CH$_2$CH$_2$CH$_2$CH$_3$ | CH$_3$ | H | H | H |
| 38 | CH$_2$CH(CH$_2$CH$_3$)CH$_2$CH$_2$CH$_2$CH$_3$ | NHCOCH$_3$ | Cl | H | H |
| 39 | CH$_2$CH(CH$_2$CH$_3$)CH$_2$CH$_2$CH$_2$CH$_3$ | F | H | H | H |
| 40 | CH$_2$CH(CH$_2$CH$_3$)CH$_2$CH$_2$CH$_2$CH$_3$ | Cl | CH$_3$ | H | H |

TABLE 3

| No. | Z | $R^{201}$ | $R^{202}$ | $R^{203}$ |
|---|---|---|---|---|
| 41 | N | n-$C_6H_{13}$ | $CO_2$-n-$C_4H_9$ | n-$C_6H_{13}$ |
| 42 | N | $CH_2OCH_2CH_3$ | $CO_2CF_3$ | $CH_2OCH_2CH_3$ |
| 43 | N | $CF_3$ | $CO_2$—Ph | $CF_3$ |
| 44 | N | $CF_2CF_3$ | $CO_2CH_2$—Ph | $CF_2CF_3$ |
| 45 | N | Ph | $CO_2CH_2$-cyclohexane | Ph |
| 46 | N | $CH_2$—Ph | $CO_2CH_2CH_2OCH_3$ | $CH_2$—Ph |
| 47 | N | $CH_2CH_2O$—Ph | $CO_2$-n-$C_8H_{17}$ | $CH_2CH_2O$—Ph |
| 48 | N | $CH_2$-cyclohexane | $CO_2CH_2CH_2CH_2CF_3$ | $CH_2$-cyclohexane |
| 49 | N | n-$C_8H_{17}$ | $CO_2CH_2CH_2CH_2CN$ | n-$C_8H_{17}$ |
| 50 | N | $CH_3$ | CN | $CH_2CH(CH_2CH_3)CH_2CH_2CH_2CH_3$ |
| 51 | C—$CO_2$Ph | n-$C_6H_{13}$ | $CO_2$-n-$C_4H_9$ | n-$C_6H_{13}$ |
| 52 | C—$CO_2CH_2$Ph | $CH_2OCH_2CH_3$ | $CO_2CF_3$ | $CH_2OCH_2CH_3$ |
| 53 | C—$CO_2$-n-$C_8H_{17}$ | $CF_3$ | $CO_2$—Ph | $CF_3$ |
| 54 | C—$CO_2$-n-$C_6H_{13}$ | $CF_2CF_3$ | $CO_2CH_2$—Ph | $CF_2CF_3$ |
| 55 | C—$CO_2$-cyclohaxne | Ph | $CO_2CH_2$-cyclohexane | Ph |
| 56 | C—CN | $CH_2$—Ph | $CO_2CH_2CH_2OCH_3$ | $CH_2$—Ph |
| 57 | C—CN | $CH_2CH_2O$—Ph | $CO_2$-n-$C_8H_{17}$ | $CH_2CH_2O$—Ph |
| 58 | C—CN | $CH_2$-cyclohexane | $CO_2CH_2CH_2CH_2CF_3$ | $CH_2$-cyclohexane |
| 59 | C—CN | n-$C_8H_{17}$ | $CO_2CH_2CH_2CH_2CN$ | n-$C_8H_{17}$ |
| 60 | C—CN | $CH_2CH_2CH_2CF_3$ | $CO_2CH_2(CH_3)CH_2CH_3$ | $CH_2CH_2CH_2CF_3$ |

| No. | $R^{204}$ | $R^{205}$ | $R^{206}$ | $R^{207}$ | $R^{208}$ |
|---|---|---|---|---|---|
| 41 | n-$C_6H_{13}$ | O-n-Bu | H | H | H |
| 42 | $CH_2OCH_2CH_3$ | $CF_3$ | H | H | H |
| 43 | $CF_3$ | $NHSO_2CF_3$ | H | H | H |
| 44 | $CF_2CF_3$ | $NHSO_2$-n-Bu | H | H | H |
| 45 | Ph | Br | H | H | H |
| 46 | $CH_2$—Ph | H | O-n-$C_6H_{13}$ | H | H |
| 47 | $CH_2CH_2O$—Ph | H | $CF_2CF_2CF_2CF_3$ | H | H |
| 48 | $CH_2$-cyclohexane | H | $NHSO_2CH_2$—Ph | H | H |
| 49 | n-$C_8H_{17}$ | H | $NHSO_2$—Ph | H | H |
| 50 | $CH_2CH(CH_2CH_3)CH_2CH_2CH_2CH_3$ | $NHSO_2$-n-Bu | H | H | H |
| 51 | n-$C_6H_{13}$ | O-n-Bu | H | H | H |
| 52 | $CH_2OCH_2CH_3$ | $CF_3$ | H | H | H |
| 53 | $CF_3$ | $NHSO_2CF_3$ | H | H | H |
| 54 | $CF_2CF_3$ | $NHSO_2$-n-Bu | H | H | H |
| 55 | Ph | Br | H | H | H |
| 56 | $CH_2$—Ph | H | O-n-$C_6H_{13}$ | H | H |
| 57 | $CH_2CH_2O$—Ph | H | $CF_2CF_2CF_2CF_3$ | H | H |
| 58 | $CH_2$-cyclohexane | H | $NHSO_2CH_2$—Ph | H | H |
| 59 | n-$C_8H_{17}$ | H | $NHSO_2$—Ph | H | H |
| 60 | $CH_2CH_2CH_2CF_3$ | Me | H | Me | H |

The compound represented by general formula (IV) can be synthesized, for example, in accordance with the methods described in JP-A-8-505820.

As the heterocyclic compound, a compound represented by the following general formula (V) may be mentioned:

[Chem 26]

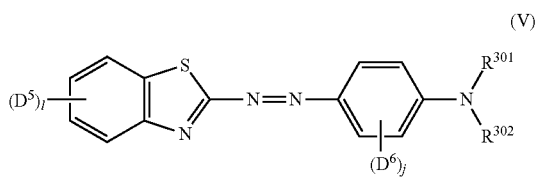

(V)

wherein $R^{301}$, $R^{302}$, $D^5$, and $D^6$ each independently represent an arbitrary substituent, l represents an integer of 1 to 4, and when l is 2 or larger, two or more $D^5$ groups present in one molecule may be the same or different, and j represents an integer of 1 to 4, and when j is 2 or larger, two or more $D^6$ groups present in one molecule may be the same or different.

$R^{301}$ and $R^{302}$ each independently represent an arbitrary substituent. $R^{301}$ and $R^{302}$ are not particularly limited so long as they do not impair the effects of the invention but are preferably, an optionally substituted alkyl group having 1 to 20 carbon atoms, an optionally substituted aryl group having 6 to 20 carbon atoms, or an optionally substituted heteroaryl group having 2 to 20 carbon atoms, for a high extinction coefficient and a high solubility in solvents.

The alkyl group of each of $R^{301}$ and $R^{302}$ specifically has the same meaning as the alkyl group exemplified in $R^1$ of the above general formula (I) and each substituent which may be possessed also has the same meaning. As the alkyl group of each of $R^{301}$ and $R^{302}$, the number of carbon atoms is preferably 2 or more, more preferably 4 or more. Also, the number of carbon atoms is preferably 16 or less, more preferably 12 or less. When the number of carbon atoms falls within an appropriate range, there are cases where the compound is excellent in solubility in solvents and can have a high gram extinction coefficient.

The aryl group of each of $R^{301}$ and $R^{302}$ specifically has the same meaning as the aryl group exemplified in $R^3$ of the above general formula (I) and each substituent which may be possessed also has the same meaning as the aryl group exemplified in $R^3$ of the above general formula (I).

The heteroaryl group of each of $R^{301}$ and $R^{302}$ specifically has the same meaning as the heteroaryl group exemplified in $R^3$ of the above general formula (I) and each substituent which may be possessed also has the same meaning as the heteroaryl group exemplified in $R^3$ of the above general formula (I).

$D^5$ represents an arbitrary substituent. $D^5$ is not particularly limited so long as it does not impair the effects of the invention but is preferably, a hydrogen atom, a halogen atom, a cyano group, an optionally substituted alkyl group having 1 to 20 carbon atoms, an optionally substituted alkoxy group having 1 to 20 carbon atoms, an —SCN group, a —COOR$^{303}$ group, a —COR$^{306}$ group, or an —OCOR$^{307}$ group, for a high extinction coefficient and a high solubility in solvents.

l represents an integer of 1 to 4, and when l is 2 or larger, two or more $D^5$ groups present in one molecule may be the same or different.

Moreover, $R^{303}$, $R^{306}$, and $R^{307}$ each independently represent an optionally substituted alkyl group having 1 to 20 carbon atoms, an optionally substituted aryl group having 6 to 20 carbon atoms, or an optionally substituted heteroaryl group having 2 to 20 carbon atoms.

The alkyl group of each of $D^5$, $R^{303}$, $R^{306}$, and $R^{307}$ specifically has the same meaning as the alkyl group exemplified in $R^1$ of the above general formula (I) and each substituent which may be possessed also has the same meaning. As the alkyl group of each of $D^5$, $R^{303}$, $R^{306}$, and $R^{307}$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The alkoxy group of $D^5$ has the same meaning as the alkoxy group exemplified in $D^1$ of the above general formula (I) and the substituent which may be possessed also has the same meaning. As the alkoxy group of each of $D^5$ and the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The aryl group of each of $R^{303}$, $R^{306}$, and $R^{307}$ specifically has the same meaning as the aryl group exemplified in $R^3$ of the above general formula (I) and each substituent which may be possessed also has the same meaning as the aryl group exemplified in $R^3$ of the above general formula (I).

The heteroaryl group of each of $R^{303}$, $R^{306}$, and $R^{307}$ specifically has the same meaning as the heteroaryl group exemplified in $R^3$ of the above general formula (I) and each substituent which may be possessed also has the same meaning as the heteroaryl group exemplified in $R^3$ of the above general formula (I).

$D^6$ represents an arbitrary substituent. $D^6$ is not particularly limited so long as it does not impair the effects of the invention but is preferably, a hydrogen atom, an optionally substituted alkyl group having 1 to 20 carbon atoms, an optionally substituted alkoxy group having 1 to 20 carbon atoms, an —NHCOR$^{304}$ group, or an —NHSO$_2$R$^{305}$ group, for a high solubility in solvents and a high extinction coefficient.

j represents an integer of 1 to 4, and when j is 2 or larger, two or more $D^6$ groups present in one molecule may be the same or different.

Moreover, $R^{304}$ and $R^{305}$ each independently represent an optionally substituted alkyl group having 1 to 20 carbon atoms, an optionally substituted aryl group having 6 to 20 carbon atoms, or an optionally substituted heteroaryl group having 2 to 20 carbon atoms.

The alkyl group of each of $D^6$, $R^{304}$, and $R^{305}$ specifically has the same meaning as the alkyl group exemplified in $R^1$ of the above general formula (I) and each substituent which may be possessed also has the same meaning. As the alkyl group of each of $D^6$, $R^{304}$, and $R^{305}$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The alkoxy group of $D^6$ has the same meaning as the alkoxy group exemplified in $D^1$ of the above general formula (I) and the substituent which may be possessed also has the same meaning. As the alkoxy group of $D^6$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The aryl group of each of $R^{304}$ and $R^{305}$ specifically has the same meaning as the aryl group exemplified in $R^3$ of the above general formula (I) and each substituent which may be possessed also has the same meaning as the aryl group exemplified in $R^3$ of the above general formula (I).

The heteroaryl group of each of $R^{304}$ and $R^{305}$ specifically has the same meaning as the heteroaryl group exemplified in $R^3$ of the above general formula (I) and each substituent which may be possessed also has the same meaning as the heteroaryl group exemplified in $R^3$ of the above general formula (I).

Specific examples of the compound represented by the above general formula (V) are shown in the following but are not limited to these unless they exceed the gist thereof.

[Chem 27]

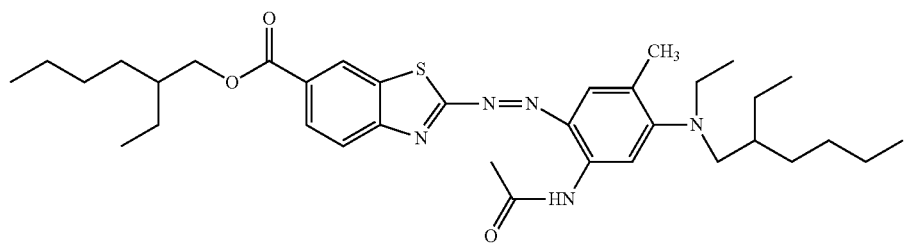

-continued
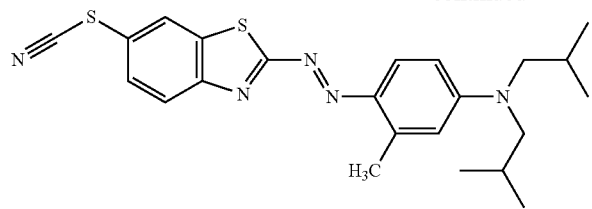
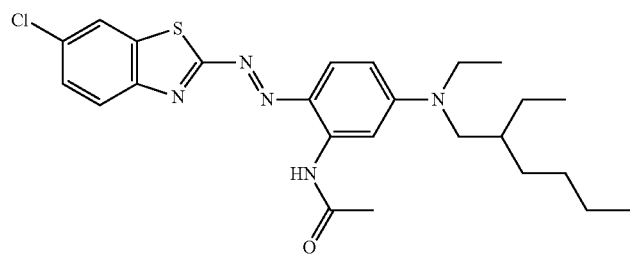
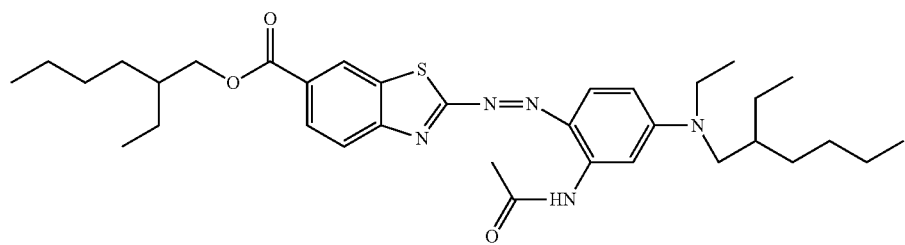
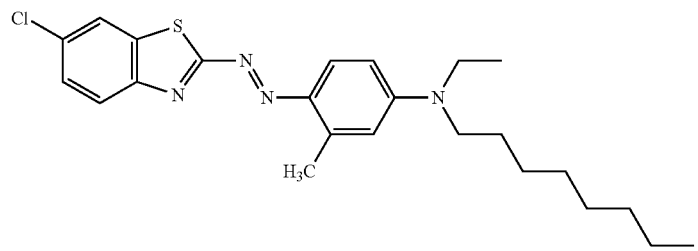
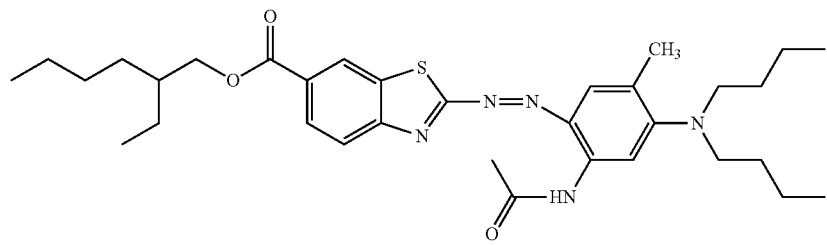
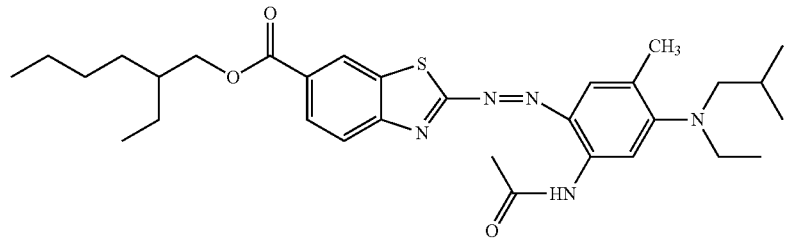
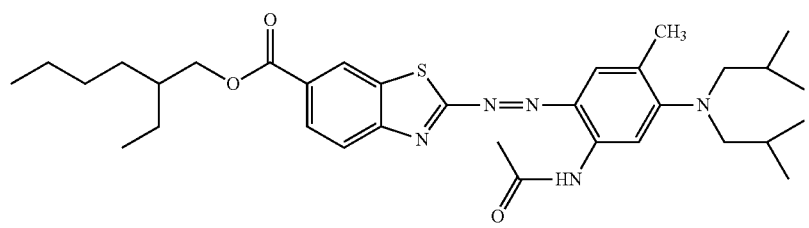

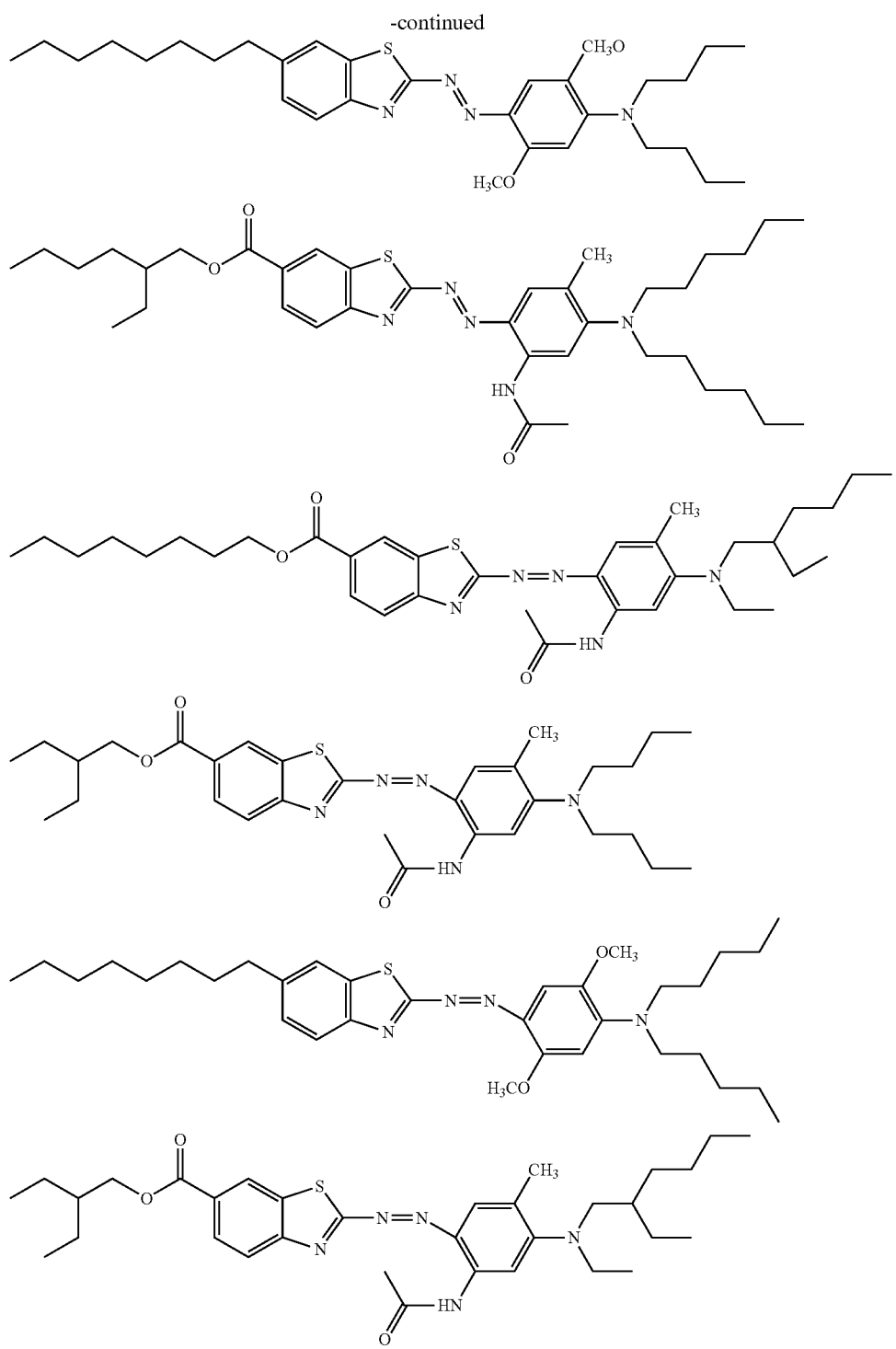
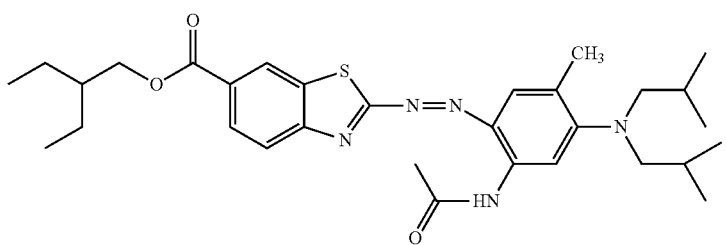

-continued
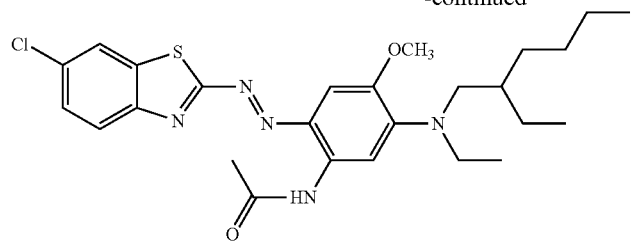
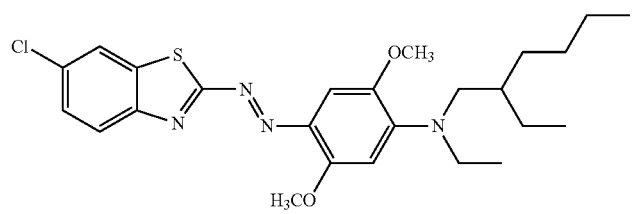
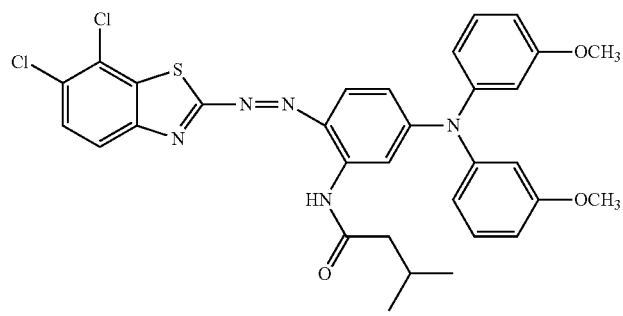
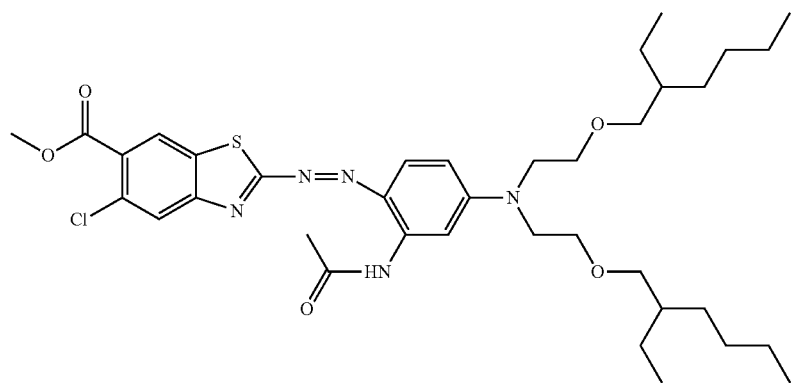
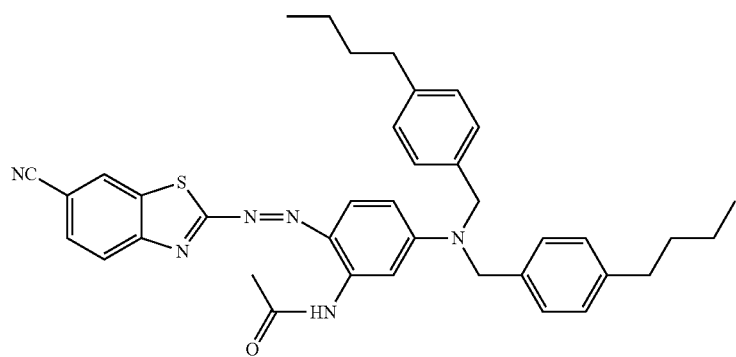

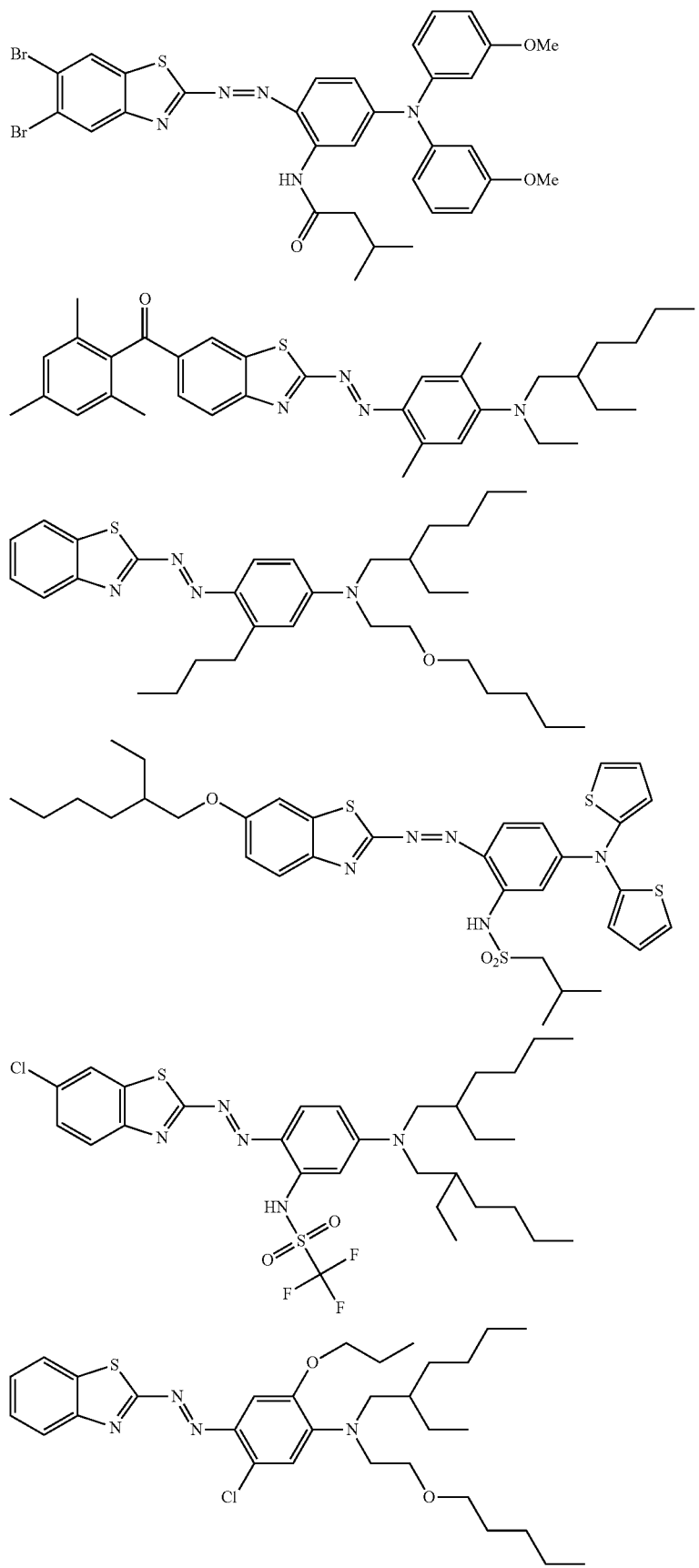

-continued

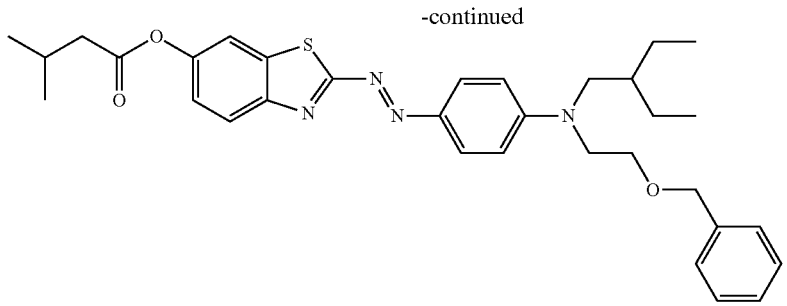

The cyclic compound represented by the general formula (V) can be synthesized, for example, in accordance with the methods described in JP-A-10-204307 and JP-A-2000-280635.

With regard to the heterocyclic compounds represented by the general formulae (III) to (V) and the like as described above, from the standpoint of the gram extinction coefficient, the molecular weight thereof is generally 2,000 or less, preferably 1,000 or less, including substituent(s) in the case where the compound has the substituent(s). Also, the molecular weight is generally 300 or more, preferably 400 or more.

Specific examples of the cyanovinyl compound are not particularly limited but a compound represented by the following general formula (VI) is preferable.

[Chem 29]

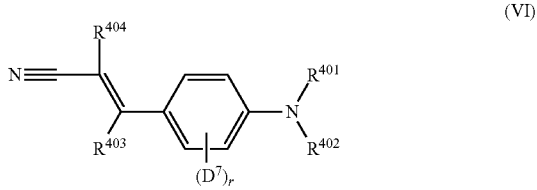

(VI)

wherein $R^{401}$, $R^{402}$, $R^{403}$, $R^{404}$, and $D^7$ each independently represent an arbitrary substituent and r represents an integer of 1 to 4, and when r is 2 or larger, two or more $D^7$ groups present in one molecule may be the same or different.

$R^{401}$ and $R^{402}$ each independently represent an arbitrary substituent. $R^{401}$ and $R^{402}$ are not particularly limited so long as they do not impair the effects of the invention but are each independently preferably an optionally substituted alkyl group having 1 to 20 carbon atoms, an optionally substituted aryl group having 6 to 20 carbon atoms, or an optionally substituted heteroaryl group having 2 to 20 carbon atoms, for a high extinction coefficient and a high solubility in solvents.

The alkyl group of each of $R^{401}$ and $R^{402}$ specifically has the same meaning as the alkyl group exemplified in $R^1$ of the above general formula (I) and each substituent which may be possessed also has the same meaning. As the alkyl group of each of $R^{401}$ and $R^{402}$, the number of carbon atoms is preferably 2 or more, more preferably 4 or more. Also, the number of carbon atoms is preferably 16 or less, more preferably 12 or less. When the number of carbon atoms falls within an appropriate range, there are cases where the compound is excellent in solubility in solvents and can have a high gram extinction coefficient.

The aryl group of each of $R^{401}$ and $R^{402}$ specifically has the same meaning as the aryl group exemplified in $R^3$ of the above general formula (I) and each substituent which may be possessed also has the same meaning as the aryl group exemplified in $R^3$ of the above general formula (I).

The heteroaryl group of each of $R^{401}$ and $R^{402}$ specifically has the same meaning as the heteroaryl group exemplified in $R^3$ of the above general formula (I) and each substituent which may be possessed also has the same meaning as the heteroaryl group exemplified in $R^3$ of the above general formula (I).

$R^{403}$ and $R^{404}$ each independently represent an arbitrary substituent. $R^{403}$ and $R^{404}$ are not particularly limited so long as they do not impair the effects of the invention but $R^{403}$ is preferably a hydrogen atom or a cyano group and $R^{404}$ is preferably a cyano group or a —$COR^{405}$ group, for a high extinction coefficient and a high solubility.

Moreover, $R^{405}$ represents an optionally substituted alkyl group having 1 to 20 carbon atoms, an optionally substituted alkoxy group having 1 to 20 carbon atoms, an optionally substituted aryl group having 6 to 20 carbon atoms, or an optionally substituted heteroaryl group having 2 to 20 carbon atoms.

The alkyl group of $R^{405}$ specifically has the same meaning as the alkyl group exemplified in $R^1$ of the above general formula (I) and the substituent which may be possessed also has the same meaning. As the alkyl group of $R^{405}$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The alkoxy group of $R^{405}$ has the same meaning as the alkoxy group exemplified in $D^1$ of the above general formula (I) and the substituent which may be possessed also has the same meaning. As the alkoxy group of $R^{405}$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The aryl group of $R^{405}$ specifically has the same meaning as the aryl group exemplified in $R^3$ of the above general formula (I) and the substituent which may be possessed also has the same meaning as the aryl group exemplified in $R^3$ of the above general formula (I).

The heteroaryl group of $R^{405}$ specifically has the same meaning as the heteroaryl group exemplified in $R^3$ of the above general formula (I) and the substituent which may be possessed also has the same meaning as the heteroaryl group exemplified in $R^3$ of the above general formula (I).

$D^7$ represents an arbitrary substituent. $D^7$ is not particularly limited so long as it does not impair the effects of the invention but is preferably, a hydrogen atom, a halogen atom, an optionally substituted alkyl group having 1 to 20 carbon atoms, an optionally substituted alkoxy group having 1 to 20 carbon atoms, an —NHCOR$^{406}$ group, or an —NHSO$_2$R$^{407}$ group, for a high extinction coefficient and a high solubility in solvents.

r represents an integer of 1 to 4, and when r is 2 or larger, two or more D$^7$ groups present in one molecule may be the same or different.

Moreover, R$^{406}$ and R$^{407}$ each independently represent an optionally substituted alkyl group having 1 to 20 carbon atoms, an optionally substituted aryl group having 6 to 20 carbon atoms, or an optionally substituted heteroaryl group having 2 to 20 carbon atoms.

The alkyl group of each of D$^7$, R$^{406}$, and R$^{407}$ specifically has the same meaning as the alkyl group exemplified in R$^1$ of the above general formula (I) and each substituent which may be possessed also has the same meaning. As the alkyl group of each of D$^7$, R$^{406}$, and R$^{407}$, the number of carbon atoms is preferably 2 or more, more preferably 4 or more. Also, the number of carbon atoms is preferably 16 or less, more preferably 12 or less. When the number of carbon atoms falls within an appropriate range, there are cases where the compound is excellent in solubility in solvents and can have a high gram extinction coefficient.

The alkoxy group of D$^7$ has the same meaning as the alkoxy group exemplified in D$^1$ of the above general formula (I) and the substituent which may be possessed also has the same meaning. As the alkoxy group of D$^7$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The aryl group of each of R$^{406}$ and R$^{407}$ specifically has the same meaning as the aryl group exemplified in R$^3$ of the above general formula (I) and each substituent which may be possessed also has the same meaning as the aryl group exemplified in R$^3$ of the above general formula (I).

The heteroaryl group of each of R$^{406}$ and R$^{407}$ specifically has the same meaning as the heteroaryl group exemplified in R$^3$ of the above general formula (I) and each substituent which may be possessed also has the same meaning as the heteroaryl group exemplified in R$^3$ of the above general formula (I).

Specific examples of the cyanovinyl compound represented by the above general formula (VI) are shown in the following but are not limited to these unless they exceed the gist thereof.

[Chem 30]

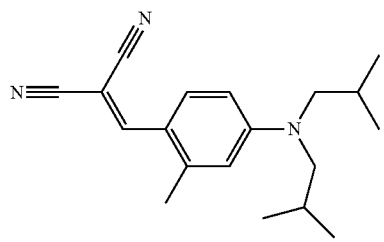

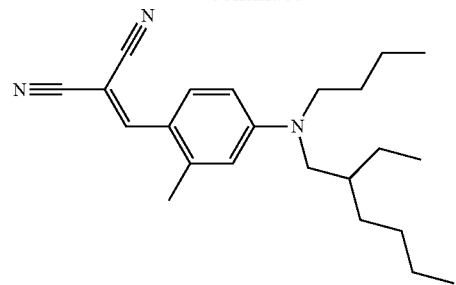

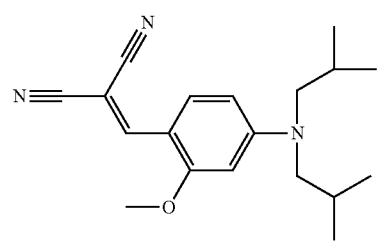

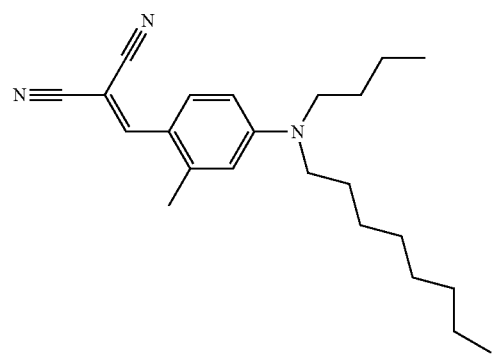

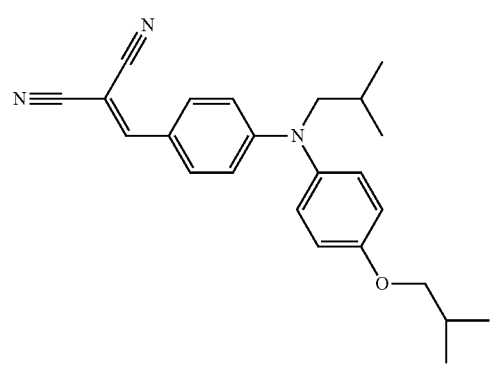

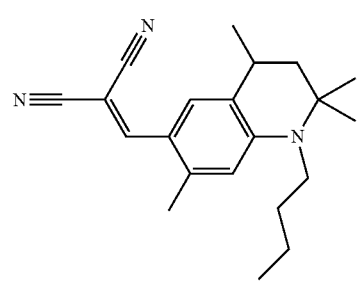

85
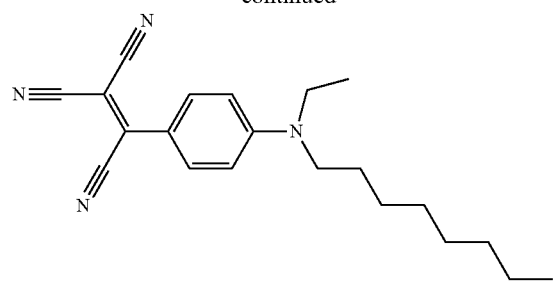
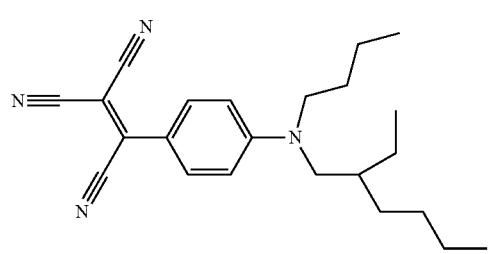
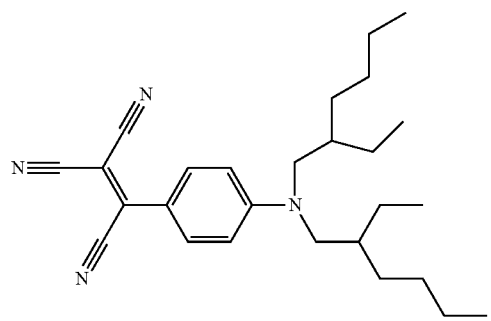
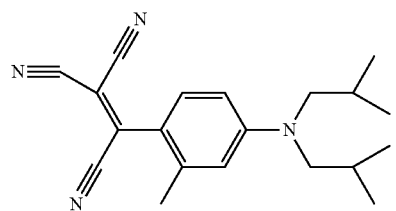
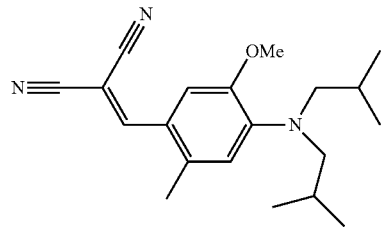
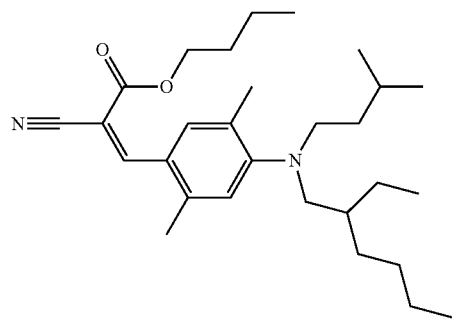
86
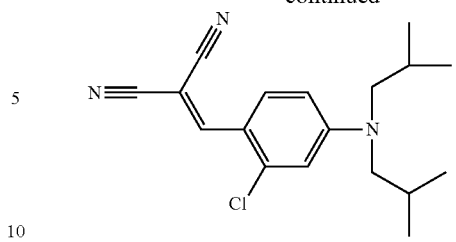
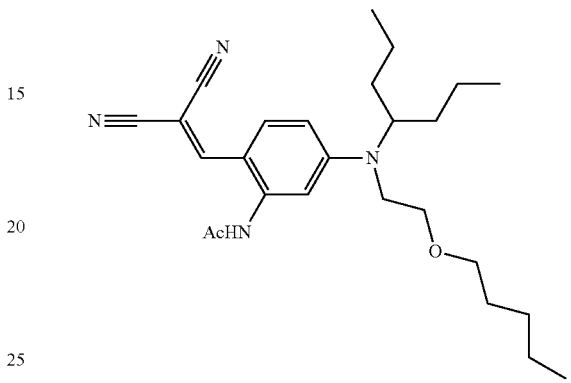
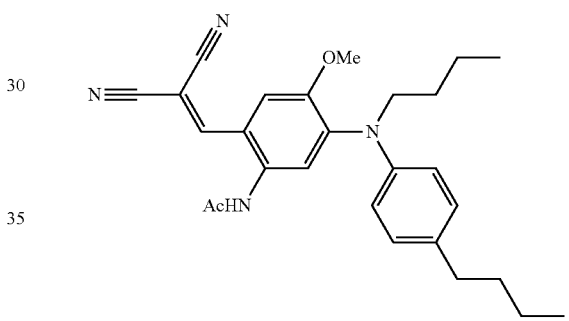
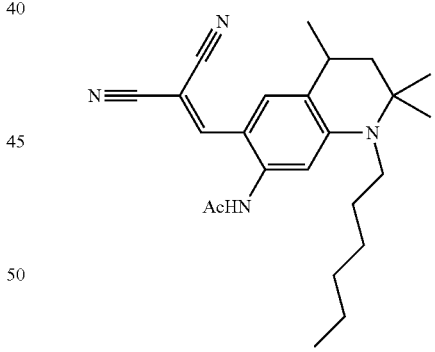
[Chem 31]
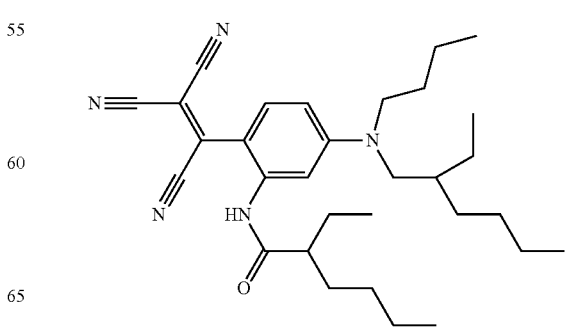

| 87 -continued | 88 -continued |
|---|---|
| 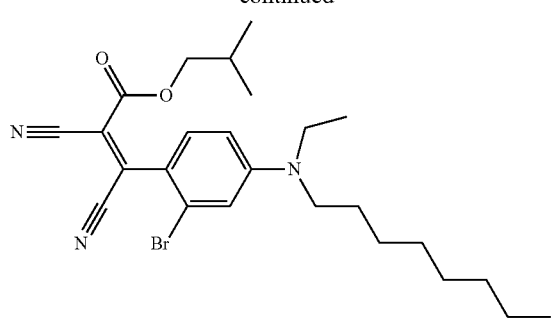 | 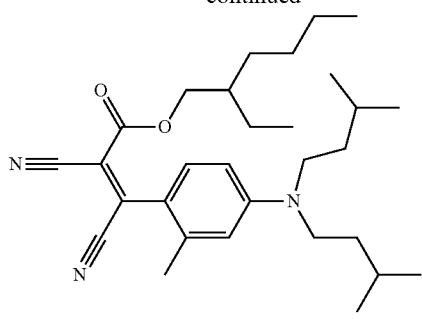 |
| 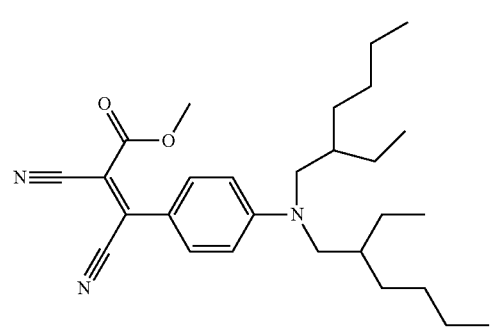 | 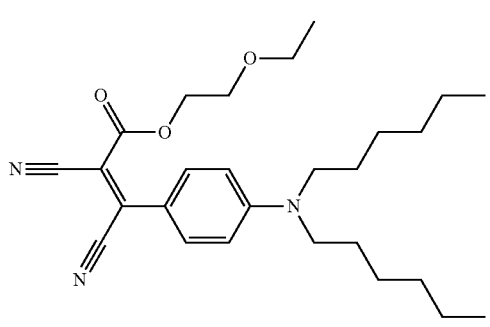 |
| 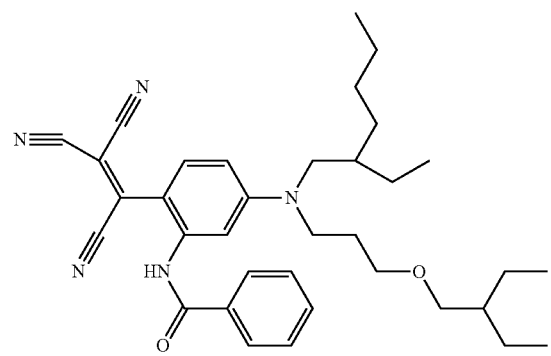 | 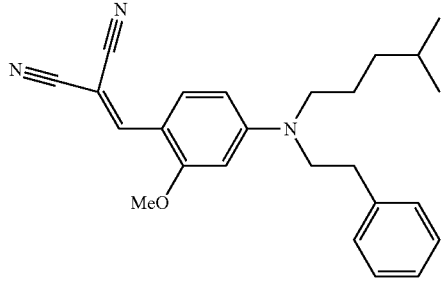 |
| 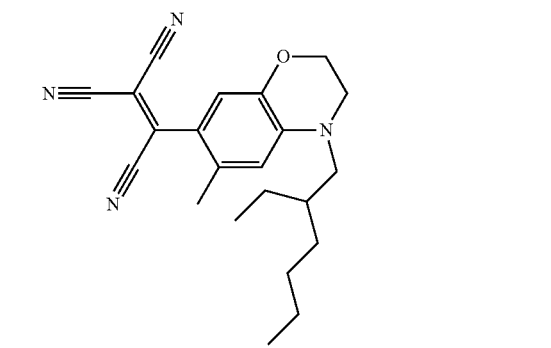 | 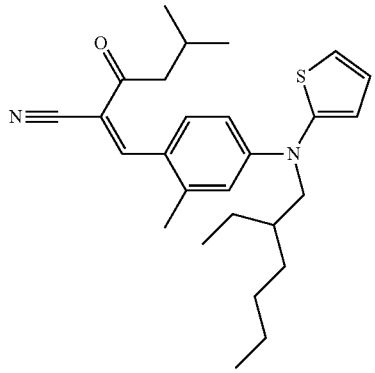 |
| 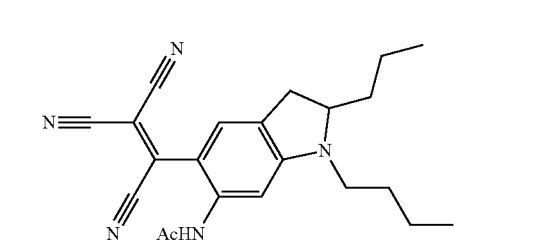 | 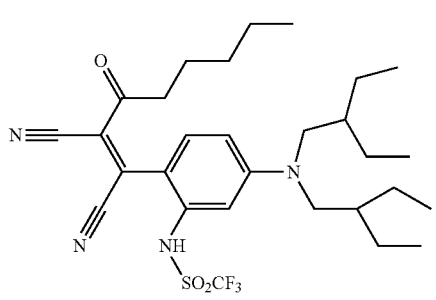 |

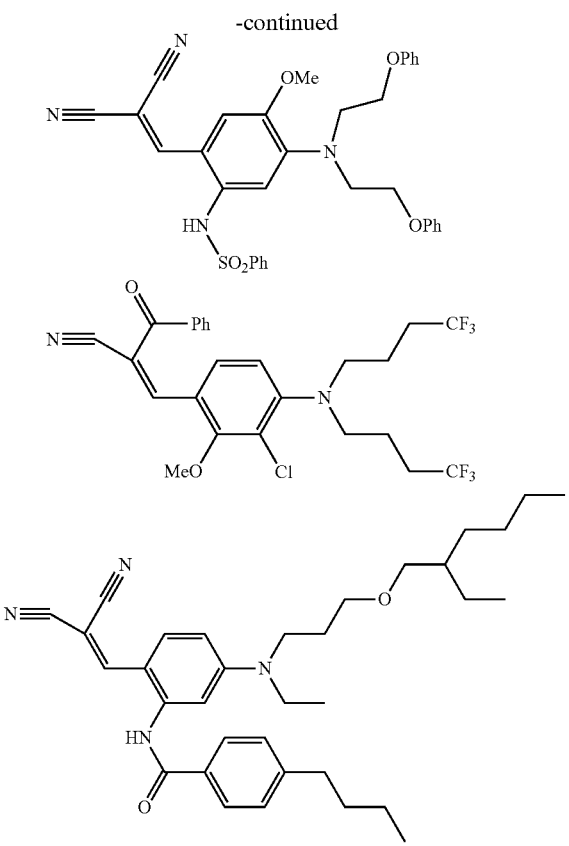

The compound represented by the above general formula (VI) can be synthesized, for example, in accordance with the methods described in JP-A-11-100523 and JP-A-2000-247942.

Specific examples of the anthraquinone compound are not particularly limited but a compound represented by the following general formula (VII) is preferable.

[Chem 32]

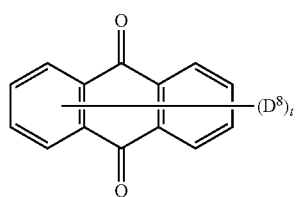

(VII)

wherein
$D^8$ each independently represent an arbitrary substituent, and t represents an integer of 1 to 8 and, when t is 2 or larger, two or more $D^8$ groups present in one molecule may be the same or different.

$D^8$ represents an arbitrary substituent. $D^8$ is not particularly limited so long as it does not impair the effects of the invention but is preferably, a hydrogen atom, a halogen atom, an optionally substituted alkyl group having 1 to 20 carbon atoms, an optionally substituted alkoxy group having 1 to 20 carbon atoms, a cyano group, a hydroxy group, an amino group, a nitro group, a —$COOR^{501}$ group, an —$NHR^{502}$ group, an —$NHCOR^{503}$ group, or an —$SR^{504}$ group, for a high extinction coefficient and a high solubility in solvents.

t represents an integer of 1 to 8, and when t is 2 or larger, two or more $D^8$ groups present in one molecule may be the same or different.

Moreover, $R^{501}$, $R^{502}$, $R^{503}$, and $R^{504}$ each independently represent an optionally substituted alkyl group having 1 to 20 carbon atoms, an optionally substituted aryl group having 6 to 20 carbon atoms, or an optionally substituted heteroaryl group having 2 to 20 carbon atoms.

The alkyl group of each of $D^8$, $R^{501}$, $R^{502}$, $R^{503}$, and $R^{504}$ specifically has the same meaning as the alkyl group exemplified in $R^1$ of the above general formula (I) and each substituent which may be possessed also has the same meaning. As the alkyl group of each of $D^8$, $R^{501}$, $R^{502}$, $R^{503}$, and $R^{504}$, the number of carbon atoms is preferably 16 or less, more preferably 10 or less, particularly preferably 6 or less. When the number of carbon atoms falls within an appropriate range, there are cases where the compound is excellent in solubility in solvents and can have a high gram extinction coefficient.

The aryl group of each of $R^{501}$, $R^{502}$, $R^{503}$, and $R^{504}$ specifically has the same meaning as the aryl group exemplified in $R^3$ of the above general formula (I) and each substituent which may be possessed also has the same meaning as the aryl group exemplified in $R^3$ of the above general formula (I). As the aryl group of each of $R^{502}$ and $R^{504}$, for the reason of high solubility in solvents, an optionally substituted phenyl group or naphthyl group is preferable.

As the substituent which may be possessed by the phenyl group or the naphthyl group, for the reason of high solubility in solvents, a halogen atom, an optionally substituted alkyl group having 1 to 10 carbon atoms, or an optionally substituted alkoxy group having 1 to 10 carbon atoms is preferable.

The heteroaryl group of each of $R^{501}$, $R^{502}$, $R^{503}$, and $R^{504}$ specifically has the same meaning as the heteroaryl group exemplified in $R^3$ of the above general formula (I) and each substituent which may be possessed also has the same meaning as the heteroaryl group exemplified in $R^3$ of the above general formula (I).

Specific examples of the anthraquinone compound represented by the above general formula (VII) are shown in the following but are not limited to these unless they exceed the gist thereof.

[Chem 33]

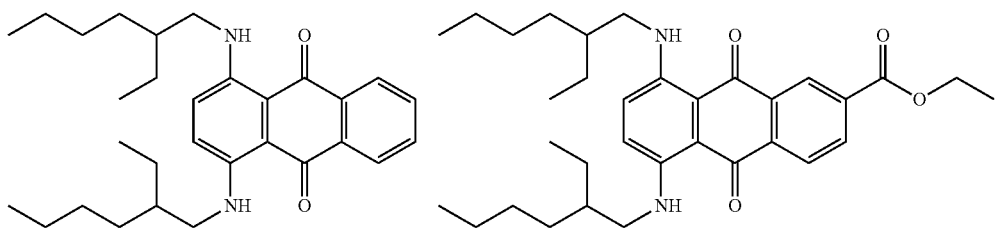

-continued
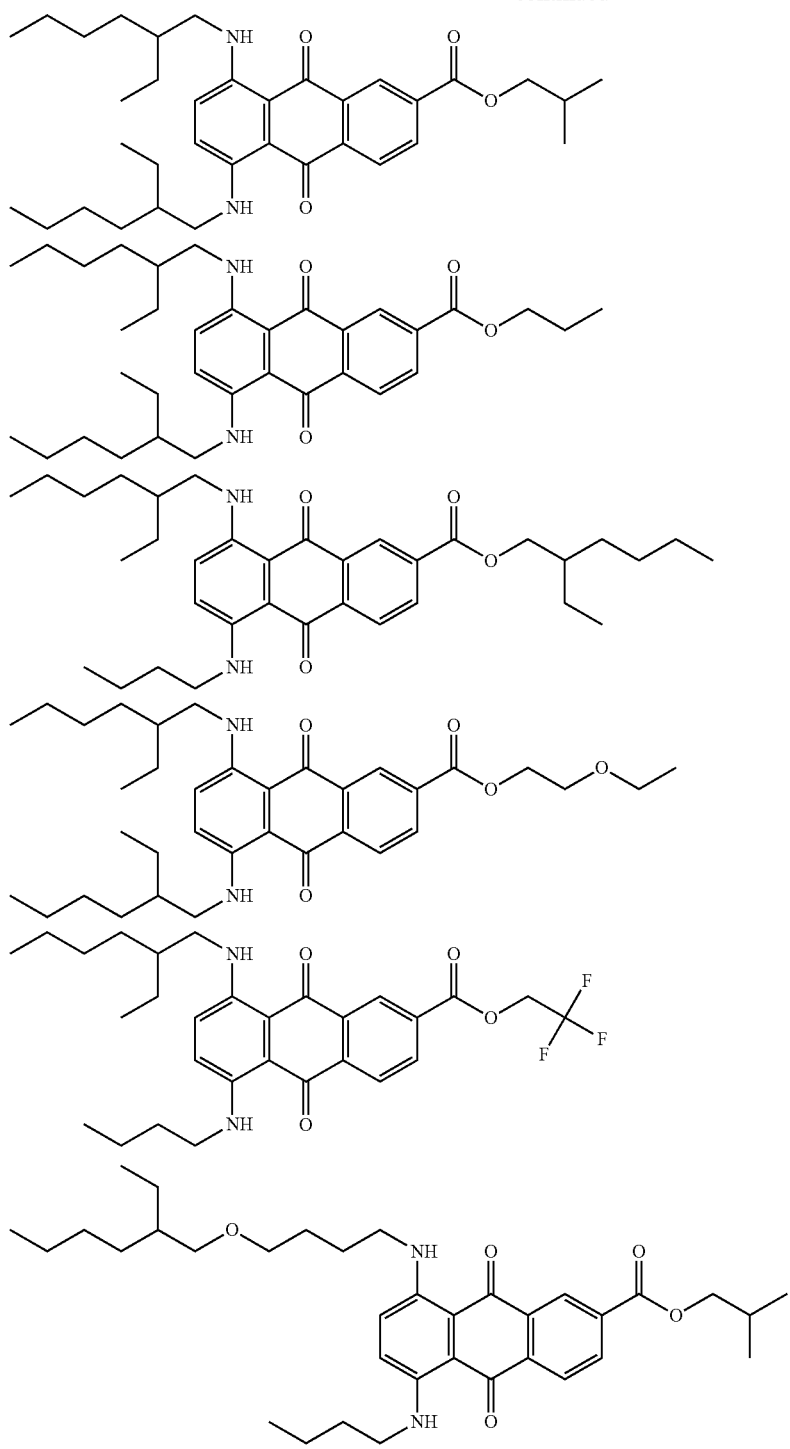
[Chem 34]
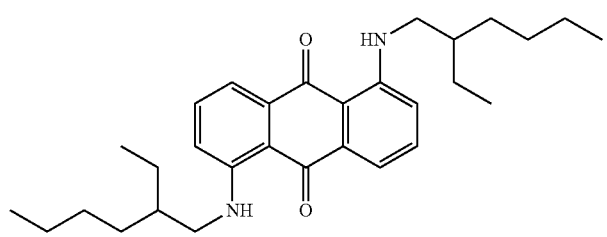

-continued
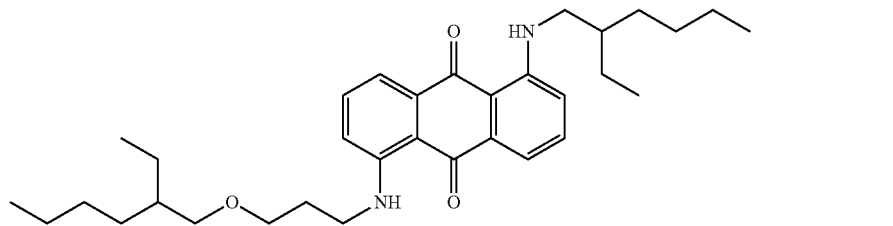
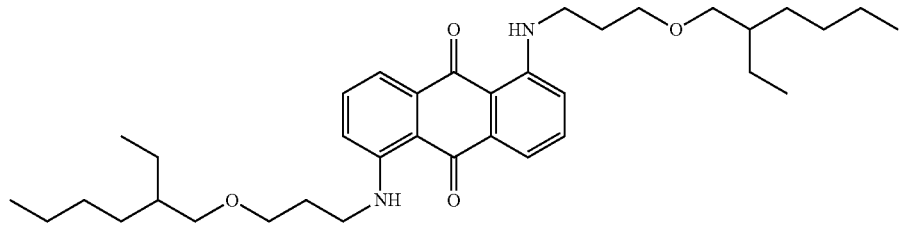
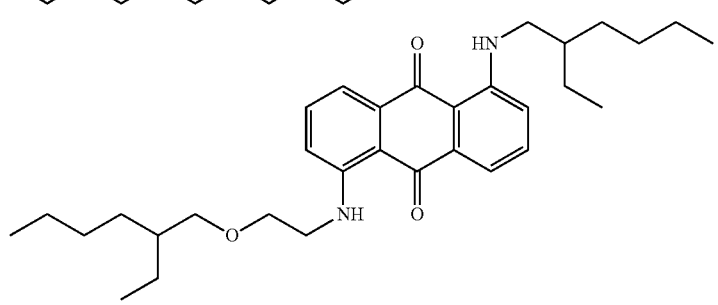
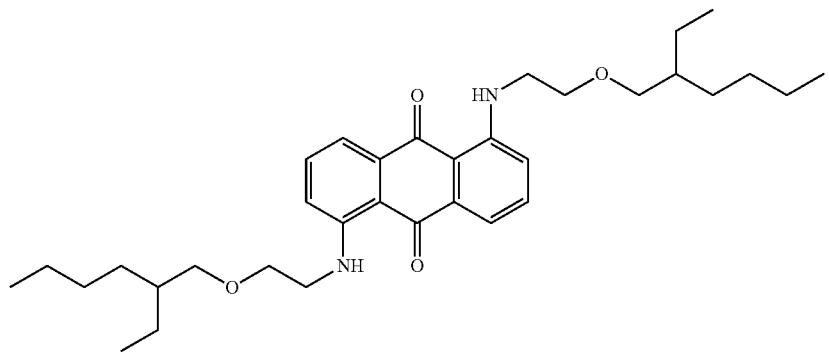
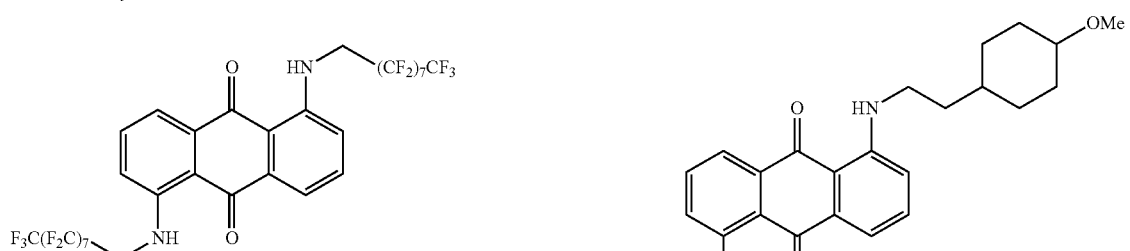
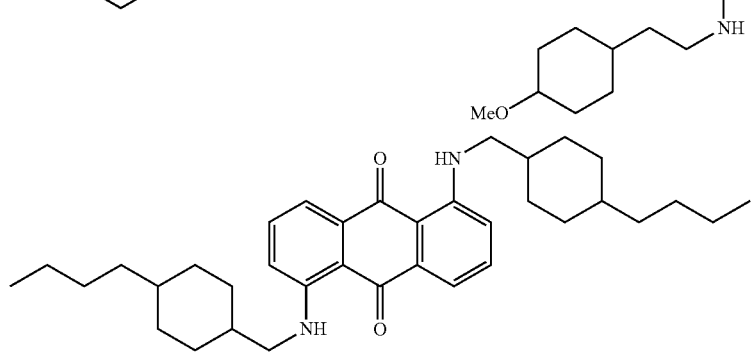

-continued
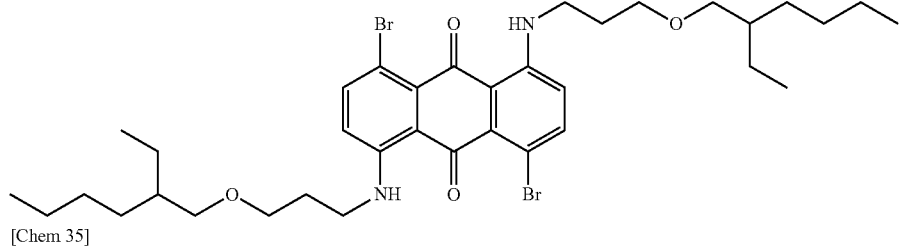
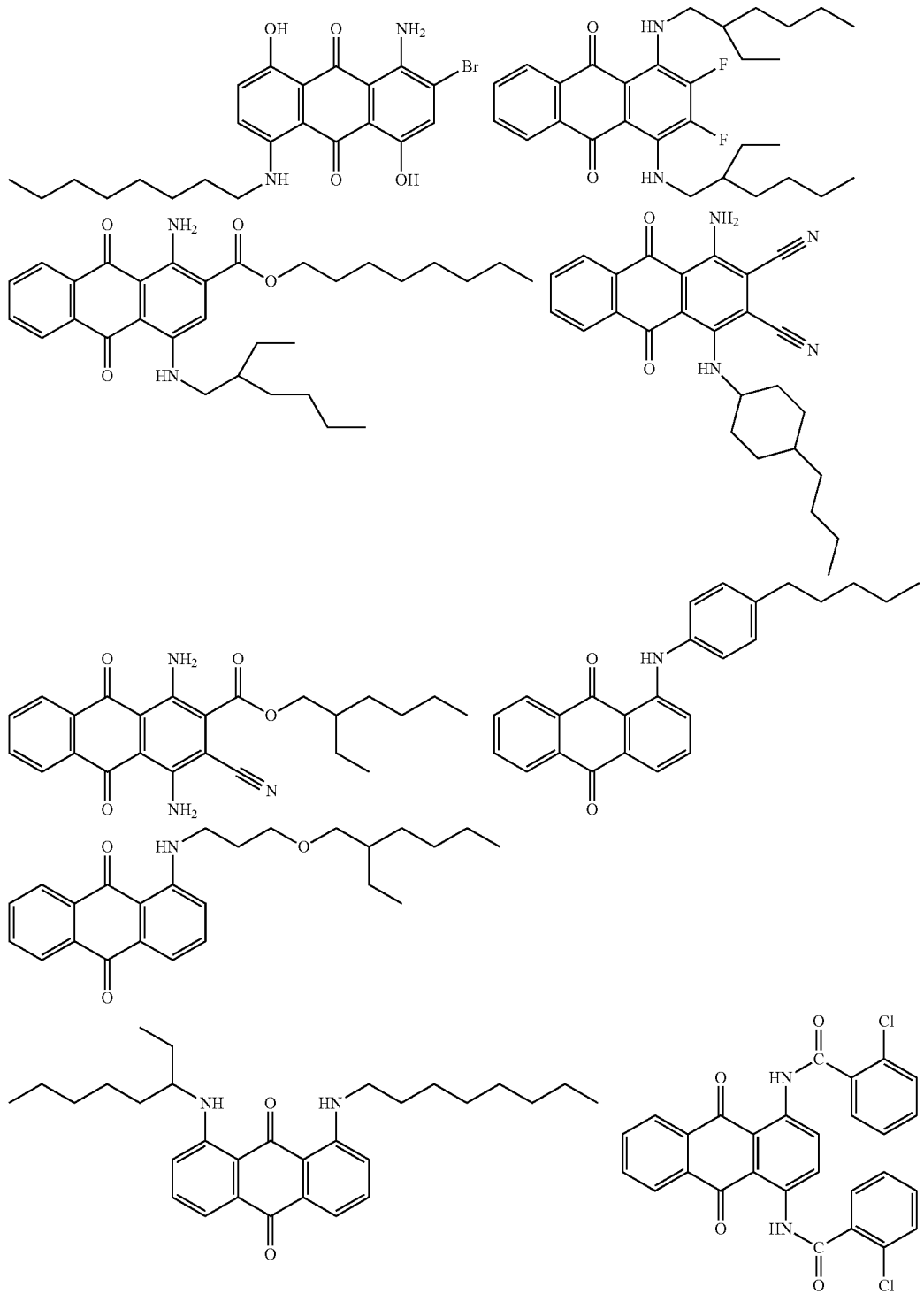

-continued
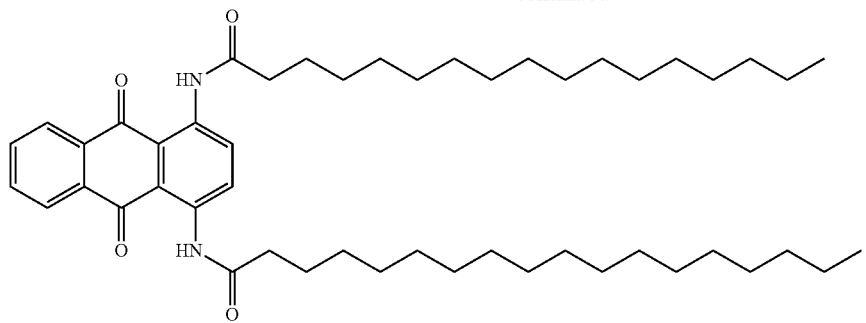
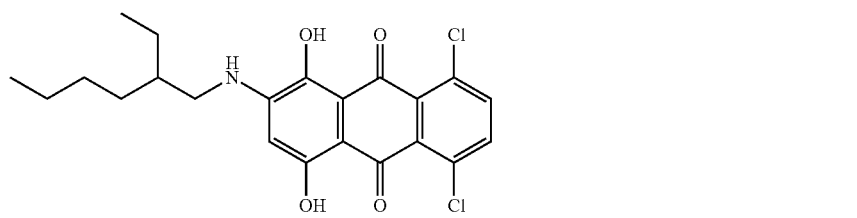
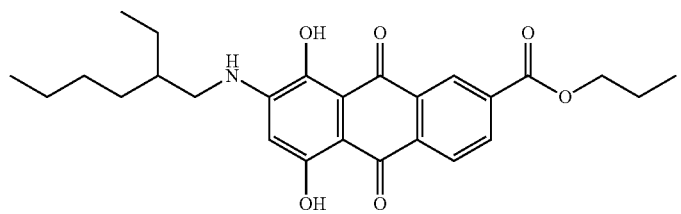
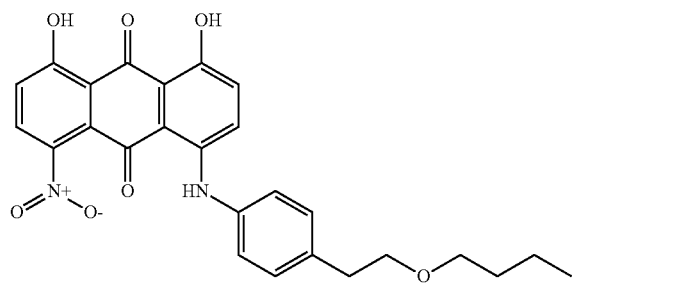
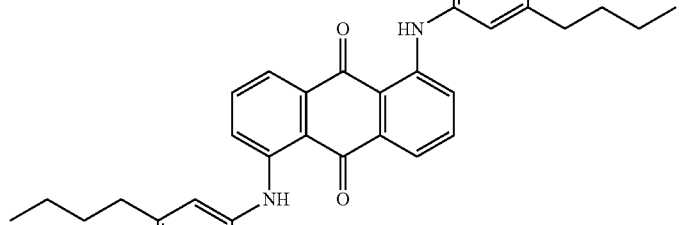
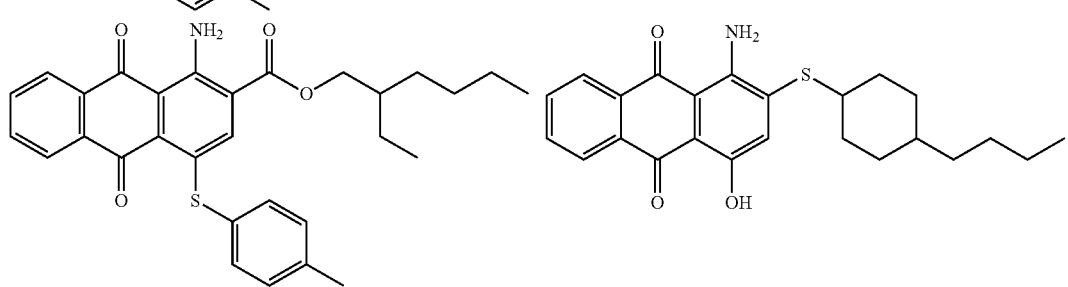

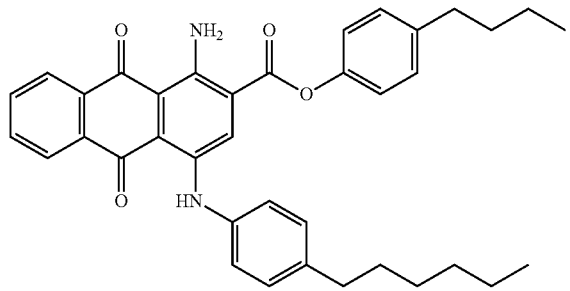
[Chem 36]
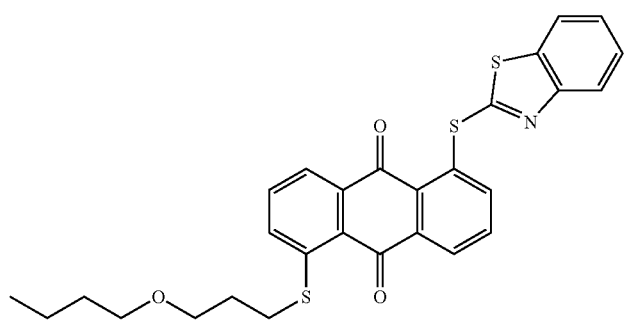
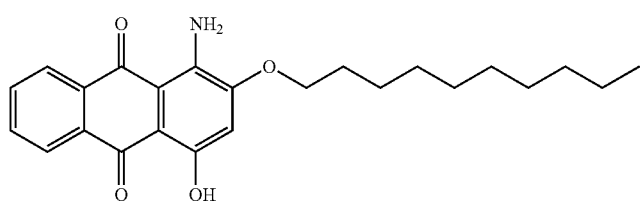
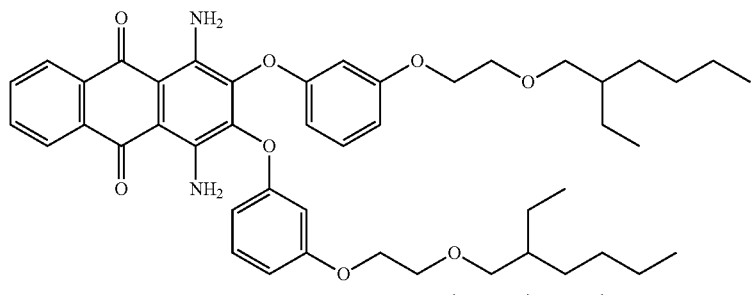
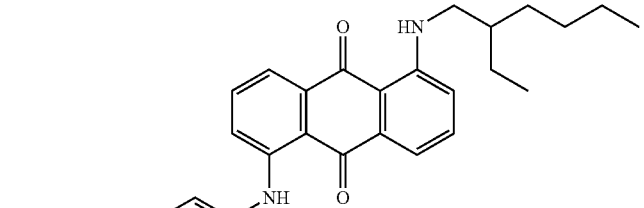
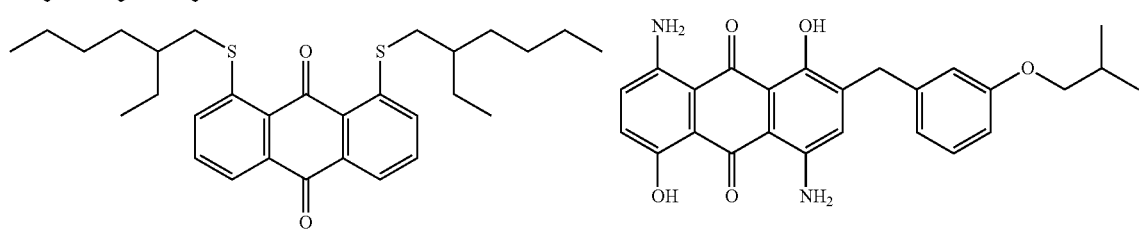

101

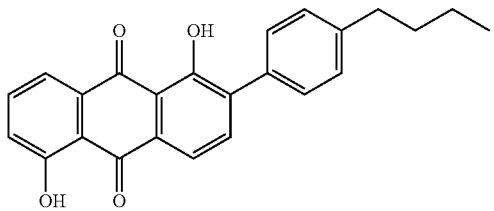

-continued

102

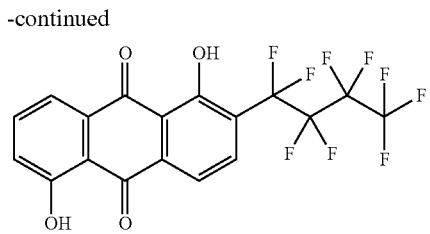

The anthraquinone compound represented by the above general formula (VII) can be synthesized, for example, in accordance with the methods described in U.S. Pat. No. 5,558,808 and JP-T-11-506151.

With regard to the anthraquinone compounds represented by the general formula (VII), from the standpoint of gram extinction coefficient, the molecular weight thereof is generally 2,000 or less, preferably 1,000 or less, including substituent(s) in the case where the compound has the substituent(s). Also, the molecular weight is generally 300 or more, preferably 400 or more.

With regard to the concentration of the compounds represented by the above general formulae (I) to (VII) in the ink containing the compounds, the ink is prepared in arbitrary concentration depending on the use purpose thereof. In the case where the compounds are used as compounds for electrowetting displays, the compounds are used in a concentration of 0.2% by mass or more after dilution with a solvent depending on a necessary εC value but the concentration is preferably 1% by mass or more, more preferably 5% by mass or more. Also, the concentration is usually preferably about 80% by mass or less.

In the case where the ink of the invention is used as a black ink, it is preferable to contain at least one of the compounds represented by the formulae (III) to (VII) in addition to the compound represented by the above general formula (I). Inclusion of these compounds makes it possible to attain a high light absorption in a wide wavelength range within the visible light region. Use of these compounds is superior in that even when these compounds are used as a mixture thereof, the solubility thereof in solvents does not decrease and the mixture show a high solubility.

Furthermore, the ink of the invention may contain any additives suitable for each application according to need within the range where the effects of the invention are not impaired.

Hue of each ink can be quantitatively evaluated in the CIE color space chromaticity coordinates L*a*b*. L* represents lightness; L*=0 indicate black and L*=100 indicate white, in terms of diffuse color. a*b* represents hue, and chroma is represented by C* that is determined by $C^*=\sqrt{(a^{*2}+b^{*2})}$ from a*b*. The value of C* indicates the following: the closer to 0 the value is, the more the color is achromatic.

Incidentally, in the case where hue of a black ink is evaluated, in the measurement by a spectrophotometer, it is necessary to reduce optical path length for measurement for obtaining suitable transmitted light intensity in the case of an ink having an extremely high blackness. In this case, since the transmitted light increases when the optical path length for measurement is reduced, the value of lightness L* to be measured apparently increases. Therefore, in the case where the values of L* measured in cells different in the optical path length for measurement are compared, it is necessary to note that actual blackness is sometimes higher than the apparent L* in the ink measured in a cell having a small optical path length for measurement.

In the case where the ink of the invention is used as a black ink, the ink shows a preferable hue since the values of L* and C* are close to 0. When measured using a cell having an optical path length for measurement of 0.004 mm, C* is preferably 20 or less, more preferably 10 or less. There is no lower limit thereon and a value closer to 0 is preferable. Moreover, when similarly measured using a cell having an optical path length for measurement of 0.004 mm, the value of L* is preferably 20 or less, preferably 15 or less. There is no lower limit thereon and a value closer to 0 is preferable.

(Applications)

The ink of the invention is suitably used as an ink for displays. As the displays, the ink is especially useful in a display which has a display part containing an ink and in which an image is displayed by controlling voltage application to the display part, a display in which an image is displayed by changing a colored state by means of voltage application, and a display in which an image is displayed further using electrophoretic particles or an aqueous medium in the display part.

As the display in which an image is displayed by changing a colored state by means of voltage application, for example, there may be mentioned one in which the color is changed and the image is displayed through movement, such as development or aggregation, of a colored or colorless ink or a solvent by means of voltage application but the display is not limited thereto.

The electrophoretic particles are charged particles and may have a color. Multiple kinds of electrophoretic particles may be contained in the display part. Meanwhile, the aqueous medium is a fluid which may have a color, and the display part may have multiple kinds of aqueous media. The aqueous medium includes water, non-charged liquids, liquids having an affinity for water, and liquids which are akin to water in surface tension. Examples thereof include alcohols, liquids which contain an inorganic salt, e.g., an alkali metal halide, and the like.

Furthermore, the azo compound and ink of the invention are particularly useful as inks for use in electrowetting type displays or electrophoresis type displays.

It is also possible to provide a satisfactory ink having an excellent hue, such as black, by combining the azo compound of the invention with other compound(s). For example, the black ink is useful also as a member which functions as an optical shutter.

Although usable in any display device which has a display, the ink of the invention is especially useful in electronic paper.

Examples of display technologies include the electrowetting system and the electrophoretic system. Applications of such displays include various displays for computers, for electronic paper, and for electronic inks. There is a possibility that such displays might be capable of replacing most of the current liquid-crystal display applications. Of these, it is especially preferred to use the ink of the invention as an ink for electrowetting displays.

EXAMPLES

The invention will be explained below in more detail with reference to Examples and Comparative Examples, but the invention should not be construed as being limited to the following Examples.

<Synthesis of Intermediate M-1>

After 4-n-butylaniline (8.02 g, 54 mmol) and an aqueous 7% hydrochloric acid solution (80 ml) were stirred and cooled with ice, an aqueous solution containing sodium nitrite (3.76 g, 55 mmol) dissolved in 25 ml of water was added dropwise thereto and the whole was stirred to form a diazo solution. Into another vessel were introduced 2-amino-3-cyanothiophene (6.68 g, 54 mmol) and methanol (100 ml), and then the diazo solution was added dropwise thereto on an ice bath to achieve coupling. The formed precipitate was taken out by filtration and dried to obtain M-1 (14 g, yield 92%).

[Chem 37]

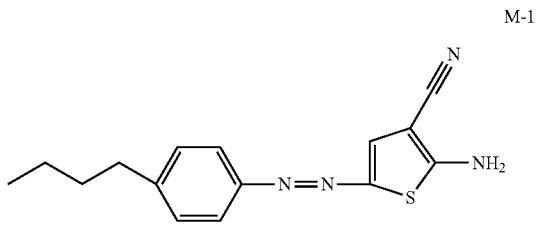

M-1

<Synthesis of Intermediate M-2>

After 4-n-amylaniline (10.0 g, 61 mmol) and an aqueous 7% hydrochloric acid solution (100 ml) were stirred and cooled with ice, an aqueous solution containing sodium nitrite (4.23 g, 61 mmol) dissolved in water (40 ml) was added dropwise thereto and the whole was stirred to form a diazo solution. Into another vessel were introduced 2-amino-3-cyanothiophene (7.60 g, 61 mmol) and methanol (120 ml), and then the diazo solution was added dropwise thereto on an ice bath to achieve coupling. The formed precipitate was taken out by filtration and dried to obtain M-2 (18.3 g, yield 100%).

[Chem 38]

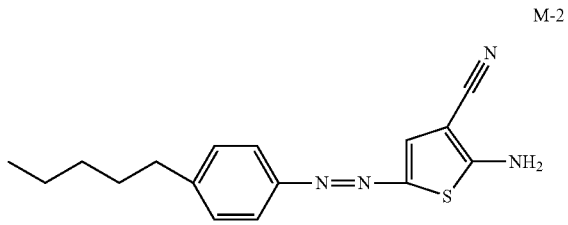

M-2

<Synthesis of Intermediate M-3>

After isobutyl 4-aminobenzoate (5.00 g, 26 mmol) and an aqueous 7% hydrochloric acid solution (50 ml) were stirred and cooled with ice, an aqueous solution containing sodium nitrite (1.78 g, 26 mmol) dissolved in water (20 ml) was added dropwise thereto and the whole was stirred to form a diazo solution. Into another vessel were introduced 2-amino-3-cyanothiophene (3.21 g, 26 mmol) and methanol (60 ml), and then the diazo solution was added dropwise thereto on an ice bath to achieve coupling. The formed precipitate was taken out by filtration and dried to obtain M-3 (8.50 g, yield 100%).

[Chem 39]

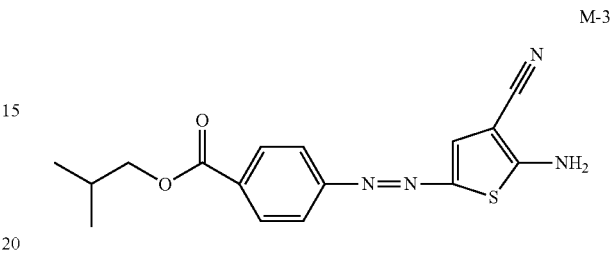

M-3

<Synthesis of Intermediate M-4>

After (2-ethyl)hexyl 4-aminobenzoate (6.22 g, 25 mmol) and an aqueous 7% hydrochloric acid solution (39 ml) were stirred and cooled with ice, an aqueous solution containing sodium nitrite (1.74 g, 25 mmol) dissolved in water (12 ml) was added dropwise thereto and the whole was stirred to form a diazo solution. Into another vessel were introduced 2-amino-3-cyanothiophene (2.86 g, 23 mmol) and methanol (50 ml), and then the diazo solution was added dropwise thereto on an ice bath to achieve coupling. The formed precipitate was taken out by filtration and dried to obtain M-4 (6.04 g, yield 63%).

[Chem 40]

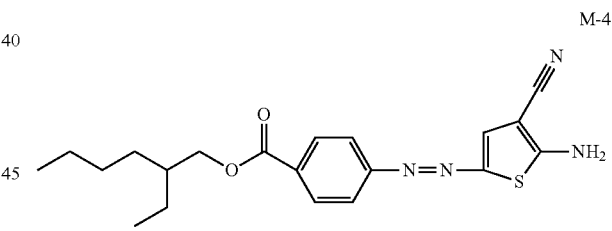

M-4

<Synthesis of Intermediate M-5>

4-Butoxyaniline (5.0 g, 30 mmol) was dissolved in 7% hydrochloric acid (50 ml) and the whole was cooled on an ice bath. Then, an aqueous solution (10 ml) of sodium nitrite (2.2 g, 32 mmol) was added dropwise thereto while keeping the internal temperature at 0 to 2° C. and the whole was stirred at the same temperature for 60 minutes to obtain a diazo solution. Into another vessel were placed 2-amino-4-methylthiazole (3.5 g, 30 ml), methanol (60 ml), and urea (0.18 g), and then the diazo solution was added dropwise thereto under cooling with an ice bath while keeping the internal temperature at 5° C. or lower. The mixture was neutralized with sodium acetate, water was added thereto, insoluble matter was taken out by filtration and washed with a mixed solvent of methanol/water=9/1 (volume ratio) and methanol, sequentially, to obtain the intermediate M-5 (7.69 g).

[Chem 41]

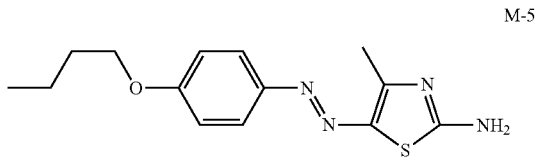

M-5

<Synthesis of Intermediate C-1>

A mixture of m-aminoacetanilide (13.0 g, 87 mmol), N,N-dimethylformamide (60 ml), 1-bromo-2-ethylhexane (50.4 g, 261 mmol), and potassium carbonate (49.5 g, 358 mmol) was stirred at 140° C. for 14 hours. After being allowed to cool, the mixture was filtered and water was added to the filtrate, followed by extraction with toluene.

The resulting organic layer was concentrated and then purified by silica gel column chromatography to obtain C-1 (17.4 g, yield 54%).

[Chem 42]

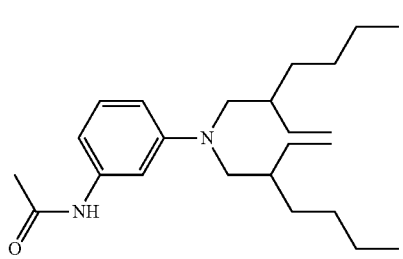

C-1

<Synthesis of Intermediate C-2>

A mixture of 3-ethylaniline (10.0 g, 83 mmol), N,N-dimethylformamide (50 ml), 1-bromo-2-ethylhexane (47.8 g, 248 mmol), and potassium carbonate (45.6 g, 330 mmol) was stirred at 110° C. for 24 hours. After being allowed to cool, the mixture was filtered and water was added to the filtrate, followed by extraction with toluene. The resulting organic layer was concentrated and then purified by silica gel column chromatography to obtain C-2 (6.3 g, yield 22%).

[Chem 43]

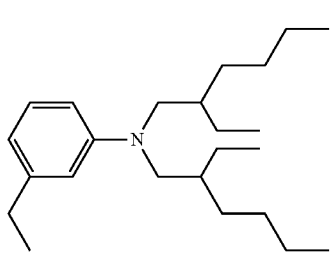

C-2

<Synthesis of Intermediate C-3>

A mixture of 3-isopropylaniline (10.0 g, 74 mmol), N,N-dimethylformamide (50 ml), 1-bromo-2-ethylhexane (42.8 g, 220 mmol), and potassium carbonate (40.9 g, 300 mmol) was stirred at 140° C. for 20 hours. After being allowed to cool, the mixture was filtered and water was added to the filtrate, followed by extraction with toluene. The resulting organic layer was concentrated and then purified by silica gel column chromatography to obtain C-3 (8.56 g, yield 32%).

[Chem 44]

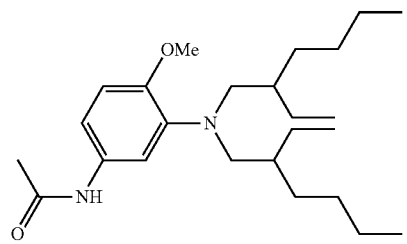

C-3

<Synthesis of Intermediate C-4>

A mixture of 3'-amino-4'-methoxyacetanilide (25.0 g, 139 mmol), N,N-dimethylformamide (125 ml), 1-bromo-2-ethylhexane (80.4 g, 416 mmol), and potassium carbonate (76.7 g, 554 mmol) was stirred at 140° C. for 14 hours. After being allowed to cool, the mixture was filtered and water was added to the filtrate, followed by extraction with toluene. The resulting organic layer was concentrated and then purified by silica gel column chromatography to obtain C-4 (9.82 g, yield 18%).

[Chem 45]

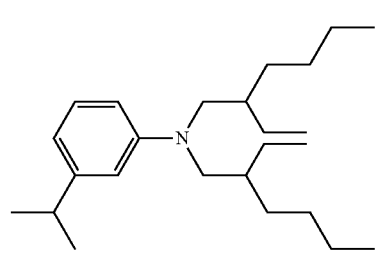

C-4

<Synthesis of Intermediate C-5>

A mixture of m-toluidine (51.1 g, 477 mmol), 1-bromo-2-ethylhexane (357.3 g, 1.86 mol), and potassium carbonate (221.5 g, 1.6 mol) was stirred at 140° C. for 17 hours. After being allowed to cool, the mixture was filtered and the resulting organic layer was concentrated and then purified by silica gel column chromatography to obtain C-5 (52 g, yield 33%).

[Chem 46]

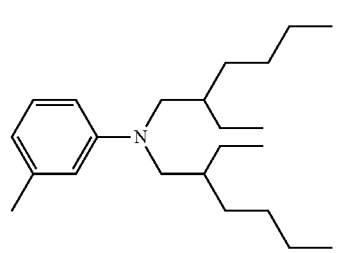

C-5

<Synthesis of Intermediate C-6>

A mixture of 2-methoxy-5-methylaniline (25.3 g, 184 mmol), N,N-dimethylformamide (100 ml), 1-bromo-2-ethylhexane (145.2 g, 752 mmol), and potassium carbonate (90.1 g, 652 mmol) was stirred at 130° C. for 6 hours. After being allowed to cool, the mixture was filtered and water was added to the filtrate, followed by extraction with toluene. The resulting organic layer was concentrated and then purified by silica gel column chromatography to obtain C-6 (11.76 g, yield 18%).

[Chem 47]

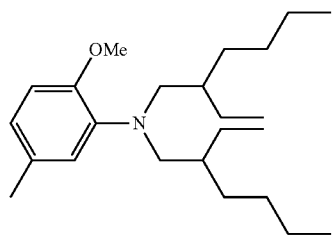

C-6

<Synthesis of Intermediate C-7>

Under ice cooling, 2-ethylhexanoyl chloride (19 ml, 111 mmol) was added dropwise to a mixture of 1,3-phenylenediamine (10 g, 93 mmol), tetrahydrofuran (THF) (125 ml), and triethylamine (30 ml, 231 mmol). After the reaction mixture was filtered, the resulting filtrate was concentrated and then purified by silica gel column chromatography. A mixture of the resulting monoamide compound (10.0 g), dimethylformamide (50 ml), 1-bromo-2-ethylhexane (21 ml, 120 mmol), and potassium carbonate (22 g, 160 mmol) was stirred at 140° C. for 24 hours. After being allowed to cool, the mixture was filtered and water was added to the filtrate, followed by extraction with toluene. The resulting organic layer was concentrated and then purified by silica gel column chromatography to obtain C-7 (5.2 g, yield 27%).

[Chem 48]

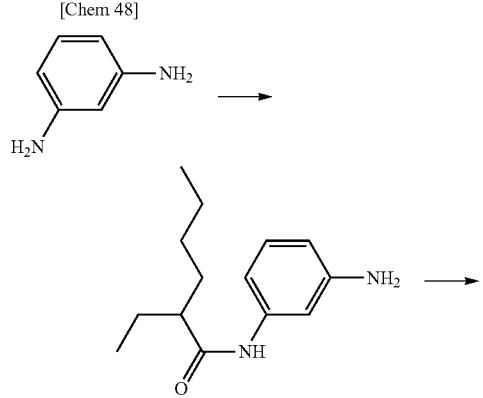

C-7

<Synthesis of Intermediate C-8>

A mixture of the intermediate C-3 (5.0 g, 12.4 mmol), methanol (10 ml), desalted water (30 ml), and 35% hydrochloric acid (3 ml) was stirred at 60° C. for 3 hours. After 35% hydrochloric acid (3 ml) was additionally added thereto, the mixture was further stirred at 60° C. for 3 hours. After 35% hydrochloric acid (1 ml) was additionally added thereto, the mixture was further stirred at 60° C. for 1.5 hours. Into another vessel were introduced sodium acetate (14 g) and desalted water (200 ml), the reaction mixture was added dropwise thereto under ice cooling. The pH was adjusted to 6.1 by additionally adding sodium acetate (50 g). The resulting mixture was extracted with a mixture of hexane and ethyl acetate and the organic layer was washed with desalted water. The organic layer was separated, dried with anhydrous sodium sulfate, and concentrated under reduced pressure to obtain an oily product (4.6 g, yield: quantitative).

To the oily product (4.5 g, 12 mmol) obtained were added N,N-dimethylformamide (45 ml), triethylamine (3.9 ml, 31 mmol), propionic acid (1.1 ml, 15 mmol), and 1-ethyl-3-(3-dimethylaminopropyl)carbodiimide hydrochloride (2.4 g, 12 mmol). After the mixture was stirred at room temperature for 16 hours, propionic acid (1.1 ml, 15 mmol) and 1-ethyl-3-(3-dimethylaminopropyl)carbodiimide hydrochloride (2.4 g, 12 mmol) were added thereto. After the mixture was stirred for 23 hours, propionic acid (20 ml) and 1-ethyl-3-(3-dimethylaminopropyl)carbodiimide hydrochloride (10 g) were added thereto, followed by stirring for 45 hours. Hexane and water were added to the reaction mixture and the organic layer was separated, washed with water, and concentrated under reduced pressure. The resulting concentrate was purified by silica gel column chromatography to obtain the intermediate C-8 (1.1 g).

[Chem 49]

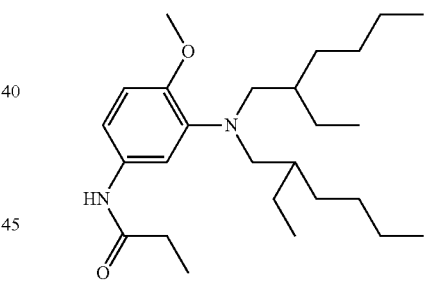

C-8

<Synthesis of Intermediate C-9>

The intermediate C-9 was synthesized from 3-chloroaniline and 1-bromo-2-ethylhexane in the same manner as in the synthesis of the intermediate C-5.

[Chem 50]

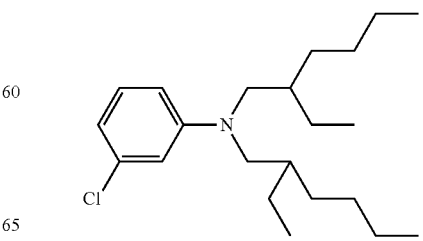

C-9

<Synthesis of Intermediate C-10>

A mixture of N-(3-aminophenyl)propanamide (10.0 g, 61 mmol), N,N-dimethylformamide (50 ml), 1-bromo-2-ethylhexane (35.3 g, 183 mmol), and potassium carbonate (33.7 g, 244 mmol) was stirred at 110° C. for 24 hours. After being allowed to cool, the mixture was filtered and water was added to the filtrate, followed by extraction with toluene. The resulting organic layer was concentrated and then purified by silica gel column chromatography to obtain C-10 (7.6 g, yield 32%).

[Chem 51]

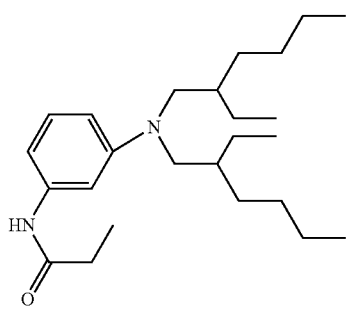

C-10

Example 1

<Synthesis of Compound 1>

While glacial acetic acid (11.4 ml) and 85% phosphoric acid (11.4 ml) were cooled with ice, M-1 (1.3 g, 4.5 mmol) was introduced into the system, 44% nitrosylsulfuric acid (1.6 g) was added dropwise thereto, and the whole was stirred to form a diazo solution. Into another vessel were introduced C-1 (1.7 g, 4.4 mmol), THF (28 ml), and water (50 ml), and the whole was placed on an ice bath. The diazo solution was added dropwise thereto to achieve coupling. The formed precipitate was taken out by filtration and then purified by silica gel column chromatography to obtain the compound 1 (0.535 g, yield 18%).

Example 2

<Synthesis of Compound 2>

The compound 2 was synthesized from the intermediate M-3 and the intermediate C-2 in the same manner as in the synthesis of the compound 1.

Example 3

<Synthesis of Compound 3>

The compound 3 was synthesized from the intermediate M-1 and the intermediate C-3 in the same manner as in the synthesis of the compound 1.

Example 4

<Synthesis of Compound]4

The compound 4 was synthesized from the intermediate M-3 and the intermediate C-4 in the same manner as in the synthesis of the compound 1.

Example 5

<Synthesis of Compound 5>

The compound 5 was synthesized from the intermediate M-2 and the intermediate C-3 in the same manner as in the synthesis of the compound 1.

Example 6

<Synthesis of Compound 6>

The compound 6 was synthesized from the intermediate M-4 and the intermediate C-5 in the same manner as in the synthesis of the compound 1.

Example 7

<Synthesis of Compound 7>

The compound 7 was synthesized from the intermediate M-1 and the intermediate C-6 in the same manner as in the synthesis of the compound 1.

Example 8

<Synthesis of Compound 8>

The compound 8 was synthesized from the intermediate M-4 and the intermediate C-1 in the same manner as in the synthesis of the compound 1.

Example 9

<Synthesis of Compound 9>

[Chem 52]

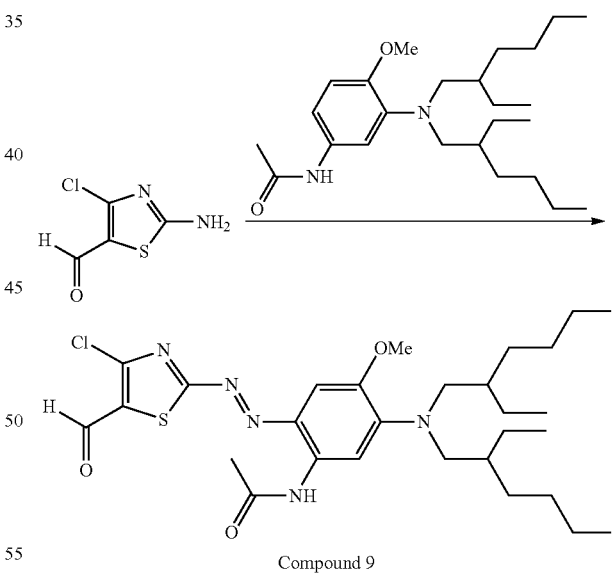

Compound 9

While 2-amino-4-chloro-5-formylthiazole (2.1 g, 12.9 mmol), glacial acetic acid (12.6 ml), and propionic acid (2.9 ml) were cooled with ice, sulfuric acid (11.3 ml), desalted water (1.3 ml), and 44 wt % nitrosylsulfuric acid (4.1 g, 14.2 mmol) were added dropwise thereto and the whole was stirred to form a diazo solution. Into another vessel were introduced C-3 (5.2 g, 12.9 mmol), THF (20 ml), sodium acetate (22.0 g), sulfamic acid (0.25 g), and water (60 ml), and the whole was placed on an ice bath. The diazo solution was added dropwise thereto to achieve coupling. The formed precipitate was taken out by filtration and then purified by silica gel column chromatography to obtain the compound 9 (1.92 g, yield 26%).

Example 10

<Synthesis of Compound 10>

[Chem 53]

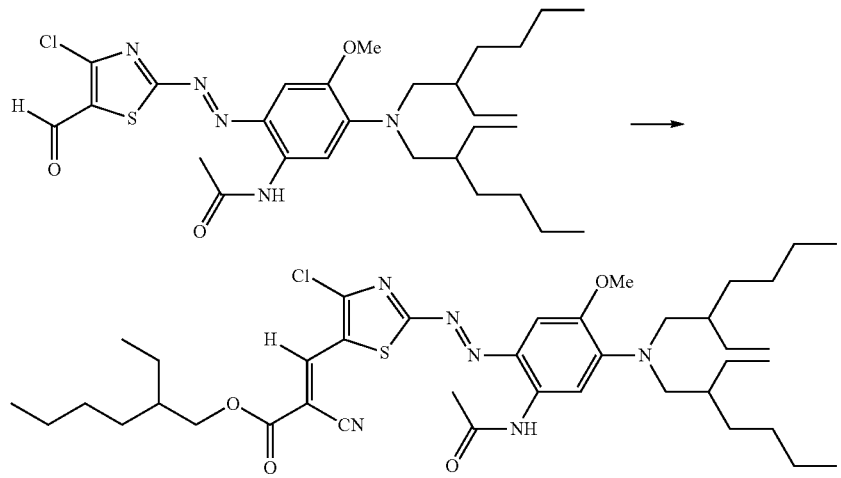

The compound 9 (0.80 g, 1.4 mmol) was dissolved in 2-ethylhexyl alcohol (8.0 ml). While a mixture thereof with 2-ethyl cyanoacetate (300 mg) was stirred at room temperature, 0.3 equivalent amount of pyridine to the raw material was dissolved in 2-ethylhexyl alcohol and then added thereto. The reaction mixture was added dropwise to water, filtered, washed with water, and then purified by silica gel column chromatography (0.32 g, yield 32%).

Example 11

<Synthesis of Compound 11>

While 2-amino-3-cyano-4-chloro-5-formylthiophene (0.5 g, 2.1 mmol), glacial acetic acid (3 ml), and propionic acid (0.7 ml) were cooled with ice, sulfuric acid (2.7 ml), desalted water (0.3 ml), and 44 wt % nitrosylsulfuric acid (0.7 g, 2.3 mmol) were added dropwise thereto and the whole was stirred to form a diazo solution. Into another vessel were introduced C-7 (0.95 g, 2.0 mmol), THF (5 ml), sodium acetate (5.7 g), sulfamic acid (0.06 mg), and water (20 ml), and the whole was placed on an ice bath. The diazo solution was added dropwise thereto to achieve coupling. The formed precipitate was taken out by filtration and then purified by silica gel column chromatography to obtain a blue compound.

While a mixture of the resulting blue compound (0.30 g, 0.5 mmol), n-BuOH (3.0 ml), and malononitrile (33 mg) was stirred at room temperature, 0.3 equivalent amount of pyridine to the raw material was dissolved in n-BuOH and then added thereto. The reaction mixture was added dropwise to water, filtered, washed with water, and then purified by silica gel column chromatography to obtain the compound 11 (0.15 g, yield 46%).

Example 12

<Synthesis of Compound 12>

While a mixture of 2-amino-3,5-bis(ethoxycarbonyl)-4-methylthiophene (2.0 g, 7.8 mmol), glacial acetic acid (14 ml), propionic acid (2.8 ml), sulfuric acid (10.8 ml), and desalted water (1.2 ml) was cooled with ice, 44 wt % nitrosylsulfuric acid (2.5 g, 8.6 mmol) was added dropwise thereto at 2° C. in the system and then the whole was stirred for 1 hour while a temperature of 0±5° C. in the system was maintained, to form a diazo solution. Into another vessel were introduced C-3 (2.9 g, 7.4 mmol), tetrahydrofuran (40 ml), sulfamic acid (0.24 g), and sodium acetate (5.7 g), and the diazo solution was added dropwise thereto under ice cooling while a temperature of 0±5° C. in the system was maintained. Along the way, ice was additionally added. The reaction mixture was filtered and the filtrate was purified by silica gel column chromatography to obtain the compound 12 (1.45 g, yield 28%).

Example 13

<Synthesis of Compound 13>

The compound 13 was synthesized from the intermediate M-1 and the intermediate C-8 in the same manner as in the synthesis of the compound 1.

Example 14

<Synthesis of Compound 14>

The compound 14 was synthesized from the intermediate M-5 and the intermediate C-9 in the same manner as in the synthesis of the compound 1.

Example 15

<Synthesis of Compound 15>

The compound 15 was synthesized from the intermediate M-1 and the intermediate C-5 in the same manner as in the synthesis of the compound 1.

Comparative Example 1

<Synthesis of Comparative Example Compound 1>

The comparative example compound 1 was synthesized in accordance with Examples of International Publication WO2010/031860.

Comparative Example 2
<Synthesis of Comparative Example Compound 2>
The compound M-2 of JP-A-01-136787 was synthesized as the comparative example compound 2.
Compounds of Examples 1 to 15 and Comparative Examples 1 and 2 are shown below.
[Chem 54]
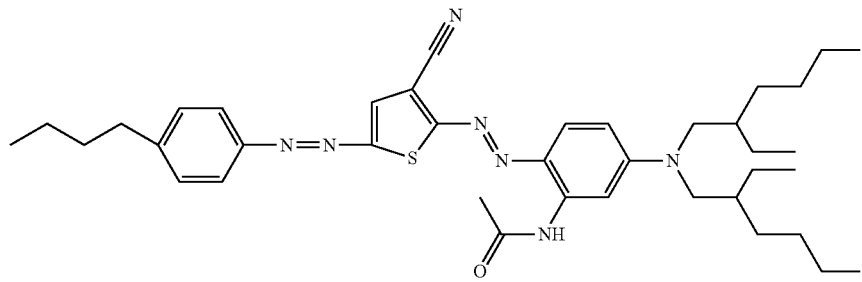
Compound 1
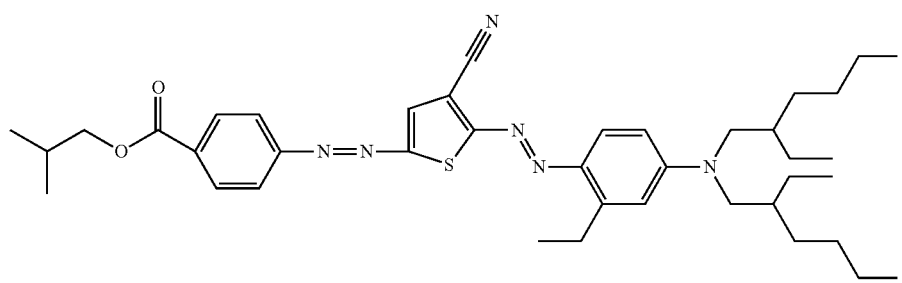
Compound 2
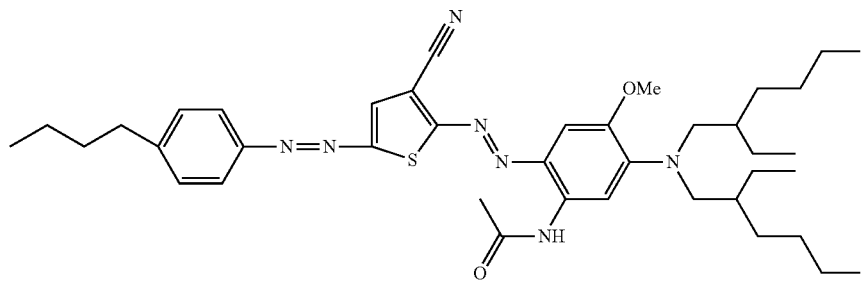
Compound 3
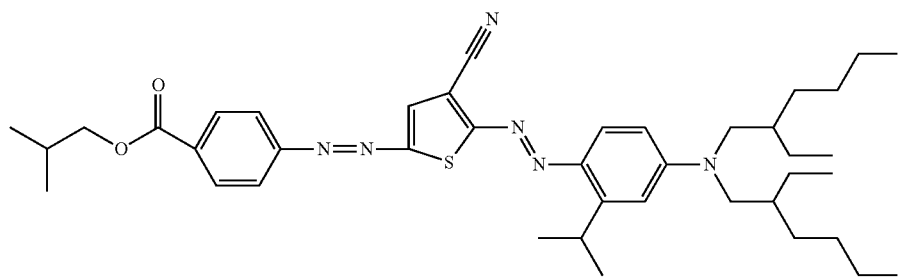
Compound 4
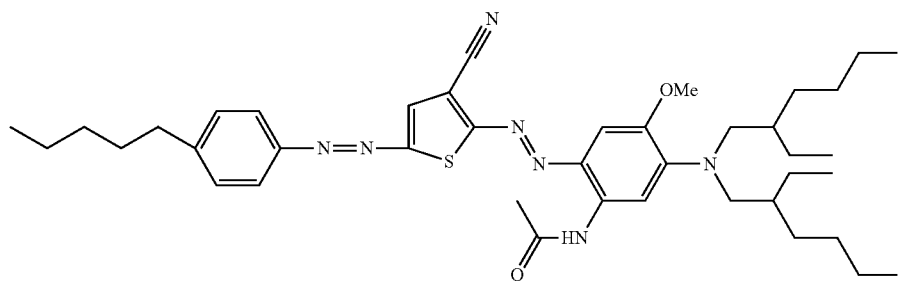
Compound 5

-continued
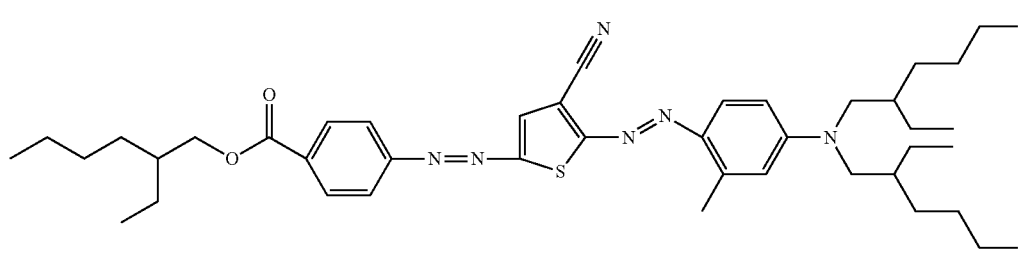
Compound 6
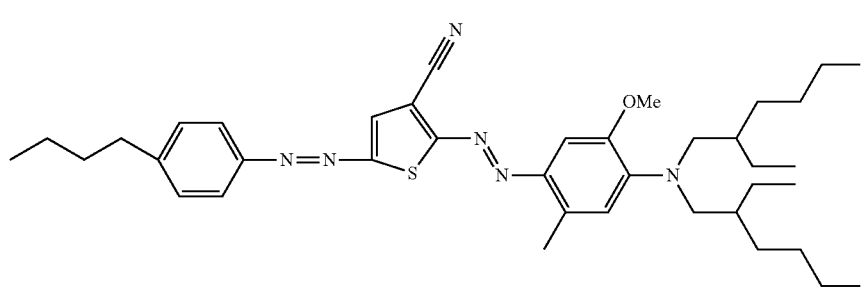
Compound 7
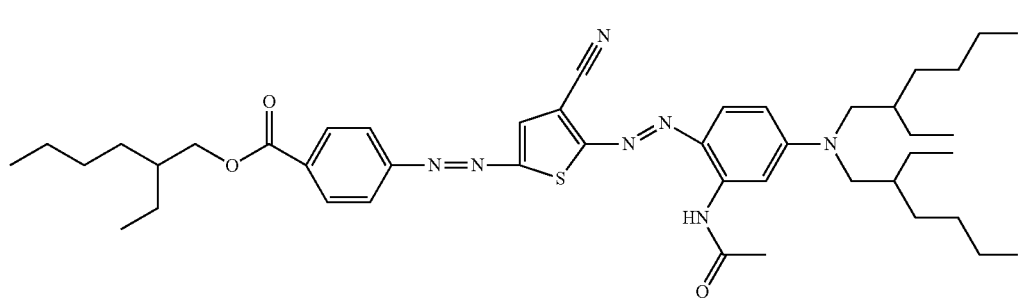
Compound 8
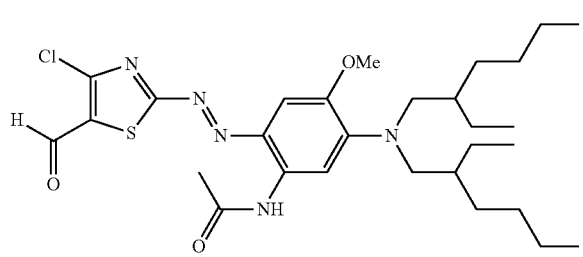
Compound 9
[Chem 55]
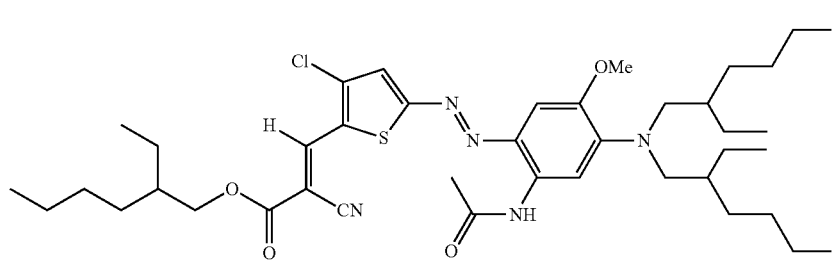
Compound 10

-continued
Compound 11
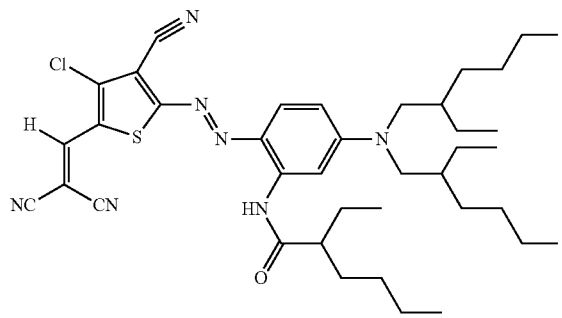
Compound 12
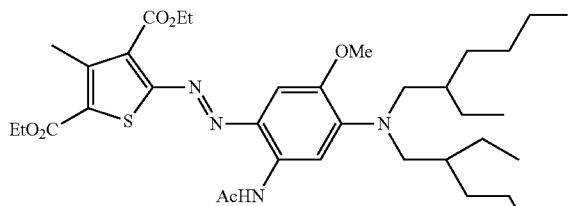
Compound 13
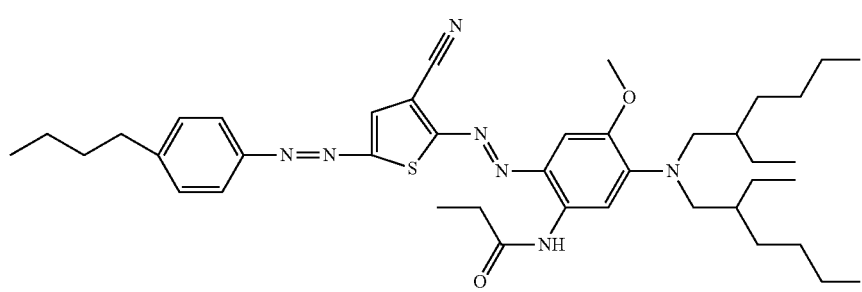
Compound 14
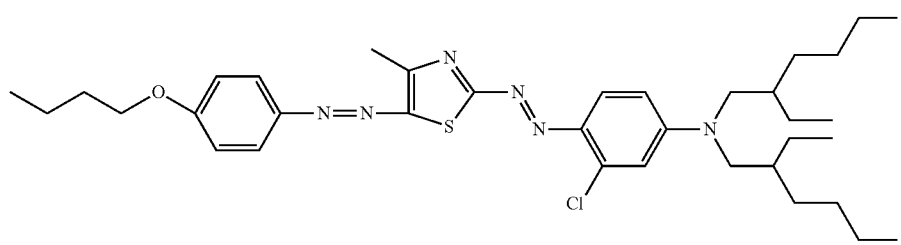
Compound 15
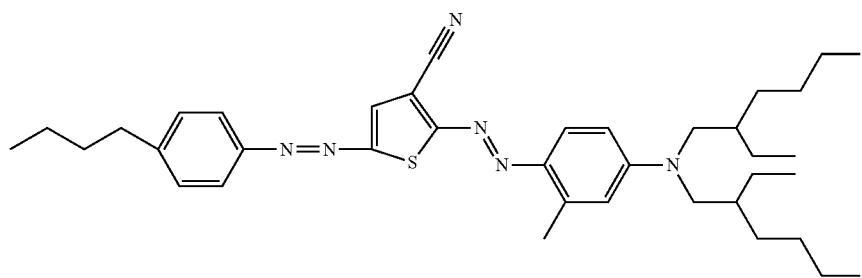
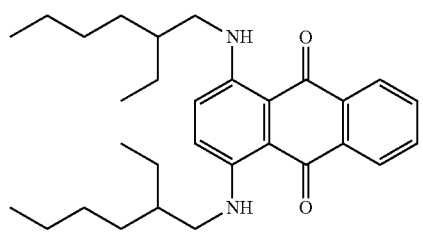
Comparative Example Compound 1
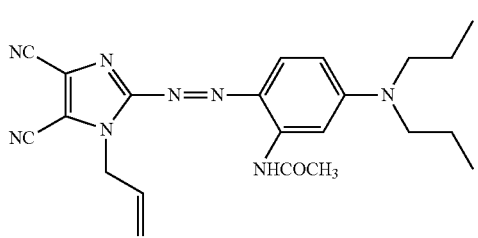

Comparative Example Compound 2

For the compounds 1 to 15 and the comparative example compounds 1 and 2, inks were prepared using n-decaline (relative permittivity 2.0, solubility in water 1 mg/L or less), Isopar M (manufactured by Exxon Mobil Corporation, containing about 75% of branched saturated hydrocarbons having 13 to 17 carbon atoms, relative permittivity 2.1, solubility in water 1 mg/L or less), Isopar L (manufactured by Exxon Mobil Corporation, containing mainly branched saturated hydrocarbons having 11 to 12 carbon atoms and about 20% of branched saturated hydrocarbons having 13 to 17 carbon atoms, relative permittivity 1.9, solubility in water 1 mg/L or less), a mixed solvent of n-decane/Isopar L (mixing ratio (mass ratio) 1/1, relative permittivity 1.9, solubility in water 1 mg/L or less), or a mixed solvent of Isopar L/decaline (mixing ratio (mass ratio) 9/1, relative permittivity 1.9, solubility in water 1 mg/L or less) as a solvent.

The solution colors, absorption-maximum wavelength ($\lambda_{max}$), solubility C at 5° C., molar extinction coefficient $\epsilon$, and $\epsilon$C for each solvent are summarized in Tables 4 to 8.

<Method for Measuring Relative Permittivity of Sovent>

It is measured by the impedance meter method using a precision LCR meter 4284A, manufactured by Agilent Technologies, Inc. Each ink or solvent was sandwiched between flat glass substrates which each had an ITO electrode and which had been disposed parallel so as to face each other at an electrode spacing of 30 μm. Thereafter, the equivalent parallel capacity was measured while applying a test signal voltage of 0.1 V at a frequency of 1 kHz at 22° C. The relative permittivity was determined through the calculation according to the following equation to evaluate the solvent or ink.

Relative permittivity=(equivalent parallel capacity)×(electrode spacing)/(electrode area)/(permittivity in vacuum ($\epsilon_0$))

<Method for Measuring Solubility of Solvent in Water>

Pure water (30 g) and a solvent (8 g) were introduced into 110 ml of a vial, which was shaken 200 times/minute for 4 hours in a constant-temperature tank at 25° C. The mixture after shaking was centrifuged (6000×g, for 5 minutes), the aqueous layer was sampled, and the concentration of the solvent dissolved was quantitatively determined by gas chromatography. Since Isopar was not a single compound but a mixture, the quantitative determination was performed as TOC (total organic carbon), which was converted into solubility according to the following equation, the average molecular weight being shown as Mw.

Solubility [mg/L]=TOC [mg/L]×(14Mw/{12(Mw−2)})

In the case of a mixed solvent in which two or more kinds of solvents were mixed, the solubility in water was determined by multiplying the solubility of each solvent in water by each molar fraction and summing up the resulting products.

In the case where the solvent species used is unclear, the solubility in water can be measured by the above method through identification of the solvent species by mass spectroscopy or the like.

<Method for Measuring Absorption-Maximum Wavelength $\lambda_{Max}$ and Molar Extinction Coefficient $\epsilon$>

Each of the compounds 1 to 15 and the comparative example compounds 1 and 2 (1 mg each) was dissolved in each solvent (100 ml) and measurement of absorption spectra was performed on Hitachi spectrophotometer U-4100 using a quartz cell having an optical path length for measurement of 10 mm. From the resulting spectra, absorption-maximum wavelength $\lambda_{max}$ (nm) and molar extinction coefficient $\epsilon$ (L·mol$^{-2}$·cm$^{-1}$) were determined.

<Method for Measuring Solubility C and $\epsilon$C>

The solubility C of each compound in each solvent was measured as follows.

Each compound was added to each solvent until a dissolution residue came to remain, and the mixture was subjected to an ultrasonic treatment for 30 minutes at 30° C. After the mixture was allowed to stand at 5° C. for 24 hours, centrifugal filtration was performed through a filter of 0.1 μm using a microcentrifuge (centrifugal force 5200×g). The resulting saturated solution was diluted to an appropriate concentration, and measurement of absorption spectra was performed on Hitachi spectrophotometer U-4100 using a quartz cell having an optical path length for measurement of 10 mm. The concentration of each compound was determined from a relationship between the absorbance at the absorption-maximum wavelength $\lambda_{max}$ (nm) and the molar extinction coefficient $\epsilon$ (L·mol$^{-1}$·cm$^{-1}$) previously measured, and the solubility C (mol·L$^{-1}$) was calculated. Moreover, the value of the product of the molar extinction coefficient $\epsilon$ (L·mol$^{-1}$·cm$^{-1}$) and the solubility C (mol·L$^{-1}$), $\epsilon$C, was determined.

TABLE 4

Test results for n-decane

| Compound | Color tone | Absorption-maximum wavelength (nm) | Solubility (mol·L$^{-1}$) | $\epsilon$ (L·mol$^{-1}$·cm$^{-1}$) | $\epsilon$·C (cm$^{-1}$) |
|---|---|---|---|---|---|
| Compound 1 | blue | 619 | 2.4 × 10$^{-2}$ | 76000 | 1800 |
| Compound 2 | blue | 635 | 2.7 × 10$^{-2}$ | 57000 | 1500 |
| Compound 3 | blue | 667 | 1.4 × 10$^{-1}$ | 73000 | 9900 |
| Compound 4 | blue | 638 | 2.7 × 10$^{-2}$ | 66000 | 1800 |
| Compound 5 | blue | 667 | 2.2 × 10$^{-1}$ | 75000 | 16000 |
| Compound 6 | blue | 633 | 1.1 × 10$^{-1}$ | 66000 | 7000 |
| Compound 7 | blue | 640 | 1.4 × 10$^{-1}$ | 50000 | 6900 |
| Compound 8 | blue | 637 | 5.9 × 10$^{-2}$ | 79000 | 4700 |
| Compound 9 | blue | 617 | 5.8 × 10$^{-2}$ | 57000 | 3300 |
| Compound 10 | blue | 656 | 9.3 × 10$^{-2}$ | 61000 | 5700 |
| Compound 11 | blue | 642 | 8.9 × 10$^{-2}$ | 60000 | 5300 |
| Compound 12 | blue | 582 | 2.5 × 10$^{-1}$ | 46000 | 12000 |
| Compound 13 | blue | 667 | 5.9 × 10$^{-2}$ | 76000 | 4400 |
| Compound 14 | red | 546 | 1.5 × 10$^{-1}$ | 47000 | 7100 |
| Compound 15 | blue | 613 | 2.7 × 10$^{-2}$ | 64000 | 1700 |
| Comparative example compound 1 | blue | 652 | 2.7 × 10$^{-2}$ | 17000 | 460 |
| Comparative example compound 2 | red | 512 | 1.0 × 10$^{-5}$ or less | 34000 | 10 or less |

TABLE 5

Test results for tetradecane

| Compound | Color tone | Absorption-maximum wavelength (nm) | Solubility (mol·L$^{-1}$) | $\epsilon$ (L·mol$^{-1}$·cm$^{-1}$) | $\epsilon$·C (cm$^{-1}$) |
|---|---|---|---|---|---|
| Compound 2 | blue | 637 | 2.7 × 10$^{-2}$ | 54000 | 1500 |
| Compound 3 | blue | 669 | 1.5 × 10$^{-1}$ | 73000 | 10600 |
| Compound 4 | blue | 640 | 2.0 × 10$^{-2}$ | 64000 | 1300 |
| Compound 6 | blue | 635 | 1.4 × 10$^{-1}$ | 65000 | 9300 |
| Compound 8 | blue | 639 | 4.4 × 10$^{-2}$ | 79000 | 3500 |
| Compound 9 | blue | 618 | 3.4 × 10$^{-2}$ | 59000 | 3300 |
| Compound 10 | blue | 658 | 3.6 × 10$^{-2}$ | 55000 | 2000 |
| Comparative example compound 1 | blue | 651 | 9.4 × 10$^{-2}$ | 17000 | 1600 |

TABLE 5-continued

Test results for tetradecane

| Compound | Color tone | Absorption-maximum wavelength (nm) | Solubility (mol · L$^{-1}$) | $\epsilon$ (L · mol$^{-1}$ · cm$^{-1}$) | $\epsilon \cdot C$ (cm$^{-1}$) |
|---|---|---|---|---|---|
| Comparative example compound 2 | red | 514 | $1.0 \times 10^{-5}$ or less | 39000 | 10 or less |

TABLE 6

Test results for Isopar M

| Compound | Color tone | Absorption-maximum wavelength (nm) | Solubility (mol · L$^{-1}$) | $\epsilon$ (L · mol$^{-1}$ · cm$^{-1}$) | $\epsilon \cdot C$ (cm$^{-1}$) |
|---|---|---|---|---|---|
| Compound 3 | blue | 668 | $1.5 \times 10^{-1}$ | 72000 | 11100 |
| Compound 6 | blue | 634 | $1.6 \times 10^{-1}$ | 65000 | 10400 |
| Compound 8 | blue | 638 | $4.4 \times 10^{-2}$ | 78000 | 3400 |
| Compound 9 | blue | 618 | $3.4 \times 10^{-2}$ | 59000 | 2000 |
| Compound 10 | blue | 657 | $6.4 \times 10^{-2}$ | 54000 | 5500 |
| Comparative example compound 1 | blue | 651 | $7.1 \times 10^{-2}$ | 17000 | 1200 |
| Comparative example compound 2 | red | 514 | $1.0 \times 10^{-5}$ or less | 39000 | 10 or less |

TABLE 7

Test results for Isopar L

| Compound | Color tone | Absorption-maximum wavelength (nm) | Solubility (mol · L$^{-1}$) | $\epsilon$ (L · mol$^{-1}$ · cm$^{-1}$) | $\epsilon \cdot C$ (cm$^{-1}$) |
|---|---|---|---|---|---|
| Compound 3 | blue | 667 | $1.1 \times 10^{-1}$ | 75000 | 8200 |

TABLE 8

Test results for mixed solvent of n-decane/Isopar L (mixing ratio 1/1)

| Compound | Color tone | Absorption-maximum wavelength (nm) | Solubility (mol · L$^{-1}$) | $\epsilon$ (L · mol$^{-1}$ · cm$^{-1}$) | $\epsilon \cdot C$ (cm$^{-1}$) |
|---|---|---|---|---|---|
| Compound 3 | blue | 667 | $6.3 \times 10^{-2}$ | 75000 | 4700 |

Example 16

<Preparation of Black Ink 1>

A composition 1 composed of the compound 3 and the yellow compound A and the red compound A to be described below were dissolved in n-decane (relative permittivity 2.0, solubility in water 1 mg/L or less, manufactured by Tokyo Chemical Industry Co., Ltd.) to prepare the black ink 1. The recipe of the black ink 1 was as shown in Table 9.

Example 17

<Preparation of Black Ink 2>

A composition 2 composed of the compound 3 and the yellow compound A and the red compound A to be described below were dissolved in n-decane (relative permittivity 2.0, solubility in water 1 mg/L or less, manufactured by Tokyo Chemical Industry Co., Ltd.) to prepare the black ink 2. The recipe of the black ink 2 was as shown in Table 9.

Example 18

<Preparation of Black Ink 3>

A colorant composition 3 composed of the compound 3 and the yellow compound A, the red compound A, and the blue compound A to be described below were dissolved in n-decane (relative permittivity 2.0, solubility in water 1 mg/L or less, manufactured by Tokyo Chemical Industry Co., Ltd.) to prepare the black ink 3. The recipe of the black ink 3 was as shown in Table 9.

Example 19

<Preparation of Black Ink 4>

A composition 4 composed of the compound 3 and the yellow compound A, the red compound A, and the blue compound A to be described below were dissolved in n-decane (relative permittivity 2.0, solubility in water 1 mg/L or less, manufactured by Tokyo Chemical Industry Co., Ltd.) to prepare the black ink 4. The recipe of the black ink 4 was as shown in Table 9.

Example 20

<Preparation of Black Ink 5>

A composition 5 composed of the compound 3 and the yellow compound A, the red compound A, the red compound B, the blue compound A, and the blue compound B to be described below were dissolved in n-decane (relative permittivity 2.0, solubility in water 1 mg/L or less, manufactured by Tokyo Chemical Industry Co., Ltd.) to prepare the black ink 5. The recipe of the black ink 5 was as shown in Table 9.

Example 21

<Preparation of Black Ink 6>

A composition 6 composed of the compound 3 and the yellow compound A, the red compound C, and the blue compound A to be described below were dissolved in n-decane (relative permittivity 2.0, solubility in water 1 mg/L or less, manufactured by Tokyo Chemical Industry Co., Ltd.) to prepare the black ink 6. The recipe of the black ink 6 was as shown in Table 9.

Example 22

<Preparation of Black Ink 7>

A composition 7 composed of the compound 3 and the yellow compound A, the red compound C, the red compound D, and the blue compound A to be described below were dissolved in n-decane (relative permittivity 2.0, solubility in water 1 mg/L or less, manufactured by Tokyo Chemical Industry Co., Ltd.) to prepare the black ink 7. The recipe of the black ink 7 was as shown in Table 9.

Example 23

<Preparation of Black Ink 8>

A composition 8 composed of the compound 3 and the yellow compound A, the red compound C, and the blue compound A to be described below were dissolved in Isopar M (relative permittivity 2.1, solubility in water 1 mg/L or less, manufactured by Exxon Mobil Corporation) to prepare the black ink 8. The recipe of the black ink 8 was as shown in Table 9.

Example 24

<Preparation of Black Ink 9>

A composition 9 composed of the compound 3 and the yellow compound A, the red compound C, the red compound D, and the blue colorant A to be described below were dissolved in Isopar M (relative permittivity 2.1, solubility in water 1 mg/L or less, manufactured by Exxon Mobil Corporation) to prepare the black ink 9. The recipe of the black ink 9 was as shown in Table 9.

Example 25

<Preparation of Black Ink 10>

A composition 10 composed of the compound 3, the compound 12, and the yellow compound A, the red compound C, and the red compound D to be described below were dissolved in n-decane (relative permittivity 2.0, solubility in water 1 mg/L or less) to prepare the black ink 10. The recipe of the black ink 10 was as shown in Table 9.

Example 26

<Preparation of Black Ink 11>

A composition 11 composed of the compound 3, the compound 12, and the yellow compound A, the red compound C, and the red compound D to be described below were dissolved in n-decane (relative permittivity 2.0, solubility in water 1 mg/L or less) to prepare the black ink 11. The recipe of the black ink 11 was as shown in Table 9.

Example 27

<Preparation of Black Ink 12>

A composition 12 composed of the compound 3, and the yellow compound A and the red compound E to be described below were dissolved in n-decane (relative permittivity 2.0, solubility in water 1 mg/L or less) to prepare the black ink 12. The recipe of the black ink 12 was as shown in Table 9.

Example 28

<Preparation of Black Ink 13>

A composition 13 composed of the compound 3, and the yellow compound A, the red compound C, the red compound D, and the blue compound A to be described below were dissolved in n-decane (relative permittivity 2.0, solubility in water 1 mg/L or less) to prepare the black ink 13. The recipe of the black ink 13 was as shown in Table 9.

Example 29

<Preparation of Black Ink 14>

A composition 14 composed of the compound 3, and the yellow compound A, the red compound B, the red compound C, the blue compound A, and the blue compound B to be described below were dissolved in n-decane (relative permittivity 2.0, solubility in water 1 mg/L or less) to prepare the black ink 14. The recipe of the black ink 14 was as shown in Table 9.

Example 30

<Preparation of Black Ink 15>

A composition 15 composed of the compound 3, and the yellow compound A, the red compound B, the red compound C, and the blue compound B to be described below were dissolved in n-decane (relative permittivity 2.0, solubility in water 1 mg/L or less) to prepare the black ink 15. The recipe of the black ink 15 was as shown in Table 9.

Example 31

<Preparation of Black Ink 16>

A composition 16 composed of the compound 3, and the yellow compound A, the red compound C, the red compound D, and the blue compound A to be described below were dissolved in n-decane (relative permittivity 2.0, solubility in water 1 mg/L or less) to prepare the black ink 16. The recipe of the black ink 16 was as shown in Table 9.

Example 32

<Preparation of Black Ink 17>

A composition 17 composed of the compound 3, and the yellow compound A, the red compound C, the red compound D, and the blue compound A to be described below were dissolved in n-decane (relative permittivity 2.0, solubility in water 1 mg/L or less) to prepare the black ink 17. The recipe of the black ink 17 was as shown in Table 9.

Example 33

<Preparation of Black Ink 18>

A composition 18 composed of the compound 3, and the yellow compound A and the red compound E to be described below were dissolved in Isopar L (relative permittivity 1.9, solubility in water 1 mg/L or less) to prepare the black ink 18. The recipe of the black ink 18 was as shown in Table 9.

Example 34

<Preparation of Black Ink 19>

A composition 19 composed of the compound 3, and the yellow compound A and the red compound E to be described below were dissolved in a mixed solvent of n-decane/Isopar L (mixing ratio (mass ratio) 1/1, relative permittivity 1.9, solubility in water 1 mg/L or less) to prepare the black ink 19. The recipe of the black ink 19 was as shown in Table 9.

Example 35

<Preparation of Black Ink 20>

A composition 20 composed of the compound 4, and the yellow compound A and the red compound E to be described below were dissolved in n-decane (relative permittivity 2.0, solubility in water 1 mg/L or less) to prepare the black ink 20. The recipe of the black ink 20 was as shown in Table 9.

Example 36

<Preparation of Black Ink 21>

A composition 21 composed of the compound 3, and the yellow compound A and the red compound E to be described below were dissolved in a mixed solvent of Isopar L/decaline (mixing ratio (mass ratio) 9/1, relative permittivity 1.9, solubility in water 1 mg/L or less) to prepare the black ink 21. The recipe of the black ink 21 was as shown in Table 9.

Example 37

<Preparation of Black Ink 22>

A composition 22 composed of the compound 3, and the yellow compound A and the red compound E to be described below were dissolved in n-decane (relative permittivity 2.0, solubility in water 1 mg/L or less) to prepare the black ink 22. The recipe of the black ink 22 was as shown in Table 9.

Example 38

<Preparation of Black Ink 23>

A composition 23 composed of the compound 3 and the compound 4, and the yellow compound A and the red compound E to be described below were dissolved in n-decane (relative permittivity 2.0, solubility in water 1 mg/L or less) to prepare the black ink 23. The recipe of the black ink 23 was as shown in Table 9.

Example 39

<Preparation of Black Ink 24>

A composition 24 composed of the compound 3 and the compound 4, and the yellow compound A and the red compound E to be described below were dissolved in Isopar L (relative permittivity 1.9, solubility in water 1 mg/L or less) containing carbon black (Furnace Black, manufactured by Mitsubishi Chemical Corporation) dispersed therein in a concentration of 10% by mass, to prepare the black ink 24. The recipe of the black ink 24 was as shown in Table 9.

Example 40

<Preparation of Black Ink 25>

A composition 25 composed of the compound 4, and the yellow compound A and the red compound E to be described below were dissolved in n-decane (relative permittivity 2.0, solubility in water 1 mg/L or less) to prepare the black ink 25. The recipe of the black ink 25 was as shown in Table 9.

Example 41

<Preparation of Black Ink 26>

A composition 26 composed of the compound 4, and the yellow compound A and the red compound E to be described below were dissolved in n-decane (relative permittivity 2.0, solubility in water 1 mg/L or less) to prepare the black ink 26. The recipe of the black ink 26 was as shown in Table 9.

Example 42

<Preparation of Black Ink 27>

A composition 27 composed of the compound 4, and the yellow compound A and the red compound E to be described below were dissolved in n-decane (relative permittivity 2.0, solubility in water 1 mg/L or less) to prepare the black ink 27. The recipe of the black ink 27 was as shown in Table 9.

Example 43

<Preparation of Black Ink 28>

A composition 28 composed of the compound 3, and the yellow compound A and the red compound E to be described below were dissolved in Isopar L (relative permittivity 1.9, solubility in water 1 mg/L or less) containing carbon black (Furnace Black, manufactured by Mitsubishi Chemical Corporation) dispersed therein in a concentration of 10% by mass, to prepare the black ink 28. The recipe of the black ink 28 was as shown in Table 9.

Example 44

<Preparation of Black Ink 29>

A composition 29 composed of the compound 3 and the compound 4, and the yellow compound A and the red compound E to be described below were dissolved in n-decane (relative permittivity 2.0, solubility in water 1 mg/L or less) to prepare the black ink 29. The recipe of the black ink 29 was as shown in Table 9.

Yellow Compound A (Compound Described in International Publication WO2009/063880)

[Chem 56]

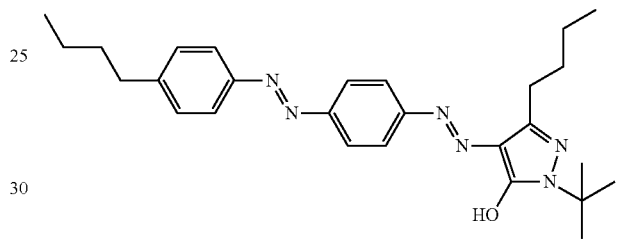

Yellow compound A

Red Compound A

A mixture of H-1 (0.50 g, 3.3 mmol), glacial acetic acid (3 ml), propionic acid (0.7 ml), sulfuric acid (2.7 ml), and desalted water (0.3 ml) were cooled on an ice bath, 44 wt % nitrosylsulfuric acid (1.0 g, 3.6 mmol) was added dropwise thereto at 1° C. in the system, and then the whole was stirred for 1 hour while a temperature of 0±5° C. in the system was maintained, to obtain a diazo solution. Into another vessel were introduced C-1 (0.81 g, 3.1 mmol), tetrahydrofuran (40 ml), sulfamic acid (0.06 g, 0.6 mmol), and sodium acetate (5.7 g), and the diazo solution was added dropwise thereto under ice cooling while a temperature of 0±5° C. in the system was maintained. Along the way, ice and tetrahydrofuran (40 ml) were additionally added. After the completion of the dropwise addition, an aqueous sodium acetate solution was added to adjust the pH to 4. After extraction with toluene, the resulting extract was concentrated under reduced pressure, the concentrate was purified by silica gel column chromatography, and the formed solid was washed with methanol/water (1/1 (volume ratio)) to synthesize the red compound A (0.45 g, yield 32%).

[Chem 57]

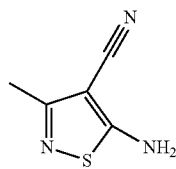

H-1

Red compound A

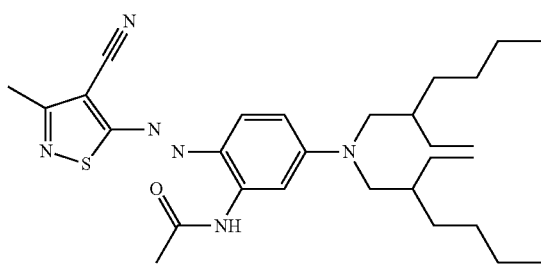

Red Compound B

The red compound B was synthesized in the same manner as in the case of the red compound A except that H-2 was used instead of H-1 and C-5 was used instead of C-1.

[Chem 59]

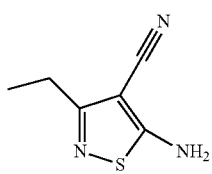

H-2

[Chem 60]

Red compound B

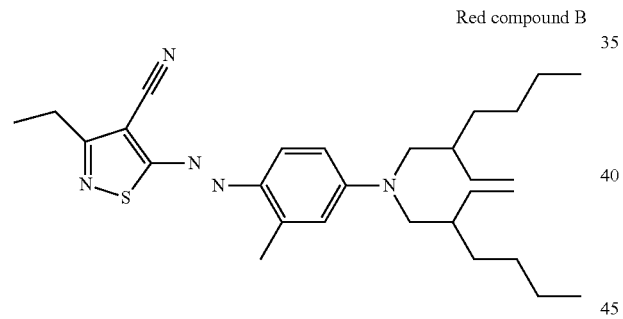

Red Compound C

The red compound C was synthesized in the same manner as in the case of the red compound A except that C-10 was used instead of C-1.

[Chem 61]

Red compound C

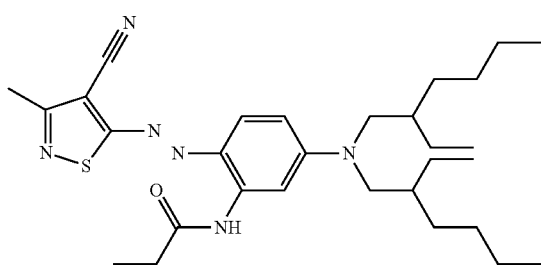

Red Compound D

The red compound D was synthesized in the same manner as in the case of the red compound A except that C-2 was used instead of C-1.

[Chem 62]

Red compound D

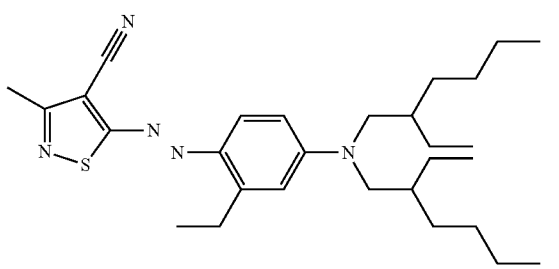

Red Compound E

The red compound E was synthesized in the same manner as in the case of the red compound A except that H-2 was used instead of H-1.

[Chem 63]

Red compound E

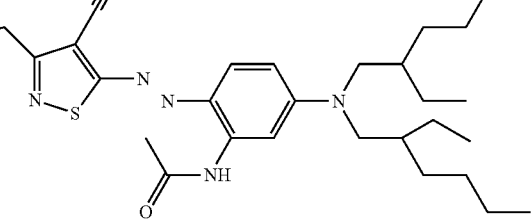

Blue Compound A (Compound Described in JP-A-11-124510)

[Chem 64]

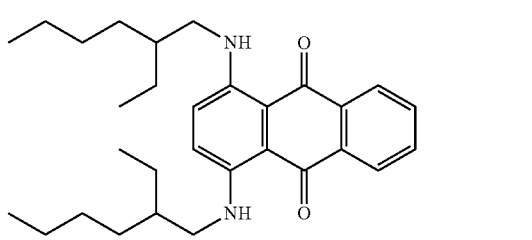

Blue Compound B (Compound Described in JP-A-2000-313174)

[Chem 65]

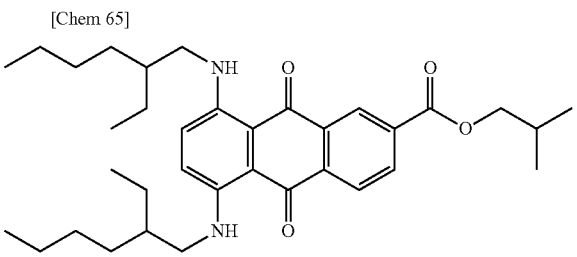

Comparative Example 3

Sudan Black B (manufactured by Tokyo Chemical Industry Co., Ltd.) that is a commercially available oil-soluble black dye was added to n-decane (relative permittivity 2.0, solubility in water 1 mg/L or less) until a dissolution residue came to remain, and the mixture was subjected to an ultrasonic treatment for 30 minutes at 30° C. After the mixture was allowed to stand at 5° C. for 24 hours, centrifugal filtration was performed through a filter of 0.1 μm using a microcentrifuge (centrifugal force 5200×g). The resulting saturated n-decane solution was diluted to an appropriate concentration. When the solubility of the compound was calculated from a relationship with the extinction coefficient previously measured, the solubility was 0.13% by mass.

A saturated decane solution of Sudan Black B was prepared and used as an ink of Comparative Example 3.

[Chem 66]

Sudan Black B

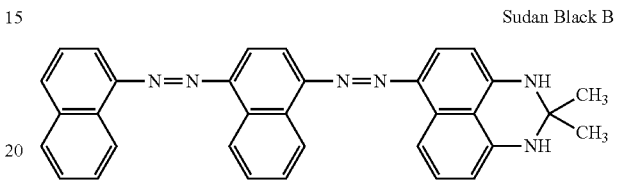

TABLE 9

| | Solvent | | | | | | | | | |
|---|---|---|---|---|---|---|---|---|---|---|
| | n-Decane (g) | Isopar M (g) | Isopar L (g) | Mixed solvent of n-decane/Isopar L (mixing ratio 1/1) (g) | Mixed solvent of Isopar L/decaline (mixing ratio 1/1) (g) | CB/Isopar L dispersion (g) | Compound 3 (g) | Compound 4 (g) | Compound 12 (g) | Yellow Compound A (g) |
| Black ink 1 | 16.000 | — | — | — | — | — | 1.700 | — | — | 1.100 |
| Black ink 2 | 0.780 | — | — | — | — | — | 0.083 | — | — | 0.056 |
| Black ink 3 | 0.730 | — | — | — | — | — | 0.083 | — | — | 0.053 |
| Black ink 4 | 0.710 | — | — | — | — | — | 0.083 | — | — | 0.080 |
| Black ink 5 | 0.570 | — | — | — | — | — | 0.083 | — | — | 0.110 |
| Black ink 6 | 0.650 | — | — | — | — | — | 0.100 | — | — | 0.110 |
| Black ink 7 | 0.640 | — | — | — | — | — | 0.100 | — | — | 0.110 |
| Black ink 8 | — | 0.640 | — | — | — | — | 0.100 | — | — | 0.110 |
| Black ink 9 | — | 0.640 | — | — | — | — | 0.100 | — | — | 0.110 |
| Black ink 10 | 0.566 | — | — | — | — | — | 0.098 | — | 0.016 | 0.062 |
| Black ink 11 | 0.563 | — | — | — | — | — | 0.098 | — | 0.016 | 0.062 |
| Black ink 12 | 0.814 | — | — | — | — | — | 0.083 | — | — | 0.056 |
| Black ink 13 | 0.702 | — | — | — | — | — | 0.100 | — | — | 0.078 |
| Black ink 14 | 0.770 | — | — | — | — | — | 0.025 | — | — | 0.047 |
| Black ink 15 | 0.720 | — | — | — | — | — | 0.050 | — | — | 0.078 |
| Black ink 16 | 0.880 | — | — | — | — | — | 0.123 | — | — | 0.078 |
| Black ink 17 | 0.885 | — | — | — | — | — | 0.123 | — | — | 0.078 |
| Black ink 18 | — | — | 0.415 | — | — | — | 0.066 | — | — | 0.045 |
| Black ink 19 | — | — | — | 0.711 | — | — | 0.040 | — | — | 0.027 |
| Black ink 20 | 0.754 | — | — | — | — | — | — | 0.125 | — | 0.063 |
| Black ink 21 | — | — | — | — | 0.814 | — | 0.083 | — | — | 0.056 |
| Black ink 22 | 0.495 | — | — | — | — | — | 0.250 | — | — | 0.130 |
| Black ink 23 | 0.480 | — | — | — | — | — | 0.100 | 0.165 | — | 0.130 |
| Black ink 24 | — | — | — | — | — | 1.000 | 0.070 | 0.110 | — | 0.053 |
| Black ink 25 | 0.758 | — | — | — | — | — | — | 0.120 | — | 0.062 |
| Black ink 26 | 0.833 | — | — | — | — | — | — | 0.083 | — | 0.043 |
| Black ink 27 | 0.682 | — | — | — | — | — | — | 0.158 | — | 0.082 |
| Black ink 28 | — | — | — | — | — | 0.897 | 0.069 | — | — | 0.007 |
| Black ink 29 | 0.601 | — | — | — | — | — | 0.077 | 0.127 | — | 0.101 |
| Ink of Comparative Example 3 | — | — | — | — | — | — | — | — | — | — |

| | Red Compound A (g) | Red Compound B (g) | Red Compound C (g) | Red Compound D (g) | Red Compound E (g) | Blue Compound A (g) | Blue Compound B (g) | Sudan Black B (mg) |
|---|---|---|---|---|---|---|---|---|
| Black ink 1 | 0.940 | — | — | — | — | — | — | — |
| Black ink 2 | 0.080 | — | — | — | — | — | — | — |
| Black ink 3 | 0.080 | — | — | — | — | 0.050 | — | — |
| Black ink 4 | 0.080 | — | — | — | — | 0.050 | — | — |
| Black ink 5 | 0.080 | 0.019 | — | — | — | 0.033 | 0.100 | — |

TABLE 9-continued

| | | | | | | | | |
|---|---|---|---|---|---|---|---|---|
| Black ink 6 | — | — | 0.095 | — | — | 0.050 | — | — |
| Black ink 7 | — | — | 0.070 | 0.030 | — | 0.050 | — | — |
| Black ink 8 | — | — | 0.095 | — | — | 0.050 | — | — |
| Black ink 9 | — | — | 0.070 | 0.030 | — | 0.050 | — | — |
| Black ink 10 | — | — | 0.012 | 0.046 | — | — | — | — |
| Black ink 11 | — | — | 0.012 | 0.048 | — | — | — | — |
| Black ink 12 | — | — | — | — | 0.047 | — | — | — |
| Black ink 13 | — | — | 0.024 | 0.056 | — | 0.040 | — | — |
| Black ink 14 | — | 0.024 | 0.025 | — | — | 0.025 | 0.084 | — |
| Black ink 15 | — | 0.025 | 0.030 | — | — | — | 0.101 | — |
| Black ink 16 | — | — | 0.024 | 0.056 | — | 0.040 | — | — |
| Black ink 17 | — | — | 0.024 | 0.050 | — | 0.040 | — | — |
| Black ink 18 | — | — | — | — | 0.038 | — | — | — |
| Black ink 19 | — | — | — | — | 0.023 | — | — | — |
| Black ink 20 | — | — | — | — | 0.059 | — | — | — |
| Black ink 21 | — | — | — | — | 0.047 | — | — | — |
| Black ink 22 | — | — | — | — | 0.125 | — | — | — |
| Black ink 23 | — | — | — | — | 0.125 | — | — | — |
| Black ink 24 | — | — | — | — | 0.076 | — | — | — |
| Black ink 25 | — | — | — | — | 0.060 | — | — | — |
| Black ink 26 | — | — | — | — | 0.041 | — | — | — |
| Black ink 27 | — | — | — | — | 0.079 | — | — | — |
| Black ink 28 | — | — | — | — | 0.028 | — | — | — |
| Black ink 29 | — | — | — | — | 0.096 | — | — | — |
| Ink of Comparative Example 3 | — | — | — | — | — | — | — | 13.000 |

<Hue Evaluation>

Spectra were measured using a cell having an optical path length for measurement of 0.01 mm for Black inks 1 to 20 and the ink of Comparative Example 3, using a cell having an optical path length for measurement of 0.004 mm for black inks 21 and 25 to 28, and using a cell having an optical path length for measurement of 0.002 mm for black inks 22 to 24 and 29. Color measurement was made using the color calculation program attached to Hitachi spectrophotometer U-4100, under the conditions of D65 light source and a viewing angle of 2 degrees. Thus, each ink was quantitatively evaluated for hue.

The results of the hue evaluation for black inks 1 to 29 and the ink of Comparative Example 3 are shown in Table 10.

TABLE 10

| Black ink | Optical path length for measurement (mm) | Hue evaluation results | | | |
|---|---|---|---|---|---|
| | | $L^*$ | $a^*$ | $b^*$ | $C^*$ |
| Black ink 1 | 0.01 | 8.89 | 2.32 | 4.24 | 4.83 |
| Black ink 2 | 0.01 | 3.85 | 9.51 | 0.75 | 9.54 |
| Black ink 3 | 0.01 | 1.01 | 3.08 | −2.85 | 4.20 |
| Black ink 4 | 0.01 | 1.18 | 2.17 | 0.68 | 2.27 |
| Black ink 5 | 0.01 | 0.26 | 0.33 | 0.20 | 0.39 |
| Black ink 6 | 0.01 | 0.40 | 0.74 | 0.42 | 0.85 |
| Black ink 7 | 0.01 | 0.43 | 0.81 | 0.48 | 0.94 |
| Black ink 8 | 0.01 | 0.29 | 0.59 | 0.28 | 0.65 |
| Black ink 9 | 0.01 | 0.32 | 0.60 | 0.29 | 0.67 |
| Black ink 10 | 0.01 | 0.04 | 0.01 | −0.02 | 0.02 |
| Black ink 11 | 0.01 | 0.81 | 0.02 | −0.02 | 0.03 |
| Black ink 12 | 0.01 | 2.12 | 0.76 | 1.41 | 1.61 |
| Black ink 13 | 0.01 | 0.05 | 0.02 | −0.01 | 0.02 |
| Black ink 14 | 0.01 | 0.18 | 0.38 | 0.09 | 0.39 |
| Black ink 15 | 0.01 | 0.10 | 0.08 | 0.03 | 0.08 |
| Black ink 16 | 0.01 | 0.05 | 0.01 | −0.02 | 0.02 |
| Black ink 17 | 0.01 | 0.04 | 0.01 | −0.02 | 0.02 |
| Black ink 18 | 0.01 | 0.06 | 0.01 | −0.01 | 0.02 |
| Black ink 19 | 0.01 | 1.30 | 0.44 | 0.75 | 0.87 |
| Black ink 20 | 0.01 | 0.04 | 0.04 | −0.01 | 0.04 |
| Black ink 21 | 0.004 | 12.69 | 2.41 | 3.30 | 4.08 |
| Black ink 22 | 0.002 | 4.98 | 1.22 | −0.63 | 1.37 |
| Black ink 23 | 0.002 | 1.88 | 2.50 | −5.07 | 5.65 |
| Black ink 24 | 0.002 | 9.23 | 0.52 | −8.23 | 8.25 |
| Black ink 25 | 0.004 | 1.10 | 0.46 | −0.44 | 0.64 |
| Black ink 26 | 0.004 | 13.90 | 2.50 | −5.07 | 5.65 |
| Black ink 27 | 0.004 | 1.00 | 0.42 | −0.38 | 0.56 |
| Black ink 28 | 0.004 | 0.84 | 0.17 | −0.90 | 0.91 |
| Black ink 29 | 0.002 | 10.88 | −0.61 | −2.76 | 2.82 |
| Ink of Comparative Example 3 | 0.01 | 91.80 | 1.51 | −1.63 | 2.22 |

It is realized from Table 10 that black inks 1 to 29 have a value of $L^*$ close to 0 as compared with the ink of Comparative Example 3 and $C^*$ of 10 or less, and are satisfactory black inks having an excellent black hue.

While the invention has been described in detail and with reference to specific embodiments thereof, it will be apparent to one skilled in the art that various changes and modifications can be made therein without departing from the spirit and scope thereof.

The present application is based on Japanese Patent Application No. 2011-113759 filed on May 20, 2011, Japanese Patent Application No. 2011-219414 filed on Oct. 3, 2011, Japanese Patent Application No. 2012-005119 filed on Jan. 13, 2012, and Japanese Patent Application No. 2012-086605 filed on Apr. 5, 2012, and the contents are incorporated herein by reference.

Industrial Applicability

The ink and azo compound of the invention are suitably used for displays and optical shutters, especially, for example, suitably used as electrowetting displays such as electronic paper and as electrophoretic displays.

The invention claimed is:

1. An ink comprising: a solvent having a relative permittivity of 3 or less, as measured at a frequency of 1 kHz and at 22° C., and having a solubility in water of 20 mg/L or less at 25° C.; and an azo compound, the azo compound being represented by formula (I):

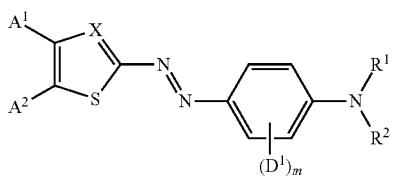

wherein
$R^1$, $R^2$, $D^1$, and $A^1$ each independently represent an arbitrary substituent,
$A^2$ represents a substituent of formula (II):

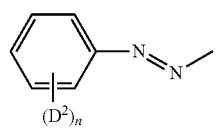

wherein $D^2$ represents an arbitrary substituent, n represents an integer of 1 to 5, and when n is 2 or larger, two or more $D^2$ groups present in one molecule may be the same or different,
m represents an integer of 1 to 4, and when m is 2 or larger, two or more $D^1$ groups present in one molecule may be the same or different, and
X represents a nitrogen atom or an optionally substituted methine group.

2. The ink according to claim 1, wherein the solvent contains at least one selected from the group consisting of hydrocarbon solvents, silicone oils, and fluorocarbon solvents.

3. The ink according to claim 1, wherein the product of a molar extinction coefficient $\epsilon$ ($L \cdot mol^{-1} \cdot cm^{-1}$) at the absorption-maximum wavelength of an n-decane solution of the azo compound and a saturated concentration C ($mol \cdot L^{-1}$) of the azo compound in n-decane at 5° C., $\epsilon C$, is 1,000 $cm^{-1}$ or larger.

4. The ink according to claim 1, which further comprises at least one selected from the group consisting of heterocyclic compounds, cyanovinyl compounds, and anthraquinone compounds.

5. The ink according to claim 4, wherein the heterocyclic compound is at least one selected from the group consisting of formulae (III) to (V):

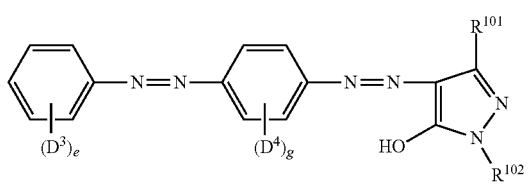

wherein
$R^{101}$, $R^{102}$, $D^3$, and $D^4$ each independently represent an arbitrary substituent,
e represents an integer of 1 to 5, and when e is 2 or larger, two or more $D^3$ groups present in one molecule may be the same or different, and
g represents an integer of 1 to 4, and when g is 2 or larger, two or more $D^4$ groups present in one molecule may be the same or different;

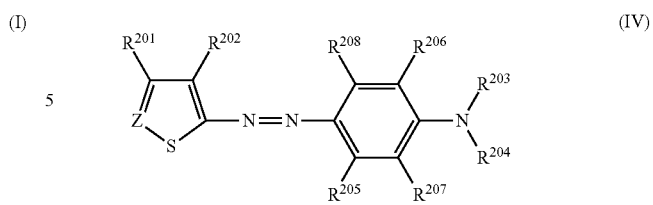

wherein
$R^{201}$, $R^{202}$, $R^{203}$, $R^{204}$, $R^{205}$, $R^{206}$, $R^{207}$, and $R^{208}$ each independently represent an arbitrary substituent and
Z represents a nitrogen atom or an optionally substituted methine group;

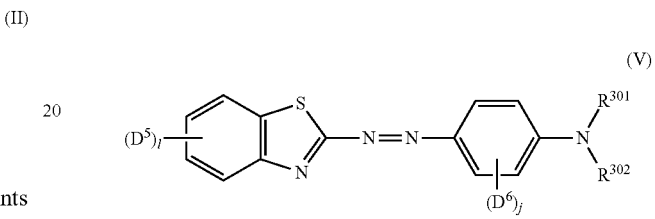

wherein
$R^{301}$, $R^{302}$, $D^5$, and $D^6$ each independently represent an arbitrary substituent,
l represents an integer of 1 to 4, and when l is 2 or larger, two or more $D^5$ groups present in one molecule may be the same or different, and
j represents an integer of 1 to 4, and when j is 2 or larger, two or more $D^6$ groups present in one molecule may be the same or different.

6. The ink according to claim 4, wherein the cyanovinyl compound is represented by formula (VI):

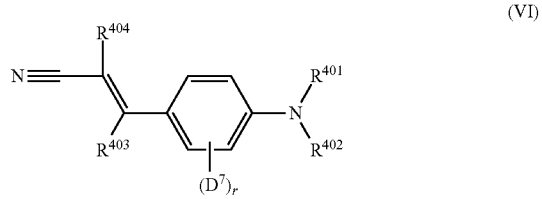

wherein
$R^{401}$, $R^{402}$, $R^{403}$, $R^{404}$, and $D^7$ each independently represent an arbitrary substituent and
r represents an integer of 1 to 4, and when r is 2 or larger, two or more $D^7$ groups present in one molecule may be the same or different.

7. The ink according to claim 4, wherein the anthraquinone compound is represented by formula (VII):

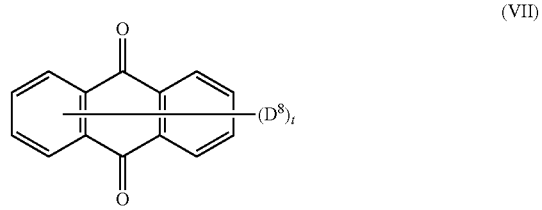

wherein
D⁸ represents an arbitrary substituent and t represents an integer of 1 to 8, and when t is 2 or larger, two or more D⁸ groups present in one molecule may be the same or different.

8. A display or optical shutter, comprising the ink according to claim 1.

9. A display comprising a display part containing the ink according to claim 1, wherein an image is displayed by controlling voltage application to the display part.

10. The display according to claim 9, wherein the display part further contains electrophoretic particles or an aqueous medium.

11. The display according to claim 9, wherein an image is displayed by changing a colored state by means of voltage application.

12. The display according to claim 9, wherein an image is displayed by an electrowetting system or an electrophoretic system.

13. An electronic paper which comprises the display according to claim 9.

14. An azo compound represented by formula (IX):

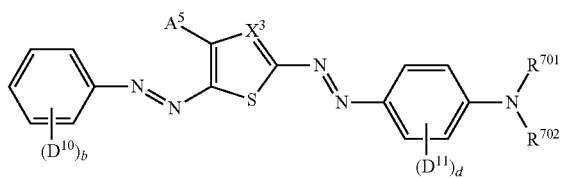

(IX)

wherein
$R^{701}$ and $R^{702}$ each independently represent an optionally substituted branched alkyl group having 5 to 20 carbon atoms, $D^{11}$ represents a hydrogen atom, a halogen atom, an optionally substituted alkyl group having 1 to 20 carbon atoms, an optionally substituted alkoxy group having 1 to 20 carbon atoms, an —NHCOR⁷⁰³ group, or an —NHSO₂R⁷⁰⁸ group, $R^{703}$ and $R^{708}$ each independently represent an optionally substituted alkyl group having 1 to 20 carbon atoms, an optionally substituted aryl group having 6 to 20 carbon atoms, or an optionally substituted heteroaryl group having 2 to 20 carbon atoms, d represents an integer of 1 to 4, and when d is 2 or larger, two or more $D^{11}$ groups present in one molecule may be the same or different, $A^5$ represents a hydrogen atom, a halogen atom, a cyano group, an optionally substituted alkyl group having 1 to 20 carbon atoms, an optionally substituted aryl group having 6 to 20 carbon atoms, an optionally substituted heteroaryl group having 2 to 20 carbon atoms, an optionally substituted alkoxy group having 1 to 20 carbon atoms, or a —COOR⁷⁰⁴ group, $R^{704}$ represents an optionally substituted alkyl group having 1 to 20 carbon atoms, an optionally substituted aryl group having 6 to 20 carbon atoms, or an optionally substituted heteroaryl group having 2 to 20 carbon atoms, $D^{10}$ represents an alkyl group having 1 to 6 carbon atoms, an alkoxy group having 1 to 6 carbon atoms or a —COOR⁷⁰⁶ group, b represents an integer of 1

$R^{706}$ represents an alkyl group having 1 to 20 carbon atoms, $X^3$ represents a nitrogen atom, or a methine group which may have a halogen atom, a cyano group, or a —COOR⁷⁰⁷ group as a substituent, and $R^{707}$ represents an optionally substituted alkyl group having 1 to 20 carbon atoms, an optionally substituted aryl group having 6 to 20 carbon atoms, or an optionally substituted heteroaryl group having 2 to 20 carbon atoms.

15. The azo compound according to claim 14, wherein $R^{701}$ and $R^{702}$ each independently represent a branched alkyl group having at least 8 carbon atoms.

16. The azo compound according to claim 14, wherein $D^{10}$ represents an alkyl group having 1 to 6 carbon atoms, which binds at the para-position with respect to the azo group.

* * * * *